United States Patent
Heidebrecht, Jr. et al.

(10) Patent No.: US 9,339,029 B2
(45) Date of Patent: May 17, 2016

(54) HYDRAZINYL LIPIDOIDS AND USES THEREOF

(71) Applicant: Preceres Inc., Cambridge, MA (US)

(72) Inventors: Richard Wayne Heidebrecht, Jr., Somerville, MA (US); Cheng Zhong, Belmont, MA (US)

(73) Assignee: Preceres Inc., Cambridge, MA (US)

( * ) Notice: Subject to any disclaimer, the term of this patent is extended or adjusted under 35 U.S.C. 154(b) by 0 days.

(21) Appl. No.: 14/844,952

(22) Filed: Sep. 3, 2015

(65) Prior Publication Data

US 2016/0066569 A1    Mar. 10, 2016

Related U.S. Application Data

(60) Provisional application No. 62/045,906, filed on Sep. 4, 2014.

(51) Int. Cl.

| | |
|---|---|
| *A01N 25/12* | (2006.01) |
| *A01N 57/16* | (2006.01) |
| *A61K 9/16* | (2006.01) |
| *C07C 243/14* | (2006.01) |
| *C07D 231/08* | (2006.01) |
| *C12N 15/113* | (2010.01) |
| *A61K 31/713* | (2006.01) |
| *A61K 31/714* | (2006.01) |

(52) U.S. Cl.
CPC ............... *A01N 25/12* (2013.01); *A01N 57/16* (2013.01); *A61K 9/1617* (2013.01); *A61K 31/713* (2013.01); *C07C 243/14* (2013.01); *C07D 231/08* (2013.01); *C12N 15/113* (2013.01); *C12N 2310/14* (2013.01); *C12N 2320/32* (2013.01)

(58) Field of Classification Search
CPC ...... A01N 25/12; A01N 57/16; C07C 243/14; C12N 15/113; C12N 2310/14; C12N 2320/32; A61K 31/713; A61K 9/1617
See application file for complete search history.

(56) References Cited

U.S. PATENT DOCUMENTS

| | | | |
|---|---|---|---|
| 4,374,271 A | 2/1983 | Hunter et al. | |
| 8,450,298 B2 * | 5/2013 | Mahon | A61K 9/1271 514/80 |
| 8,466,122 B2 * | 6/2013 | Heyes | A61K 9/1272 424/450 |
| 8,731,655 B2 * | 5/2014 | Rajagopalan | A61K 31/473 604/20 |
| 9,018,187 B2 * | 4/2015 | Heyes | 514/44 A |
| 9,187,748 B2 * | 11/2015 | Geisbert | C12N 15/1131 |
| 2011/0009641 A1 | 1/2011 | Anderson et al. | |
| 2011/0293703 A1 | 12/2011 | Mahon et al. | |
| 2012/0053511 A1 | 3/2012 | Rajagopalan | |
| 2013/0236256 A1 | 9/2013 | Kaufmann et al. | |
| 2013/0302401 A1 | 11/2013 | Ma et al. | |
| 2014/0134260 A1 * | 5/2014 | Heyes | A61K 31/713 424/499 |
| 2015/0064242 A1 * | 3/2015 | Heyes | A61K 9/145 424/451 |

FOREIGN PATENT DOCUMENTS

| | | |
|---|---|---|
| WO | WO-2006/138380 A2 | 12/2006 |
| WO | WO-2010/053572 A2 | 5/2010 |

OTHER PUBLICATIONS

PubChem, "1-[2,2-bis(-hydroxypropyl)hydrazinyl)propan-2-ol"; Feb. 8, 2011; PubChem, Open Chemistry Database, Substance Record for SID 104460962, External ID AC1L5W05.*
Mueller et al. "Long-term in vitro culture of hamster pancreatic 8-cells and induction of adenocarcinoma by treatment with N-nitrosobis(2-oxopropyl)amine". Pancreatology, 2012, vol. 12, Issue 4, pp. 380-387.
"1-[2,2-bis(-hydroxypropyl)hydrazinyl]propan-2-ol", PubChem, Open Chemistry Database, Substance Record for SID 104460962, External ID AC1L5W02, Deposit Date/Available Date Feb. 8, 2011.
Invitation to Pay Additional Fees and, Where applicable, Protest Fee (Form PCT/ISA/206) International Application No. PCT/US2015/048381, International Filing Date Sep. 3, 2015.

* cited by examiner

*Primary Examiner* — Jane C Oswecki
(74) *Attorney, Agent, or Firm* — McCarter & English, LLP

(57) ABSTRACT

The present disclosure is directed to hydrazinyl lipidoids, formulations thereof further comprising at least one active agent, as well as methods of delivering the at least one active agent to a target organism.

24 Claims, No Drawings

HYDRAZINYL LIPIDOIDS AND USES THEREOF

RELATED APPLICATIONS

This application claims priority to U.S. Provisional Patent Application Ser. No. 62/045,906, filed Sep. 4, 2014, which is hereby incorporated by reference herein in its entirety.

FIELD OF THE INVENTION

The present disclosure relates generally to novel hydrazinyl lipidoids. The present disclosure also relates generally to methods of preparing such hydrazinyl lipidoids, their formulation with one or more active agents, and the delivery of such formulations to target organisms.

BACKGROUND OF THE INVENTION

A wide range of molecules have been employed for delivering polynucleotides and other active agents to cells. For example, polymers such as polyethylenimine or poly(beta-aminoesters) have been used to effectively complex DNA for delivery into cells. Polymers in these classes of delivery agent typically contain amine functionalities that serve to electrostatically bind to DNA to form nanoparticles that are then taken up by the cell via endocytosis. Once in the cell, these amine groups serve to buffer the endosome and cause an influx of ions due to the proton-sponge mechanism. The resulting burst of the endocytic vesicle leads to the release of the payload of the particle, which is then free to travel to the nucleus where the DNA is expressed.

While such polymer based systems have been used extensively for DNA delivery, the delivery of other molecules, such as RNA, presents distinct challenges. In many cases, polymeric materials do not work as effectively for RNA delivery. This is likely due to differences in the chemical structure of the RNA being delivered compared to DNA. RNA are generally short, linear fragments containing additional hydroxyl moieties on each ribose ring. These differences necessitate an alternative approach that is suited for complexation with short RNA strands. In particular, an improved delivery system is required for the use of siRNA for agricultural and pharmaceutical applications. The delivery system needs to protect siRNA from nuclease degradation, allow for the proper concentration and distribution profile in the target tissues, facilitate efficient uptake of siRNA into target cells, and release siRNA into cytoplasm to knockout expression of the target gene.

Promising results have been achieved with materials that form liposomes or lipoplexes that entrap the RNA or form nanoparticles, which can then be internalized by a cell. The materials utilized to form a lipid-based delivery system generally consist of a positively charged headgroup and a hydrophobic tail. The charged portion serves to electrostatically bind the negatively charged RNA, while the hydrophobic tail leads to self-assembly into lipophilic particles. Such cationic lipids are promising but still fall short of the transfection efficiency achieved by viral vectors. Few advances have been made in the field, in part due to the limited structural diversity of these lipid-like molecules, which is a result of the difficult synthetic procedures oftentimes required to access these structures.

Thus, there exists a continuing need for lipidoid molecules that possess an improved ability to deliver RNA, as well as other active agents, to cells over existing amine-containing lipidoid materials.

EMBODIMENTS OF THE INVENTION

One embodiment of the present invention is a hydrazinylalcohol lipidoid of formula (I):

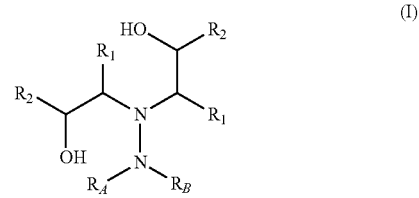

wherein:

$R_1$ is, independently, hydrogen, an optionally substituted $C_{1-20}$ aliphatic group, or an optionally substituted $C_{1-20}$ heteroaliphatic group;

$R_2$ is, independently, an optionally substituted $C_{1-20}$ aliphatic group or an optionally substituted $C_{1-20}$ heteroaliphatic group;

$R_A$ is hydrogen, an optionally substituted $C_{1-20}$ aliphatic group, an optionally substituted, $C_{1-20}$ heteroaliphatic group, or a group of formula (II):

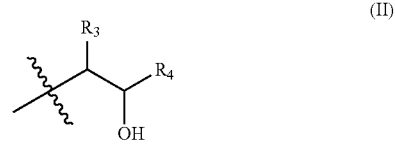

wherein $R_3$ is, independently, hydrogen, an optionally substituted $C_{1-20}$ aliphatic group, or an optionally substituted $C_{1-20}$ heteroaliphatic; and $R_4$ is, independently, an optionally substituted $C_{1-20}$ aliphatic group or an optionally substituted $C_{1-20}$ heteroaliphatic group;

$R_B$ is an optionally substituted aryl group, an optionally substituted heteroaryl group, or a group of formula (II):

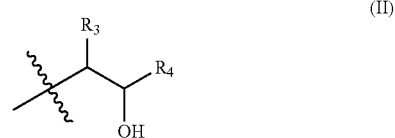

wherein $R_3$ and $R_4$ are as defined above;

wherein any one or more of $R_1$, $R_2$, $R_3$, and $R_4$ together with another $R_1$, $R_2$, $R_3$, or $R_4$ or one of $R_A$ and $R_B$ optionally defines a carbocyclic or heterocyclic ring system; and $R_A$ and $R_B$ together optionally define a carbocyclic or heterocyclic ring system.

Another embodiment of the present invention is the above compound, wherein $R_A$ and $R_B$ are each a group of formula (II):

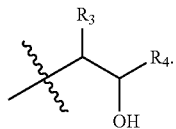
(II)

Another embodiment of the present invention is the above compound, wherein $R_1$ and $R_3$ are identical and $R_2$ and $R_4$ are identical.

Another embodiment of the present invention is the above compound, wherein $R_1$ and $R_3$ are hydrogen and $R_2$ and $R_4$ are an unbranched $C_{1-20}$ aliphatic group.

Another embodiment of the present invention is the above compound, wherein $R_2$ and $R_4$ are selected from the group consisting of methyl, n-butyl, n-pentyl, n-decanyl, and n-dodecanyl.

Another embodiment of the present invention is the above compound, wherein $R_1$ and $R_3$ are identical and $R_2$ and $R_4$ are different.

Another embodiment of the present invention is the above compound, wherein $R_1$ and $R_3$ are identical and $R_2$ and $R_4$ are different and wherein $R_1$ and $R_3$ are hydrogen and $R_2$ and $R_4$ are an unbranched $C_{1-20}$ aliphatic group.

Another embodiment of the present invention is the above compound, wherein $R_A$ is hydrogen, methyl, or hydroxyethyl.

Another embodiment of the present invention is the above compound, wherein $R_B$ is phenyl.

Another embodiment of the present invention is the above compound, wherein $R_1$ is hydrogen and $R_2$ is methyl.

Another embodiment of the present invention is the above compound, wherein $R_B$ is a group of formula (II):

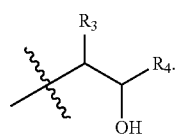
(II)

Another embodiment of the present invention is the above compound, wherein $R_1$ and $R_3$ are identical and $R_2$ and $R_4$ are identical.

Another embodiment of the present invention is the above compound, wherein $R_1$ and $R_3$ are hydrogen and $R_2$ and $R_4$ are an unbranched $C_{1-20}$ aliphatic group.

Another embodiment of the present invention is the above compound, wherein $R_2$ and $R_4$ are selected from the group consisting of methyl, n-butyl, n-pentyl, n-decanyl, and n-dodecanyl.

Yet another embodiment of the present invention is a compound selected from the group consisting of compounds of formulae (1), (2), (3), (4), (5), (6), (7), (8), (9), (10), and (11):

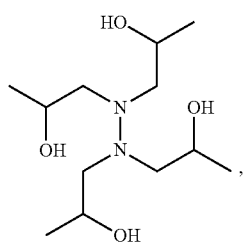
(1)

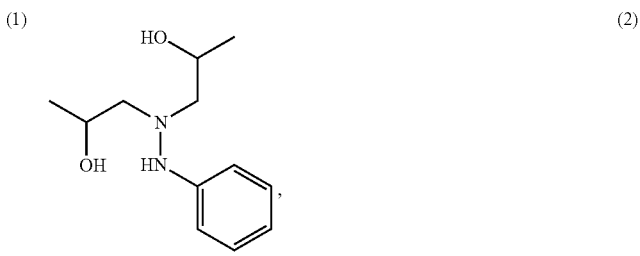
(2)

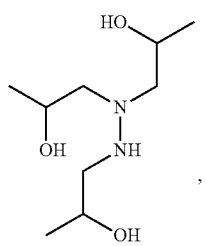
(3)

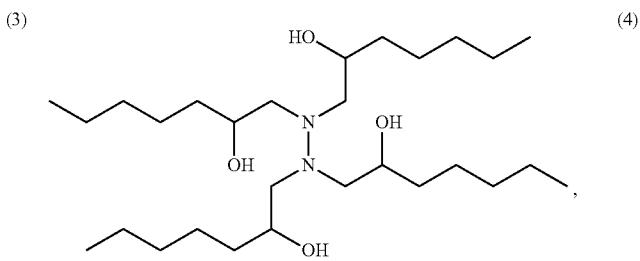
(4)

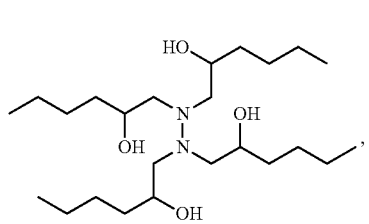
(5)

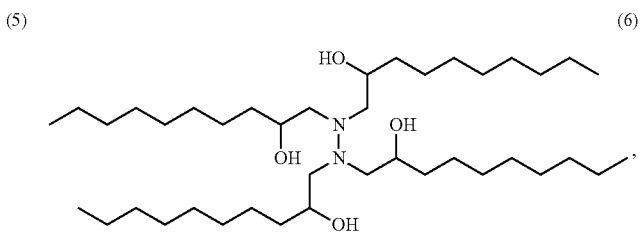
(6)

-continued

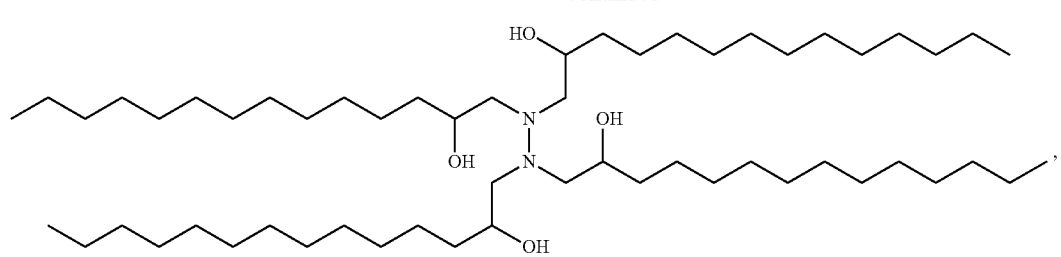

(7)

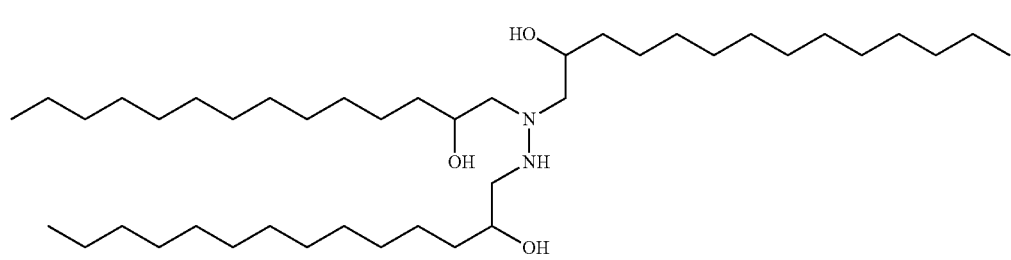

(8)

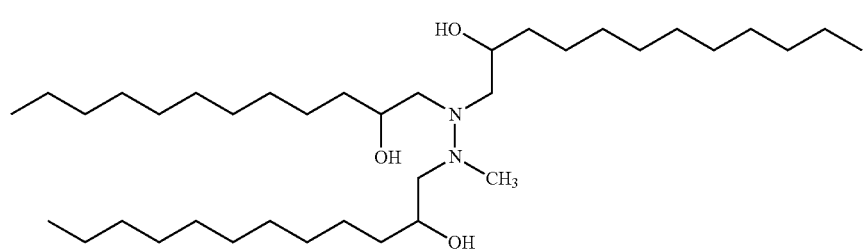

(9)

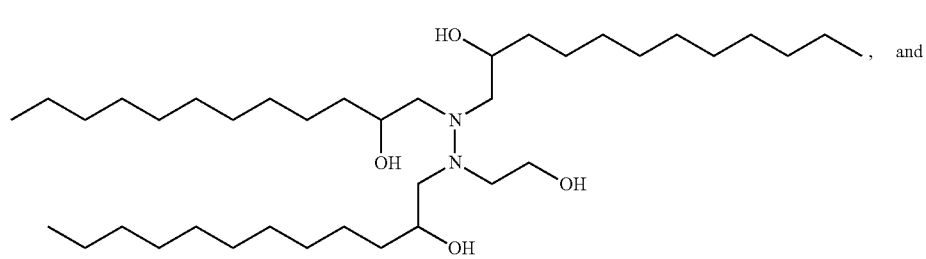

, and (10)

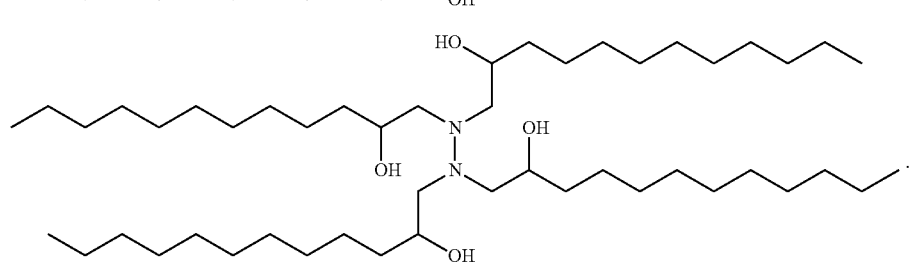

(11)

Yet another embodiment of the present invention is a microparticle comprising the above compound and an active agent to be delivered.

Another embodiment of the present invention is the above microparticle, wherein the active agent to be delivered is selected from the group consisting of polynucleotides, oligonucelotides, proteins, peptides, and small molecules.

Another embodiment of the present invention is the above microparticle, wherein the active agent to be delivered is an oligonucleotide or a polynucleotide.

Another embodiment of the present invention is the above microparticle, wherein the active agent to be delivered is an RNA.

Yet another embodiment of the present invention is a nanoparticle comprising the compound and an active agent to be delivered.

Another embodiment of the present invention is the above nanoparticle, wherein the active agent to be delivered is selected from the group consisting of polynucleotides, oligonucelotides, proteins, peptides, and small molecules.

Another embodiment of the present invention is the above nanoparticle, wherein the active agent to be delivered is an oligonucleotide or a polynucleotide.

Another embodiment of the present invention is the above nanoparticle, wherein the active agent to be delivered is an RNA.

Another embodiment of the present invention is the above nanoparticle, wherein the RNA is a small interfering RNA (siRNA) or a double-stranded RNA (dsRNA).

Yet another embodiment of the present invention is a method of delivering an active agent comprising the step of administering an effective amount of the above microparticle or nanoparticle to a plant, insect, or mammal.

Another embodiment of the present invention is the above method, wherein the active agent to be delivered is an oligonucleotide or a polynucleotide.

Another embodiment of the present invention is the above method, wherein the active agent to be delivered is an RNA.

Yet another embodiment of the present invention is a formulation comprising the above compound and an active agent to be delivered.

Another embodiment of the present invention is the above formulation, wherein the active agent to be delivered is an oligonucleotide or a polynucleotide.

Yet another embodiment of the present invention is a herbicidal formulation comprising the above compound, an herbicidal agent to be delivered, and an agriculturally acceptable carrier.

Yet another embodiment of the present invention is an insecticidal formulation comprising the above compound, an insecticidal agent to be delivered, and an agriculturally acceptable carrier.

Yet another embodiment of the present invention is a formulation for controlling a plant pathogen, comprising the above compound, an agent to be delivered that controls a plant pathogen, and an agriculturally acceptable carrier.

Yet another embodiment of the present invention is a pharmaceutical formulation comprising the above compound, a therapeutic agent to be delivered, and a pharmaceutically acceptable excipient and/or carrier.

Yet another embodiment of the present invention is a method of regulating expression of a gene in an organism, comprising applying the above formulation comprising the above compound and an active agent to be delivered to the organism.

Another embodiment of the present invention is the above method of regulating expression of a gene in an organism, wherein the organism is a plant, insect, or mammal.

Yet another embodiment of the present invention is a method of controlling a weed, comprising delivering to the weed an effective amount of the above herbicidal formulation.

Yet another embodiment of the present invention is a method of controlling an insect, comprising delivering to the insect an effective amount of the above insecticidal formulation.

Yet another embodiment of the present invention is a method of controlling a plant pathogen, comprising applying the above formulation for controlling a plant pathogen to the plant pathogen, or to a plant infected with the plant pathogen.

Yet another embodiment of the present invention is a method of treating a disorder in a human comprising administering to a human in need of such treatment a therapeutically effective amount of the above pharmaceutical formulation.

Yet another embodiment of the present invention is a plant cell, insect cell, or mammalian cell comprising the above compound.

DETAILED DESCRIPTION OF THE INVENTION

The novel hydrazinyl lipidoids of the present disclosure provide for several different advantages in the delivery of active agents to target organisms. For example, the hydrazine-containing portion of these lipidoids may be used to complex oligonucleotides and polynucleotides, thereby enhancing their delivery to the target organism and preventing their degradation. These hydrazinyl lipidoids may also be used generate formulations, such as microparticles, nanoparticles, picoparticles, liposomes, and micelles, containing the active agent to be delivered. These hydrazinyl lipidoids, as well as the formulations thereof, may be biocompatible and biodegradable and may be used to provide controlled, sustained release of the active agent to be delivered. These hydrazinyl lipidoids and their corresponding formulations may also be responsive to pH changes given that these lipidoids are protonated at lower pH. These hydrazinyl lipidoids may also act as proton sponges in the delivery of an active agent to a cell to cause endosome lysis.

Hydrazinyl Lipidoids

In one aspect, the present disclosure provides for novel hydrazinylalcohol lipidoids of formula (I):

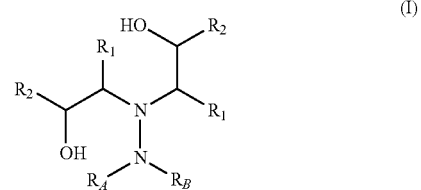

wherein:

$R_1$ is, independently, hydrogen, an optionally substituted aliphatic group, or an optionally substituted heteroaliphatic group;

$R_2$ is, independently, an optionally substituted aliphatic group or an optionally substituted heteroaliphatic group;

$R_A$ is hydrogen, an optionally substituted aliphatic group, an optionally substituted, heteroaliphatic group, or a group of formula (II):

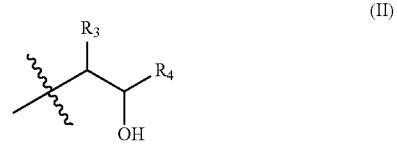

wherein $R_3$ is, independently, hydrogen, an optionally substituted aliphatic group, or an optionally substituted heteroaliphatic group; and $R_4$ is, independently, an optionally substituted aliphatic group or an optionally substituted heteroaliphatic group;

$R_B$ is an optionally substituted aryl group, an optionally substituted heteroaryl group, or a group of formula (II):

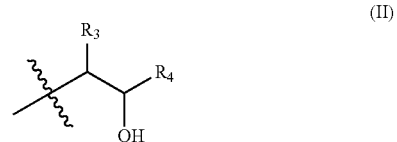

wherein $R_3$ and $R_4$ are as defined above;

wherein any one or more of $R_1$, $R_2$, $R_3$, and $R_4$ together with another $R_1$, $R_2$, $R_3$, or $R_4$ or one of $R_A$ and $R_B$ optionally defines a carbocyclic or heterocyclic ring system; and $R_A$ and $R_B$ together optionally define a carbocyclic or heterocyclic ring system.

In certain embodiments, $R_A$ and $R_B$ of the hydrazinylalcohol lipidoids of formula (I) can each be a group of formula (II):

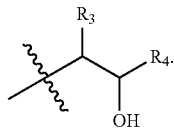
(II)

Therefore, the present disclosure provides for hydrazinylalcohol lipidoids of formula (III):

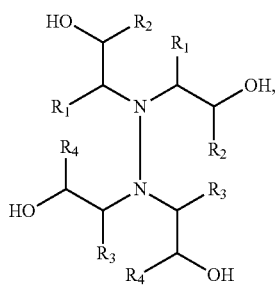
(III)

wherein
- $R_1$ and $R_3$ are, independently, hydrogen, an optionally substituted aliphatic group, or an optionally substituted heteroaliphatic group;
- $R_2$ and $R_4$ are, independently, an optionally substituted aliphatic group or an optionally substituted heteroaliphatic group; and
- wherein any one or more of $R_1$, $R_2$, $R_3$, and $R_4$ together with another $R_1$, $R_2$, $R_3$, or $R_4$ optionally defines a carbocyclic or heterocyclic ring system.

Any one of $R_1$, $R_2$, $R_3$, and $R_4$ of the presently disclosed hydrazinylalcohol lipidoids can be identical or different to the others. In certain embodiments, $R_1$ and $R_3$ are identical, but are different from $R_2$ and $R_4$, which are, in turn, identical to each other. In other embodiments, $R_1$ and $R_3$ are identical, but are different from $R_2$ and $R_4$, which are, in turn, different from each other. For example, $R_1$ and $R_3$ can each be hydrogen, while $R_2$ and $R_4$, identically or differently, can each be an unbranched $C_{1-20}$ aliphatic group. Therefore, the present disclosure provides for hydrazinylalcohol lipidoids of formula (IV):

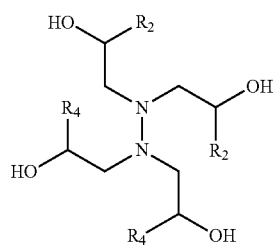
(IV)

wherein
- $R_2$ is, independently, an optionally substituted aliphatic group or an optionally substituted heteroaliphatic group;
- $R_4$ is, independently, an optionally substituted aliphatic group or an optionally substituted heteroaliphatic group; and
- wherein any one or more of $R_2$ and $R_4$ together with another $R_2$ or $R_4$ optionally defines a carbocyclic or heterocyclic ring system.

In certain embodiments, $R_A$ of the hydrazinylalcohol lipidoids of formula (I) is hydrogen. Therefore, the present disclosure provides hydrazinylalcohol lipidoids of formulae (V) and (VI):

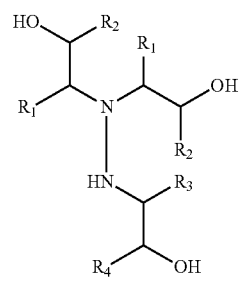
(V)

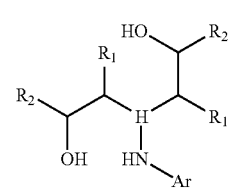
(VI)

wherein
- $R_1$ and $R_3$ are, independently, hydrogen, an optionally substituted aliphatic group, or an optionally substituted heteroaliphatic group;
- $R_2$ and $R_4$ are, independently, an optionally substituted aliphatic group or an optionally substituted heteroaliphatic group;
- Ar is an optionally substituted aryl group or an optionally substituted heteroaryl group; and
- wherein any one or more of $R_1$, $R_2$, $R_3$, and $R_4$ together with another $R_1$ or $R_2$ or an $R_3$, $R_4$ or Ar optionally defines a carbocyclic or heterocyclic ring system.

In certain embodiments, $R_A$ of the hydrazinylalcohol lipidoids of formula (I) is an optionally substituted aliphatic group. Therefore, the present disclosure provides hydrazinylalcohol lipidoids of formula (VII):

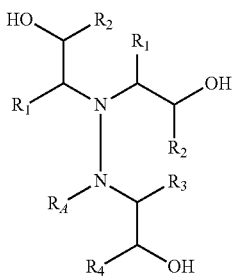
(VII)

wherein
- $R_1$ and $R_3$ are, independently, hydrogen, an optionally substituted aliphatic group, or an optionally substituted heteroaliphatic group;

R₂ and R₄ are, independently, an optionally substituted aliphatic group or an optionally substituted heteroaliphatic group;

R_A is an optionally substituted aliphatic group; and wherein any one or more of R₁, R₂, R₃, and R₄ together with another R₁ or R₂ or an R₃, R₄ or R_A optionally defines a carbocyclic or heterocyclic ring system.

In another aspect, the present disclosure provides for novel hydrazinyl lipidoids of formula (X):

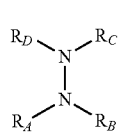
(X)

wherein
R_A is hydrogen, a group of formula (XI):

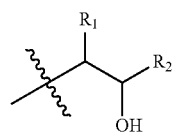
(XI)

wherein
R₁ is hydrogen, an optionally substituted aliphatic group, or an optionally substituted heteroaliphatic group; and
R₂ is an optionally substituted aliphatic group or an optionally substituted heteroaliphatic group;
or a group of formula (XII):

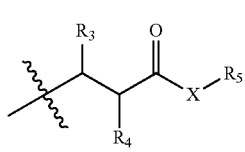
(XII)

wherein
R₃ and R₄ are, independently, hydrogen, an optionally substituted aliphatic group, or an optionally substituted heteroaliphatic group;
R₅ is an optionally substituted aliphatic group or an optionally substituted heteroaliphatic group; and
X is O or N;

R_B is hydrogen, an optionally substituted aliphatic group, an optionally substituted heteroaliphatic group, an optionally substituted aryl group, an optionally substituted heteroaryl group, an optionally substituted cycloalkyl group, an optionally substituted heterocycloalkyl group, a group of formula (X):

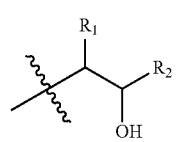
(XI)

wherein
R₁ and R₂ are as defined above;
or a group of formula (XI):

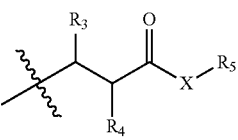
(XII)

wherein
R₃, R₄, R₅, and X are as defined above;
wherein R_A and R_B together with the nitrogen atom to which they are bonded also optionally define a heterocyclic ring system having the following formula:

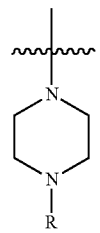

wherein R is an optionally substituted aliphatic group.
R_C is hydrogen, a group of formula (XI):

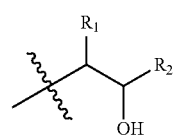
(XI)

wherein
R₁ and R₂ are as defined above;
a group of formula (XII):

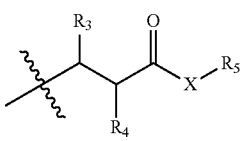
(XII)

wherein
R₃, R₄, R₅, and X are as defined above;
wherein R_A and R_C together with the nitrogen atoms to which they are bonded also optionally define a carbocyclic ring system having the following formula:

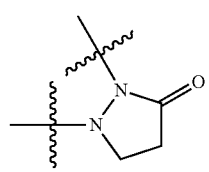 [SMILES: *N1CCC(=O)N1*]

wherein if $R_B$ is hydrogen, neither of $R_A$ and $R_C$ can also be hydrogen; and wherein $R_C$ can also be an optionally substituted aliphatic group or an optionally substituted heteroaliphatic group when $R_A$ is a group of formula (IX) or (X) and $R_B$ is hydrogen; and $R_D$ is a group of formula (XI):

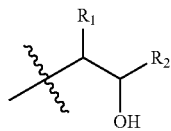

(XI)

wherein $R_1$ and $R_2$ are as defined above;

or a group of formula (XII):

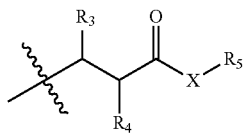

(XII)

wherein $R_3$, $R_4$, $R_5$, and X are as defined above.

In certain embodiments, $R_A$, $R_B$, $R_C$, and $R_D$ of the hydrazinyl lipidoids of formula (X) can each be, independently, groups of formulae (XI) or (XII). When each of $R_A$, $R_B$, $R_C$, and $R_D$ of the presently disclosed hydrazinyl lipidoids are groups of formulae (XI) or (XII), each can be identical or different to the others. In certain embodiments, $R_A$ and $R_B$ are identical, but are different from $R_C$ and $R_D$, which are, in turn, identical to each other. In other embodiments, $R_A$ and $R_B$ are identical, but are different from $R_C$ and $R_D$, which are, in turn, different from each other.

In certain embodiments, $R_A$, $R_C$, and $R_D$ of the hydrazinyl lipidoids of formula (X) can each be, independently, groups of formulae (XI) or (XII), while $R_B$ is hydrogen, an optionally substituted aliphatic group, such as methyl or 2-hydroxyethyl, an optionally substituted aryl group, such as phenyl, an optionally substituted group, such as 2-pyridyl, or an optionally substituted heterocycloalkyl group, such as optionally substituted 2,5-dihydro-1H-imidazole.

In certain embodiments, $R_C$, and $R_D$ of the hydrazinyl lipidoids of formula (X) can each be, independently, groups of formulae (XI) or (XII), while $R_A$ is hydrogen or an optionally substituted aryl group, such as phenyl, and $R_B$ is an optionally substituted aliphatic group, such as methyl, an optionally substituted aryl group, such as phenyl, and an optionally substituted group, such as 2-pyridyl.

In certain embodiments, $R_C$, and $R_D$ of the hydrazinyl lipidoids of formula (X) can each be, independently, groups of formulae (XI) or (XII), while $R_A$ is hydrogen and $R_B$ is an optionally substituted heterocycloalkyl group, such as optionally substituted 2,5-dihydro-1H-imidazole.

In certain embodiments, $R_D$ of the hydrazinyl lipidoids of formula (X) can be a group of formulae (XI) or (XII), while $R_B$ is an optionally substituted heterocycloalkyl group, such as optionally substituted 2,5-dihydro-1H-imidazole, and $R_A$ and $R_C$ are each hydrogen.

In certain embodiments, $R_A$ and $R_D$ of the hydrazinyl lipidoids of formula (X) can each be, independently, groups of formulae (XI) or (XII), while $R_C$ is hydrogen and $R_B$ is an optionally substituted aliphatic group, such as methyl or 2-hydroxyethyl.

In certain embodiments, $R_A$ and $R_C$ of the hydrazinyl lipidoids of formula (X), together with the nitrogen atoms to which they are bonded define a carbocyclic ring system having the following formula:

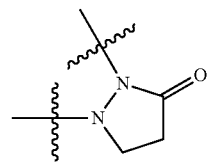 [SMILES: *N1CCC(=O)N1*]

while $R_B$ is an optionally substituted aliphatic group, such as methyl and 2-hydroxyethyl, an optionally substituted aryl group, such as phenyl, or a group of formulae (XI) or (XII) and $R_D$ is a group of formulae (XI) or (XII).

In certain embodiments, $R_A$ and $R_B$ of the hydrazinyl lipidoids of formula (X), together with the nitrogen atom to which they are bonded define a heterocyclic ring system having the following formula:

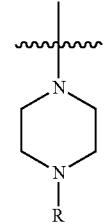

while $R_C$ is hydrogen or a group of formulae (XI) or (XII) and $R_D$ is a group of formulae (XI) or (XII).

In another aspect, the present disclosure provides for novel hydrazinyl lipidoids of formula (XIII):

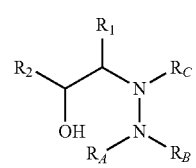

(XIII)

wherein:

$R_1$ is, independently, hydrogen, an optionally substituted aliphatic group, or an optionally substituted heteroaliphatic group;

$R_2$ is, independently, an optionally substituted alkyl group, an optionally substituted heteroalkyl group, an optionally substituted alkenyl group, or an optionally substituted heteroalkenyl group;

$R_4$ is hydrogen, an optionally substituted aliphatic group, an optionally substituted, heteroaliphatic group, or a group of formula (II):

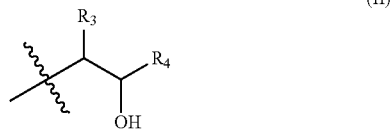
(II)

wherein
$R_3$ is, independently, hydrogen, an optionally substituted aliphatic group, or an optionally substituted heteroaliphatic group; and
$R_4$ is, independently, an optionally substituted alkyl group, an optionally substituted heteroalkyl group, an optionally substituted alkenyl group, or an optionally substituted heteroalkenyl group;
$R_B$ is hydrogen, an optionally substituted aliphatic group, an optionally substituted aryl group, an optionally substituted heteroaryl group, an optionally substituted heterocycloalkyl group, or a group of formula (II):

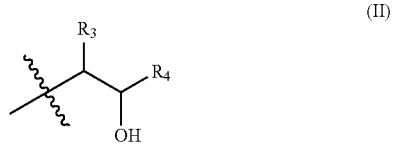
(II)

wherein $R_3$ and $R_4$ are as defined above;
$R_C$ is hydrogen or a group of formula (II):

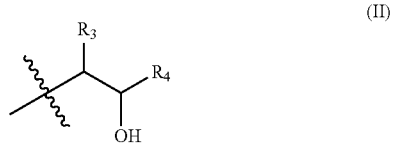
(II)

wherein $R_3$ and $R_4$ are as defined above;
wherein
any one or more of $R_1$, $R_2$, $R_3$, and $R_4$ together with another $R_1$, $R_2$, $R_3$, or $R_4$ or one of $R_A$ and $R_B$ optionally define a carbocyclic or heterocyclic ring system; and
$R_A$ and $R_B$ together optionally define a carbocyclic or heterocyclic ring system.

In certain embodiments, $R_A$ and $R_B$ of the hydrazinyl lipidoids of formula (XIII) can each be a group of formula (II). Any one of $R_1$, $R_2$, $R_3$, and $R_4$ of the presently disclosed hydrazinyl lipidoids of formula (XIII) can be identical or different to the others. In certain embodiments, $R_1$ and $R_3$ are identical, but are different from $R_2$ and $R_4$, which are, in turn, identical to each other. In other embodiments, $R_1$ and $R_3$ are identical, but are different from $R_2$ and $R_4$, which are, in turn, different from each other. For example, $R_1$ and $R_3$ can each be hydrogen, while $R_2$ and $R_4$, identically or differently, can each be an unbranched $C_{1-20}$ aliphatic group.

In certain embodiments, $R_A$ of the hydrazinyl lipidoids of formula (XIII) is hydrogen, while $R_B$ is an optionally substituted aliphatic group, such as methyl or 2-hydroxyethyl, an optionally substituted aryl group, such as phenyl, an optionally substituted heteroaryl group, such as 2-pyridyl, an optionally substituted heterocycloaliphatic group, such as optionally substituted 2,5-dihydro-1H-imidazole, or a group of formula (II). In certain embodiments, $R_A$ of the hydrazinyl lipidoids of formula (XIII) is an optionally substituted aliphatic group, such as methyl or 2-hydroxyethyl, while $R_B$ is a group of formula (II). In certain embodiments, $R_A$ of the hydrazinyl lipidoids of formula (XIII) is group of formula (II), while $R_B$ is an optionally substituted aryl group, such as phenyl, an optionally substituted heteroaryl group, such as 2-pyridyl, or an optionally substituted heterocycloaliphatic group, such as optionally substituted 2,5-dihydro-1H-imidazole, or a group of formula (II).

In certain embodiments, each of $R_2$ and $R_4$ of the hydrazinyl lipidoids of formula (XIII) is an alkyl group. In certain embodiments, each of $R_2$ and $R_4$ of the hydrazinyl lipidoids of formula (XIII) is an alkylene group. In certain embodiments, each of $R_2$ and $R_4$ of the hydrazinyl lipidoids of formula (XIII) is an alkylene group having one double bond. In certain embodiments, each of $R_2$ and $R_4$ of the hydrazinyl lipidoids of formula (XIII) is an alkylene group having two double bonds.

In another aspect, the present disclosure provides for novel hydrazinyl lipidoids of formula (XIV):

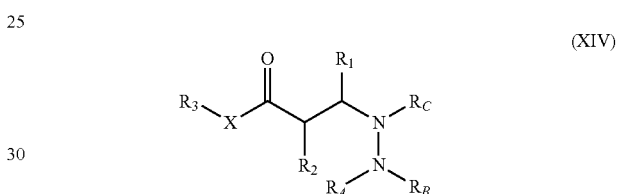
(XIV)

wherein:
$R_1$ and $R_2$ are, independently, hydrogen, an optionally substituted aliphatic group, or an optionally substituted heteroaliphatic group;
$R_3$ is, independently, an optionally substituted aliphatic group or an optionally substituted heteroaliphatic group; and
X is O or N; and
$R_A$ is hydrogen, an optionally substituted aliphatic group, an optionally substituted, heteroaliphatic group, or a group of formula (XV):

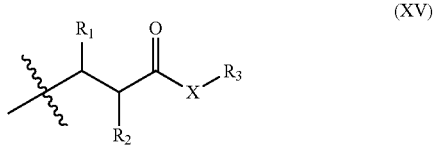
(XV)

wherein $R_1$, $R_2$, and $R_3$ are as defined above;
$R_B$ is an optionally substituted aryl group, an optionally substituted heteroaryl group, or a group of formula (XV):

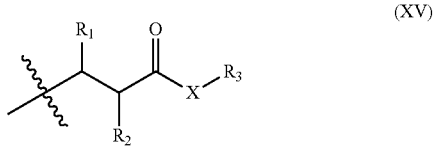
(XV)

wherein $R_1$, $R_2$, and $R_3$ are as defined above; and $R_C$ is H, an optionally substituted aliphatic group, or a group of formula (XV):

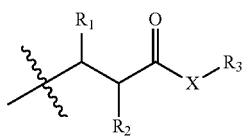
(XV)

wherein $R_1$, $R_2$, and $R_3$ are as defined above;
wherein
any one or more of $R_1$, $R_2$, $R_3$, and $R_C$ together with another $R_1$, $R_2$, or $R_3$, or one of $R_A$ and $R_B$ optionally defines a carbocyclic or heterocyclic ring system; and
$R_A$ and $R_B$ together optionally define a carbocyclic or heterocyclic ring system.

In certain embodiments, $R_A$, $R_B$, and $R_C$ of the hydrazinyl lipidoids of formula (XIV) can each be a group of formula (XV). When each of $R_A$, $R_B$, and $R_C$ of the presently disclosed hydrazinyl lipidoids of formula (XIV) are a group of formula (XV), each can be identical or different to the others. In certain embodiments, $R_A$ and $R_B$ are identical, but are different from $R_C$. In certain embodiments, $R_A$ and $R_C$ are identical, but are different from $R_B$. In certain embodiments, $R_B$ and $R_C$ are identical, but are different from $R_A$.

In certain embodiments, $R_A$ of the hydrazinyl lipidoids of formula (XIV) is hydrogen, $R_B$ is an optionally substituted aryl group, such as phenyl, an optionally substituted heteroaryl group, such as 2-pyridyl, or a group of formula (XV), and $R_C$ is an optionally substituted aliphatic group, such as methyl or 2-hydroxyethyl. In certain embodiments, $R_A$ of the hydrazinyl lipidoids of formula (XIV) is an optionally substituted aliphatic group, such as methyl or 2-hydroxy ethyl, $R_B$ is a group or formula (XV), and $R_C$ is hydrogen or a group of formula (XV). In certain embodiments, $R_A$ and $R_C$ of the hydrazinyl lipidoids of formula (XIV) is a group of formula (XV) and $R_B$ is an optionally substituted heteroaryl group, such as pyridyl or an optionally substituted heterocycloalkyl group, such as optionally substituted 2,5-dihydro-1H-imidazole.

In certain embodiments, $R_3$ of the hydrazinyl lipidoids of formula (XIV) is an alkyl group. In certain embodiments, $R_3$ of the hydrazinyl lipidoids of formula (XIV) is an alkylene group having one double bond. In certain embodiments, $R_3$ of the hydrazinyl lipidoids of formula (XIV) is an alkylene group having two double bonds.

In another aspect, the present disclosure provides for novel hydrazinyl lipidoids of formula (XVI):

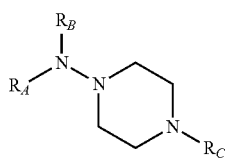
(XVI)

wherein
$R_A$ is a group of formula (XI):

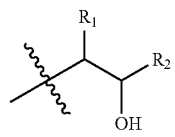
(XI)

wherein
$R_1$ is, independently, hydrogen, an optionally substituted aliphatic group, or an optionally substituted heteroaliphatic group;
$R_2$ is, independently, an optionally substituted aliphatic group or an optionally substituted heteroaliphatic group;
or a group of formula (XV):

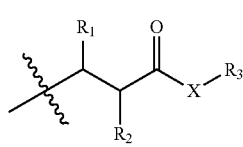
(XV)

wherein
$R_1$ and $R_2$ are, independently, hydrogen, an optionally substituted aliphatic group, or an optionally substituted heteroaliphatic group;
$R_3$ is, independently, an optionally substituted aliphatic group or an optionally substituted heteroaliphatic group; and
X is O or N;
$R_B$ is hydrogen, a group of formula (XI):

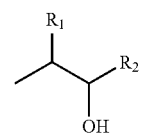
(XI)

wherein $R_1$ and $R_2$ are as defined above;
or a group of formula (XV):

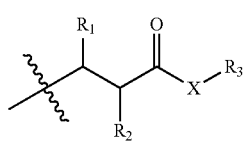
(XV)

wherein
$R_1$, $R_2$, $R_3$, and X are as defined above; and
$R_C$ is an optionally substituted aliphatic group, or an optionally substituted heteroaliphatic group.

In certain embodiments, $R_A$ and $R_B$ of the hydrazinyl lipidoids of formula (XVI) can each be a group of formula (XI) or (XV). When each of $R_A$ and $R_B$ of the presently disclosed hydrazinyl lipidoids of formula (XVI) are a group of formula (XI) or (XV), each can be identical or different to the others. In certain embodiments, $R_A$ and $R_B$ are identical. In certain embodiments, $R_A$ and $R_B$ are different.

In certain embodiments, $R_A$ of the hydrazinyl lipidoids of formula (XVI) is a group of formula (XI), $R_B$ is hydrogen or a group of formula (XI), and $R_C$ is an optionally substituted aliphatic group, such as methyl. In certain embodiments, $R_A$ of the hydrazinyl lipidoids of formula (XVI) is a group of formula (XV), $R_B$ is hydrogen or a group of formula (XV), and $R_C$ is an optionally substituted aliphatic group, such as methyl.

In certain embodiments, each of $R_2$ and $R_3$ of the hydrazinyl lipidoids of formula (XVI) is an alkyl group. In certain embodiments, each of $R_2$ and $R_3$ of the hydrazinyl lipidoids of formula (XVI) is an alkylene group. In certain embodiments, each of $R_2$ and $R_3$ of the hydrazinyl lipidoids of formula (XVI) is an alkylene group having one double bond. In certain embodiments, each of $R_2$ and $R_3$ of the hydrazinyl lipidoids of formula (XVI) is an alkylene group having two double bonds.

In another aspect, the present disclosure provides for novel hydrazinyl lipidoids of formula (XVII):

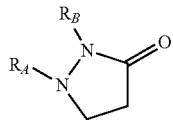

(XVII)

wherein:
$R_A$ and $R_B$ are, independently, an optionally substituted aliphatic group, an optionally substituted heteroaliphatic group, an optionally substituted aryl group, an optionally substituted heteroaryl group, or a group of formula (XIV):

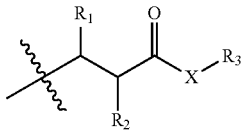

(XV)

wherein
$R_1$ and $R_2$ are, independently, hydrogen, an optionally substituted aliphatic group, or an optionally substituted heteroaliphatic group;
$R_3$ is, independently, an optionally substituted aliphatic group or an optionally substituted heteroaliphatic group; and
X is O or N; and
wherein at least one of $R_A$ and $R_B$ is group of formula (XV).

In certain embodiments, $R_A$ and $R_B$ of the hydrazinyl lipidoids of formula (XVII) can each be a group of formula (XV). When each of $R_A$ and $R_B$ of the presently disclosed hydrazinyl lipidoids of formula (XVII) are a group of formula (XV), each can be identical or different to the others. In certain embodiments, $R_A$ and $R_B$ are identical. In certain embodiments, $R_A$ and $R_B$ are different.

In certain embodiments, $R_A$ of the hydrazinyl lipidoids of formula (XVII) is a group of formula (XV) and $R_B$ is an optionally substituted aliphatic group, such as methyl or 2-hydroxyethyl, an optionally substituted aryl group, such as phenyl, or a group of formula (XV). In certain embodiments, $R_A$ of the hydrazinyl lipidoids of formula (XVII) is an optionally substituted aliphatic group, such as methyl or 2-hydroxyethyl, and $R_B$ is a group of formula (XV).

In certain embodiments, $R_3$ of the hydrazinyl lipidoids of formula (XVII) is an alkyl group. In certain embodiments, $R_3$ of the hydrazinyl lipidoids of formula (XVII) is an alkylene group having one double bond. In certain embodiments, $R_3$ of the hydrazinyl lipidoids of formula (XVII) is an alkylene group having two double bonds.

The aliphatic groups of the presently disclosed hydrazinyl and hydrazinylalcohol lipidoids refers to both saturated and unsaturated aliphatic hydrocarbyl groups, which can be straight chain (i.e., unbranched), branched, or cyclic (including polycyclic) and are optionally substituted with one or more functional groups. Examples of aliphatic groups include, but are not limited to, alkyl, alkenyl, alkynyl, cycloalkyl, cycloalkenyl, and cycloalkynyl groups, each of which are optionally substituted with one or more functional groups. As used herein, the term "alkyl" refers to saturated hydrocarbyl groups, which can be unbranched, branched, or cyclic (i.e., alicyclic) alkyl groups. As used herein, the terms "alkenyl" and "alkylene" refers to unsaturated hydrocarbyl groups having at least one carbon-carbon double bond. As used herein, the term "alkynyl" refers to unsaturated hydrocarbyl groups having at least one carbon-carbon triple bond.

Examples of such aliphatic groups include, but are not limited to, methyl, ethyl, n-propyl, isopropyl, cyclopropyl, —CH$_2$-cyclopropyl, n-butyl, sec-butyl, isobutyl, tert-butyl, cyclobutyl, —CH$_2$-cyclobutyl, n-pentyl, sec-pentyl, isopentyl, tert-pentyl, neopentyl, cyclopentyl, —CH$_2$-cyclopentyl, hexyl, cyclohexyl, —CH$_2$-cyclohexyl, heptyl, cycloheptyl, octyl, nonyl, decyl, undecyl, dodecyl, tridecyl, tetradecyl, pentadecyl, hexadecyl, heptadecyl, octadecyl, nonadecyl, icosyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, and all isomers thereof.

The heteroaliphatic groups of the presently disclosed hydrazinyl and hydrazinylalcohol lipidoids refers to aliphatic groups, as described above, that independently in one or more instances contain an oxygen, sulfur, nitrogen, phosphorus, or silicon atom between two carbon atoms of the aliphatic group. Such heteroaliphatic groups include saturated and unsaturated heterocycles. As used herein, the term "heterocycles," refers to a non-aromatic partially unsaturated or fully saturated 3- to 10-membered ring system, which includes single rings of 3 to 8 atoms in size and bi- and tri-cyclic ring systems, which may include aromatic six-membered aryl or aromatic heterocyclic groups fused to a non-aromatic heterocyclic ring. Such heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. Examples of such heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, 2,5-dihydro-1H-imidazole, and tetrahydrofuryl.

In certain embodiments, the aliphatic and/or heteroaliphatic groups of the hydrazinyl and hydrazinylalcohol compounds of the present disclosure independently contain from 1 to 20, or from 1 to 12, or from 1 to 10, or from 1 to 8, or from 1 to 5, or from 1 to 4, or from 4 to 5, or from 4 to 8, or from 4 to 10, or from 4 to 12, or from 4 to 20, or from 5 to 20, or from 5 to 12, or from 5 to 10, or from 5 to 8, or from 8 to 10, or from 8 to 12, or from 8 to 20, or from 10 to 12, or from 10 to 20, or from 12 to 20 carbon atoms.

The aryl and heteroaryl groups of the presently disclosed hydrazinyl and hydrazinylalcohol lipidoids refer to mono- or polycyclic aromatic carbocyclic groups and mono- or polycyclic aromatic heterocyclic groups. In certain embodiments, these groups have 3-14 carbon atoms, each of which is optionally substituted. In certain embodiments, the aryl group is a mono- or bicyclic carbocyclic ring system having one or two aromatic rings. The term "carbocyclic" as used herein, refers to an aromatic or non-aromatic ring system in which each atom of the ring is a carbon atom. Examples of such aryl groups include, but are not limited to, phenyl, naphthyl, tetrahydronaphthyl, indanyl, and indenyl. In certain embodiments, the heteroaryl group is a mono- or bicyclic heterocyclic ring system having one or two aromatic rings. In certain embodiments, the heteroaryl group (1) has from five to ten ring atoms of which one ring atom is selected from S, O, and N, (2) has zero, one, or two ring atoms that are additional heteroatoms independently selected from S, O, and N, and (3) the remaining ring atoms are carbon. Examples of such heteroaryl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl.

It will be appreciated that the compounds of the presented disclosure may be substituted with any number of substituents. In general, the term "substituted," whether preceded by the term "optionally" or not, and substituents contained in formulas of the present disclosure, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. Broadly, permissible substituents include all acyclic and cyclic, branched and unbranched, carbocyclic and heterocyclic, aromatic and nonaromatic substituents of organic compounds. For purposes of this disclosure, heteroatoms, such as nitrogen, may have hydrogen substituents and/or any permissible substituents of organic compounds described herein which satisfy the valencies of the heteroatoms. Furthermore, the presently disclosed hydrazinyl lipidoids are not intended to be limited in any manner by the permissible substituents of organic compounds. Any substituents disclosed herein may also be further substituted (e.g., an aryl substituent may itself be substituted, such as with another aryl group, which, in turn, is further substituted with fluorine at one or more positions).

Examples of optional substituents of the compounds of the present disclosure include, but are not limited to, aliphatic groups, heteroaliphatic groups, aryl groups, heteroaryl groups, arylalkyl groups, heteroarylalkyl groups, alkoxy groups, aryloxy groups, heteroalkoxy groups, heteroaryloxy groups, alkylthio groups, arylthio groups, heteroalkylthio groups, heteroarylthio groups, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$R, —C(O)R, —CO$_2$(R), —CON(R)$_2$, —OC(O)R, —OCO$_2$R, —OCON(R)$_2$, —N(R)$_2$, —S(O)$_2$R, and —NR(CO)R, wherein each R is, independently, hydrogen, an aliphatic group, a heteroaliphatic group, an aryl group, a heteroaryl group, an arylalkyl group, or a heteroarylalkyl group, wherein any of the aliphatic, heteroaliphatic, arylalkyl, or heteroarylalkyl substituents described above and herein may be optionally substituted, branched or unbranched, cyclic or acyclic, and wherein any of the aryl or heteroaryl substituents described above and herein may be optionally substituted.

In certain embodiments, the presently disclosed hydrazinyl and hydrazinylalcohol lipidoids can be salt, either from protonation by a mineral or organic acid or by quaternization of one more available tertiary nitrogens. Examples of counterions for such salts include, but are not limited to, halides, such as fluoride, chloride, bromide, or iodide, nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, an acid anion such as acetate or formate, or anions with negative charges greater than −1 (e.g., having in some embodiments one or more than one adsorbent functional group as counterion), such as oxide, sulfide, nitride, arsenate, phosphate, arsenite, hydrogen phosphate, sulfate, thio sulfate, sulfite, carbonate, chromate, dichromate, peroxide, or oxalate.

In certain embodiments, the presently disclosed hydrazinyl and hydrazinylalcohol lipidoids, and optional substitutents thereon, can contain isotopes of various common atoms. Examples of such isotopes include, but are not limited to, deuterium, $C^{13}$, $N^{15}$, $O^{18}$, and $F^{18}$.

In certain embodiments, $R_1$, $R_2$, $R_3$, $R_4$, and $R_4$, independently, can be perfluorinated $C_{1-20}$ alkyl groups. In certain embodiments, $R_2$ and $R_4$ are identical and selected from the group consisting of methyl, n-butyl, n-pentyl, n-decanyl, and n-dodecanyl. In certain embodiments, $R_2$ is methyl and R4 is n-pentyl. In certain embodiments, $R_2$ is methyl and $R_4$ is n-octyl. In certain embodiments, $R_B$ is phenyl. In certain embodiments, $R_4$ is methyl or —CH$_2$CH$_2$OH.

In certain embodiments, the hydrazinyl and hydrazinylalcohol lipidoid compounds of the present disclosure is a compound selected from the group consisting of compounds 1 through 116, as shown below:

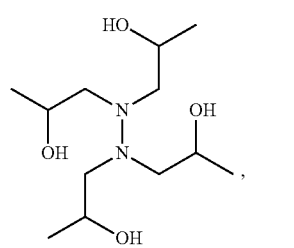

(1)

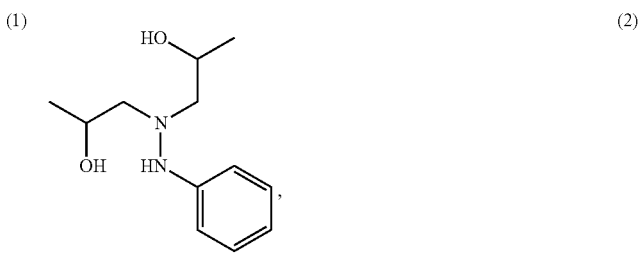

(2)

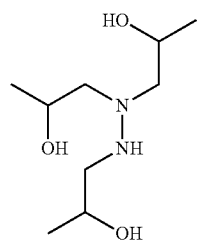
(3)
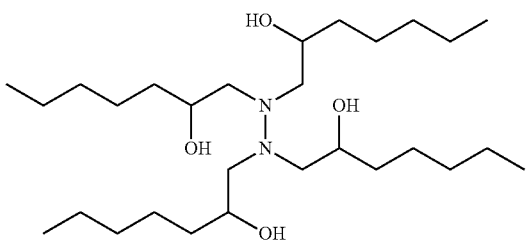
(4)
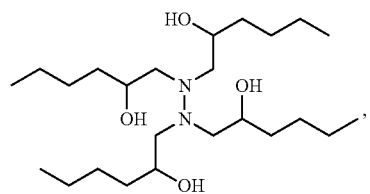
(5)
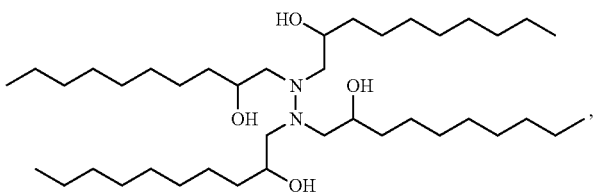
(6)
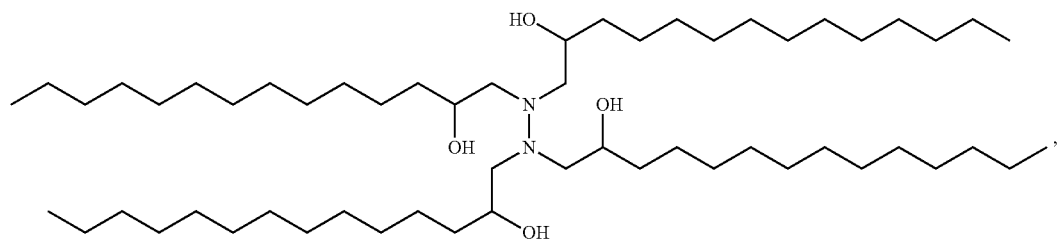
(7)
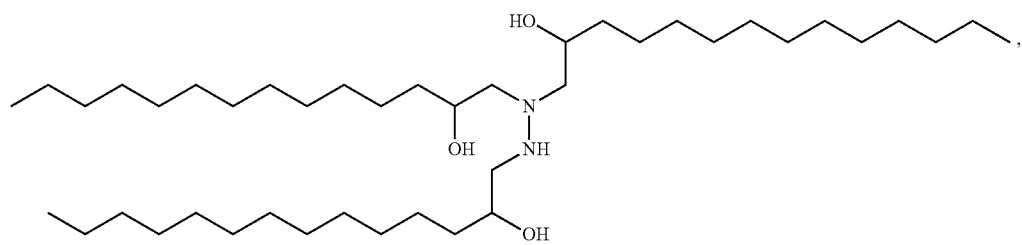
(8)
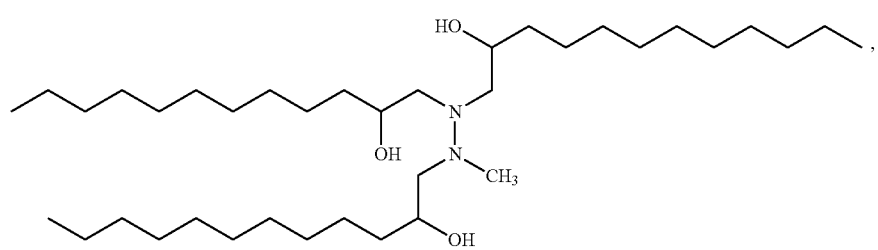
(9)
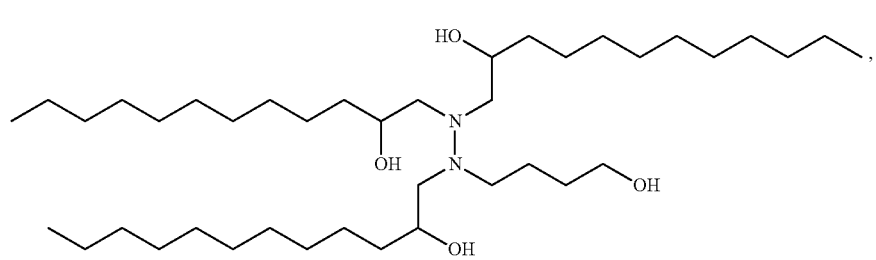
(10)

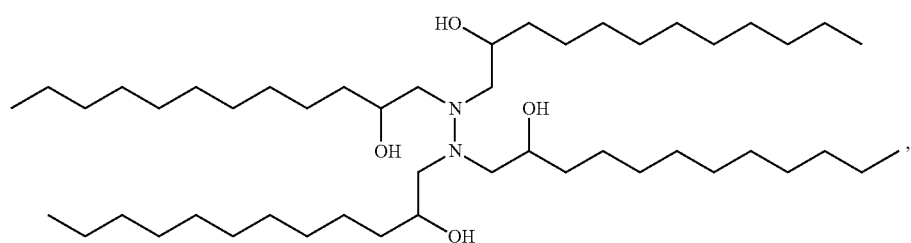
(11)
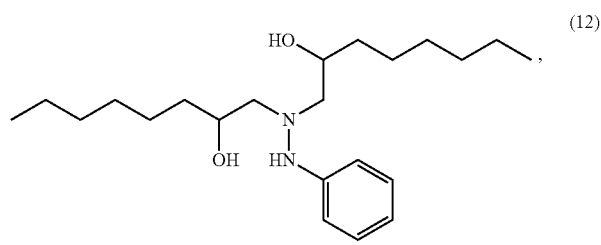
(12)
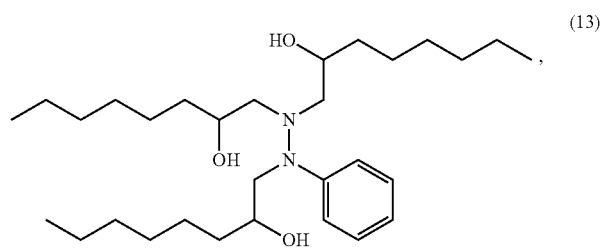
(13)
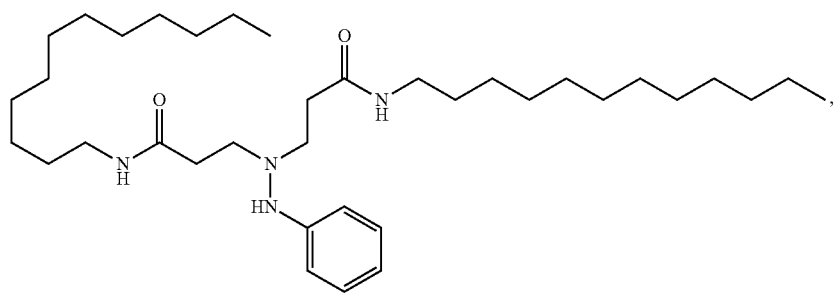
(14)
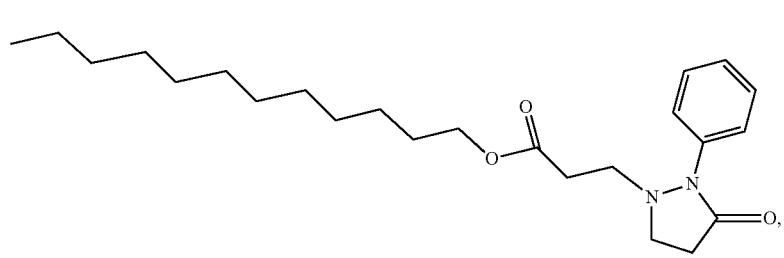
(15)
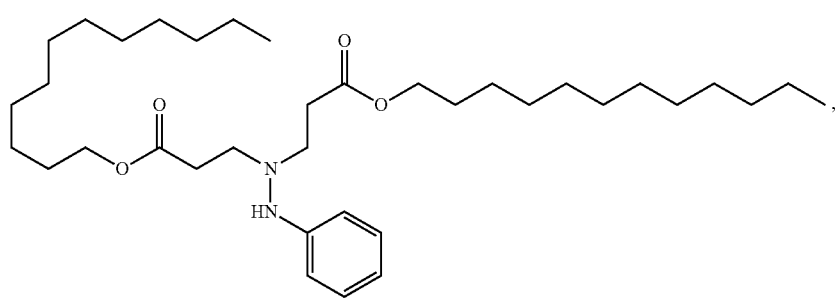
(16)

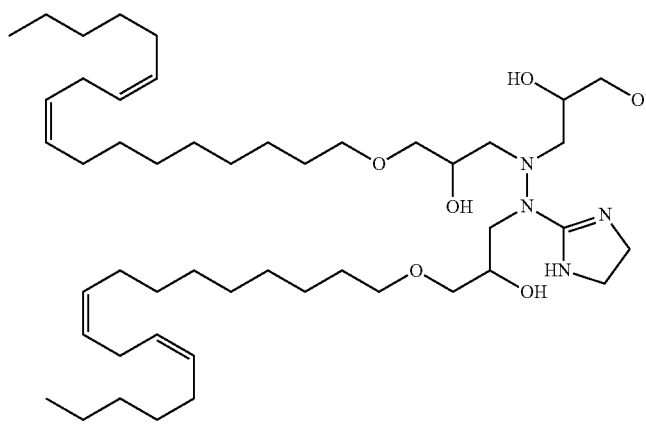
(17)
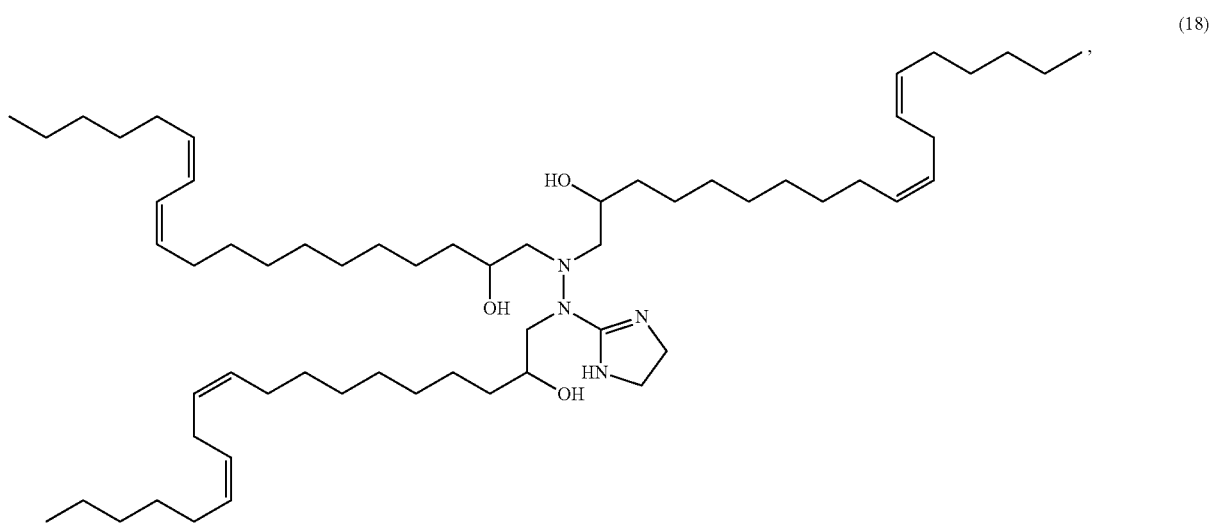
(18)
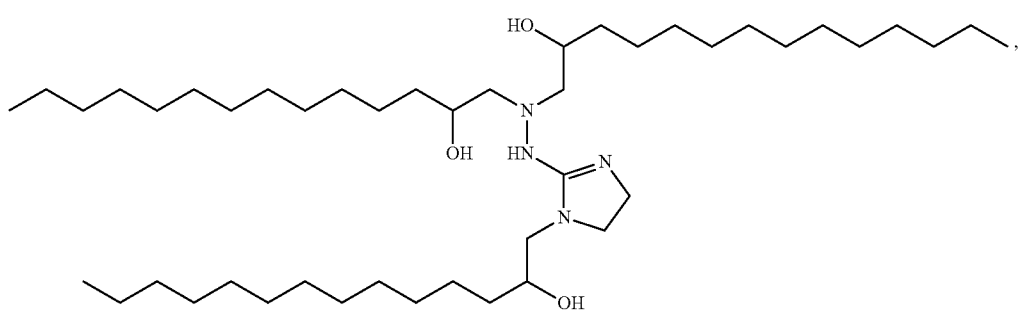
(19)
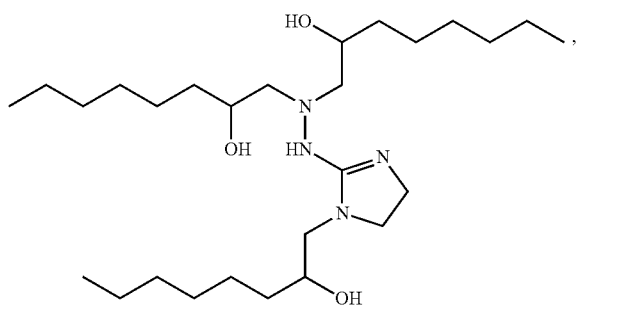
(20)

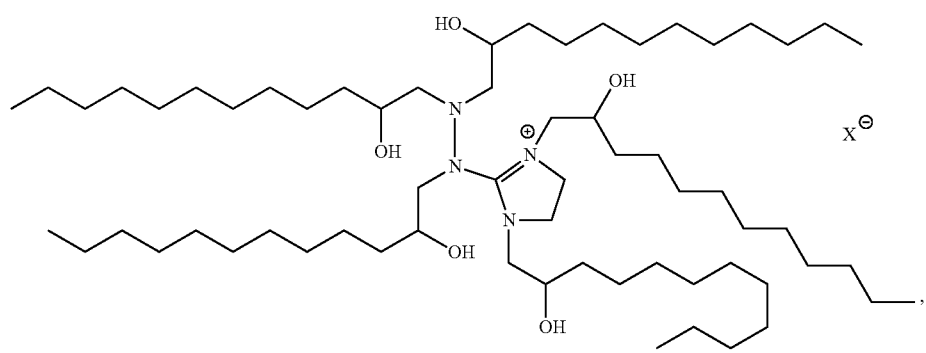
(21)
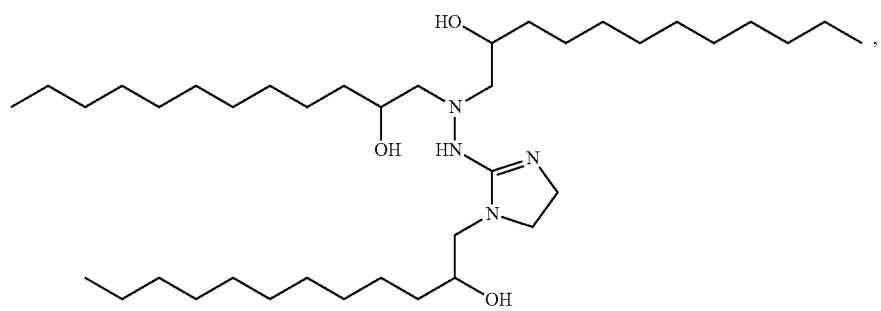
(22)
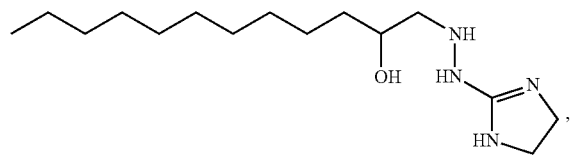
(23)
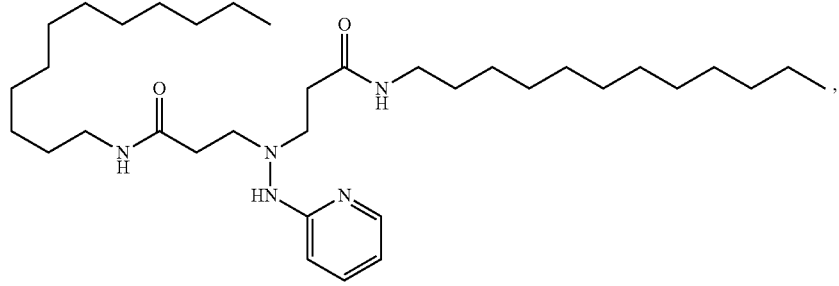
(24)
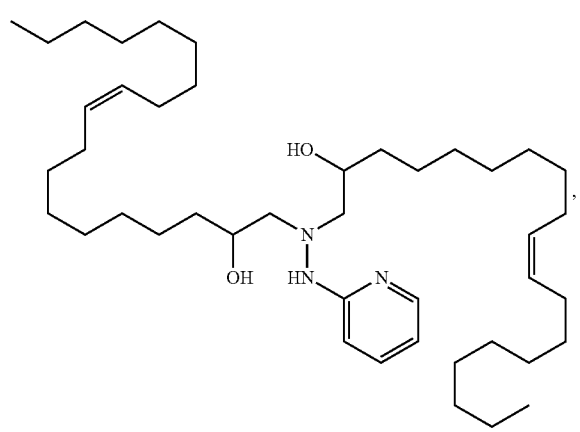
(25)
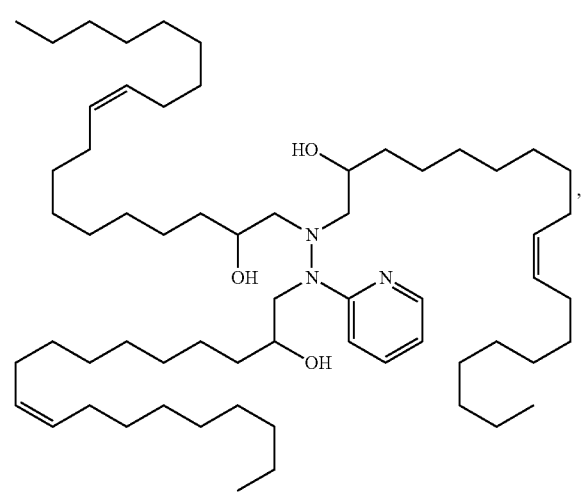
(26)

-continued
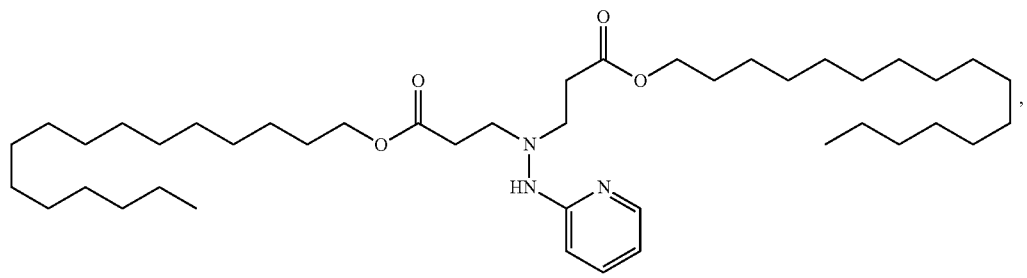
(27)
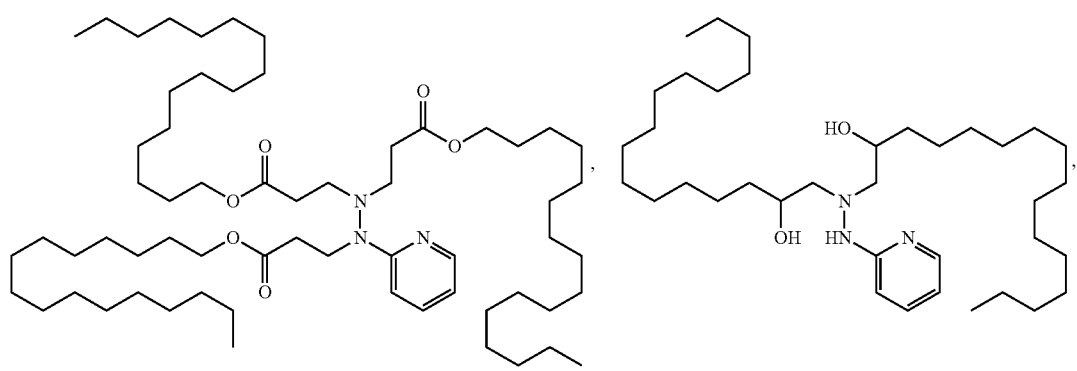
(28) (29)
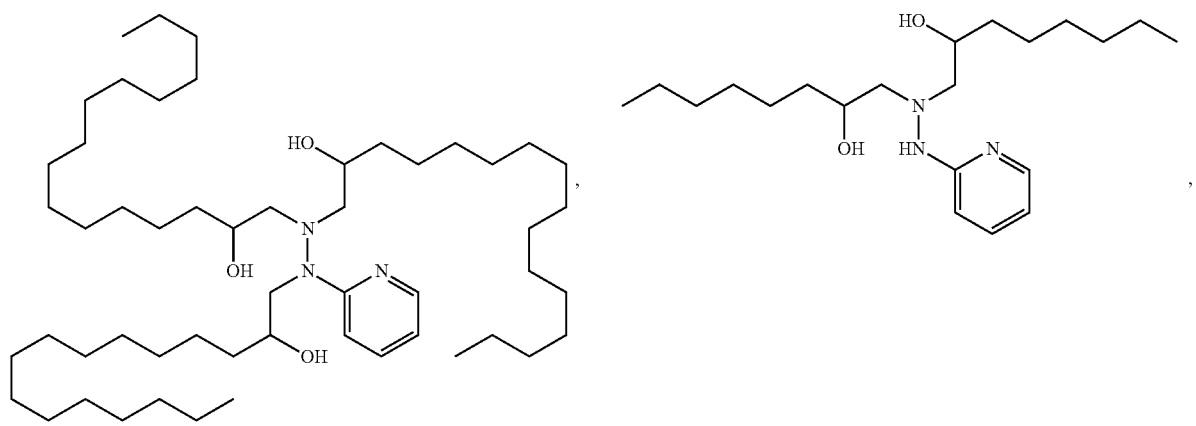
(30) (31)
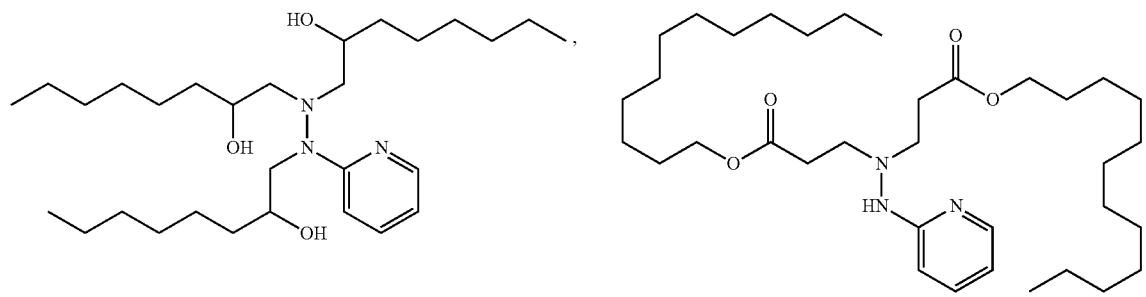
(32) (33)

(34)
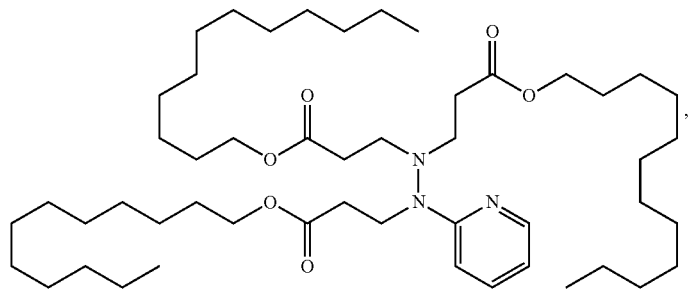
(35)
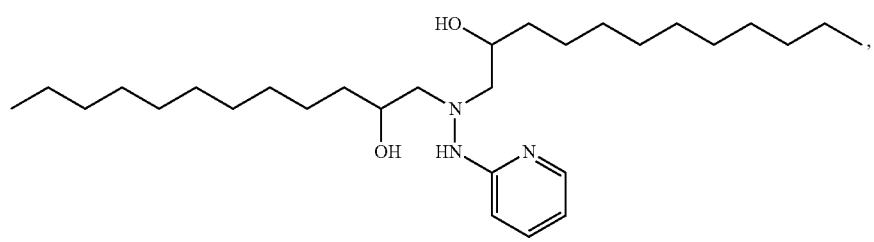
(36)
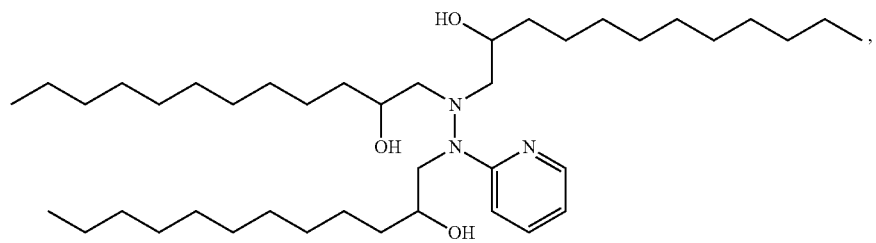
(37)
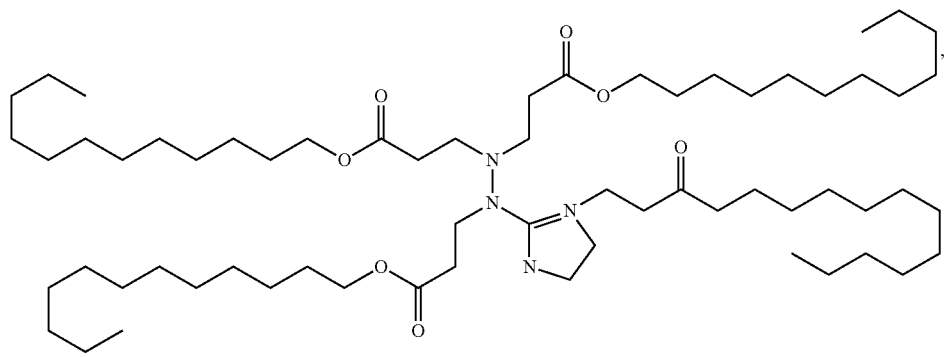
(38)
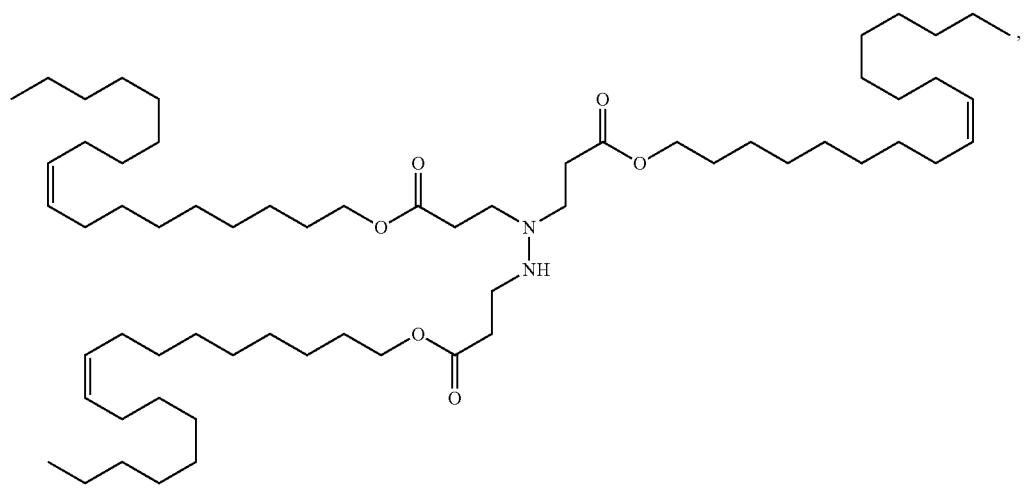

-continued
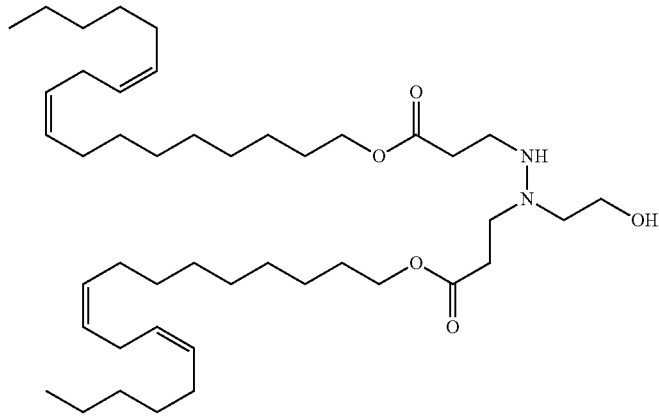
(39)
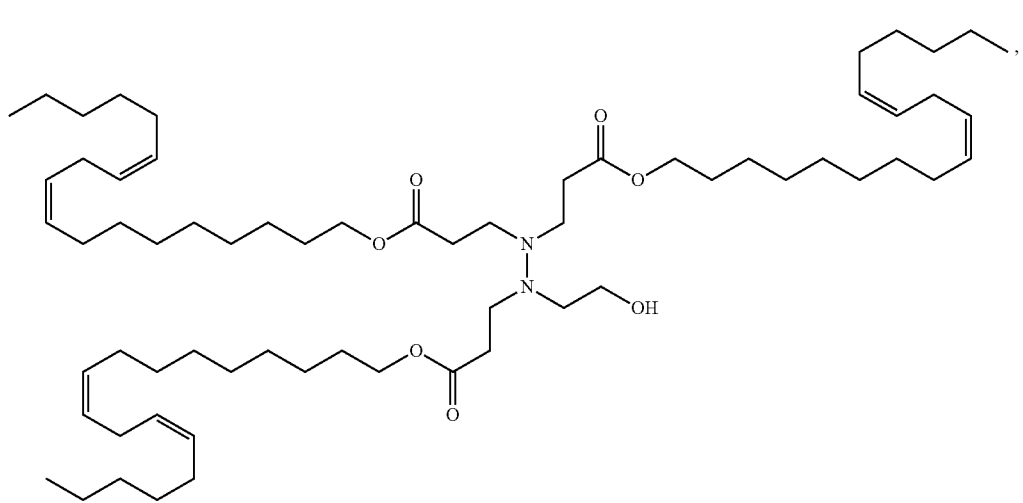
(40)
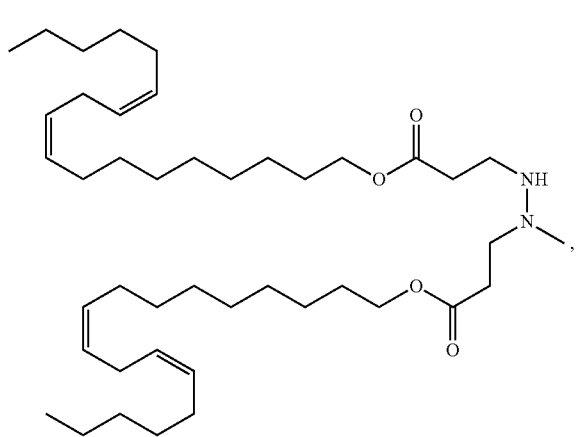
(41)

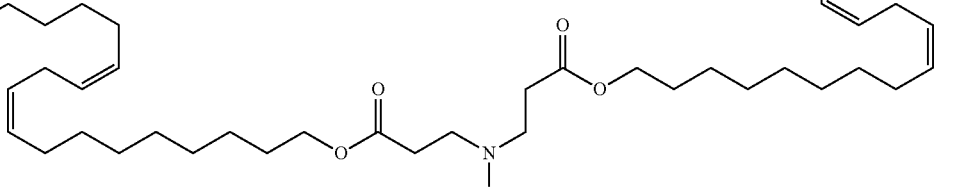
(42)
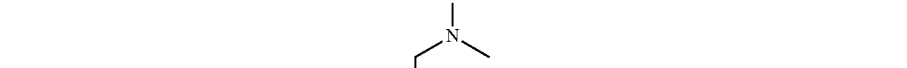
(43)
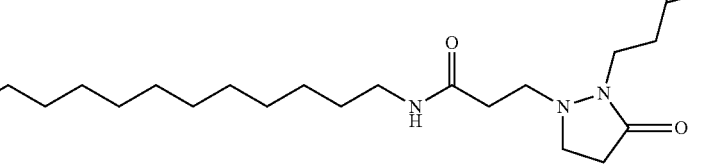
(44)
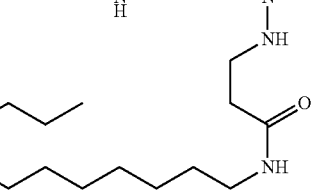
(45)

-continued
(46)
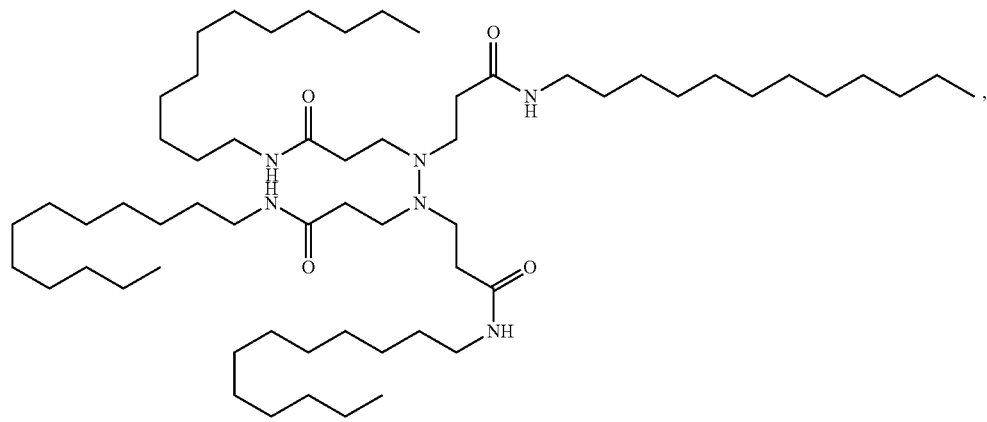
(47)
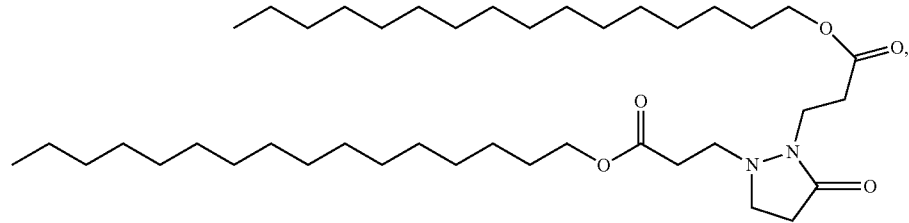
(48)
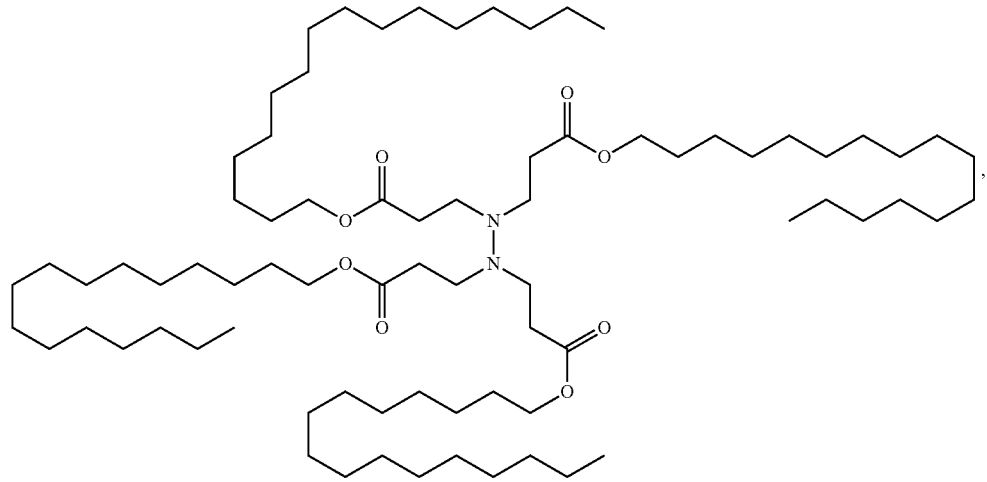
(49)
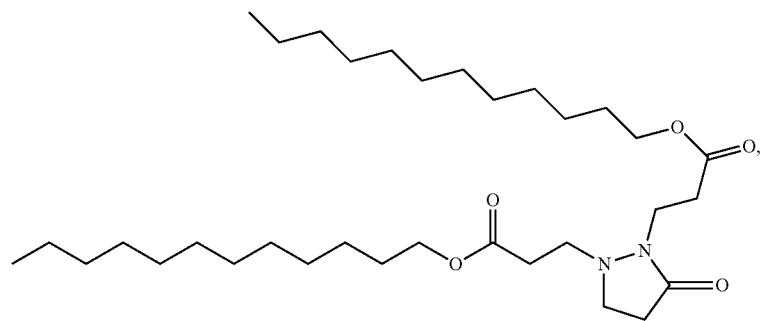

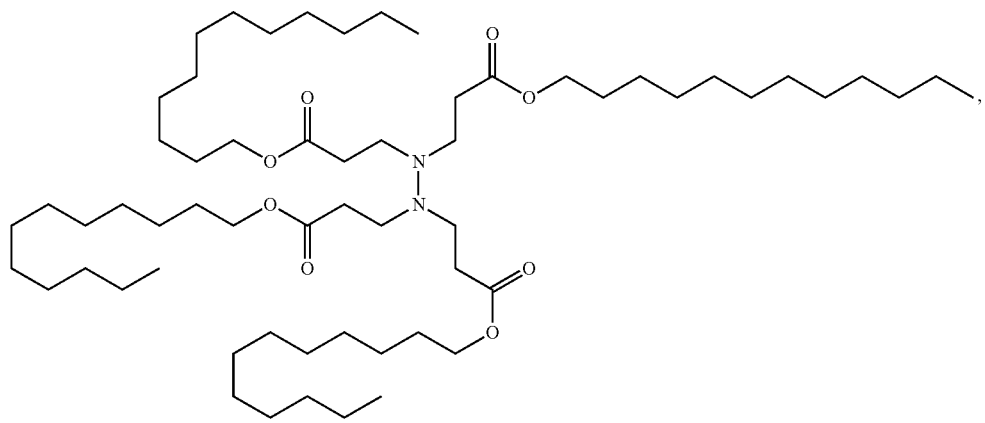
(50)
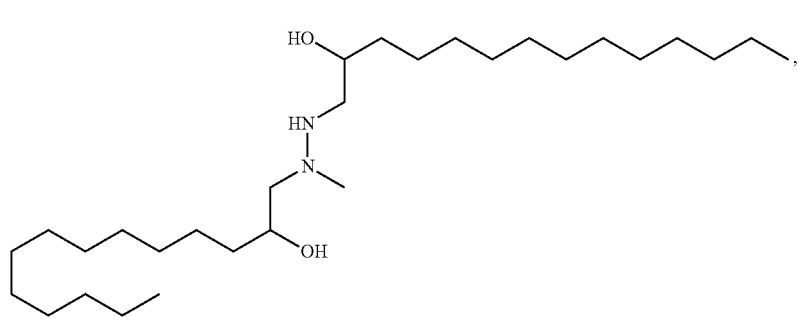
(51)
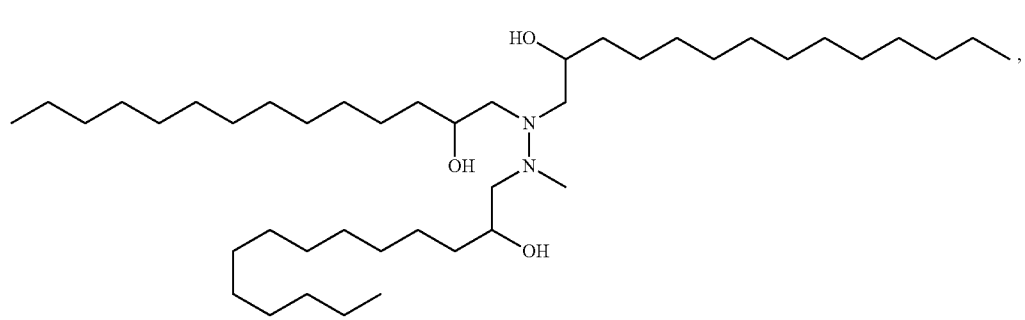
(52)
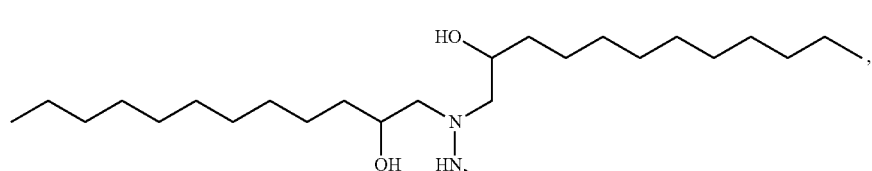
(53)
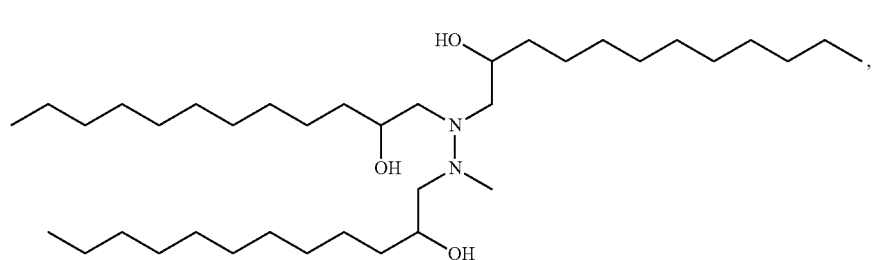
(54)

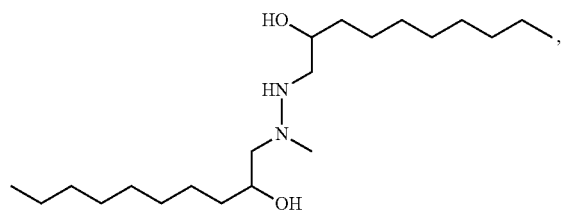
(55)
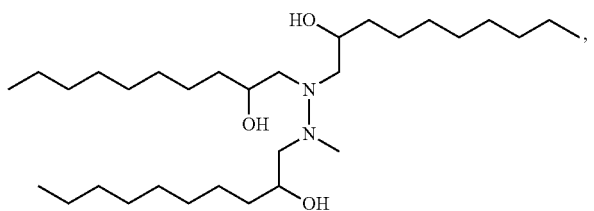
(56)
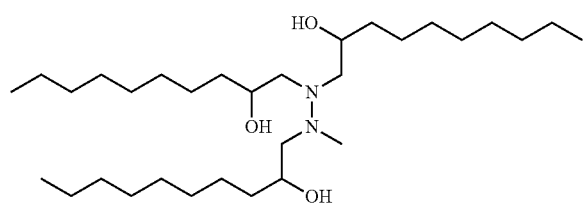
(57)
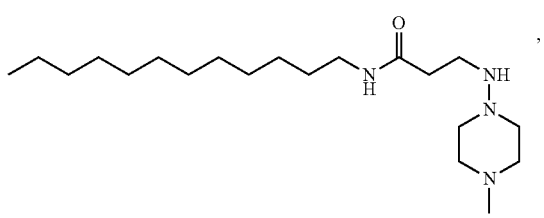
(58)
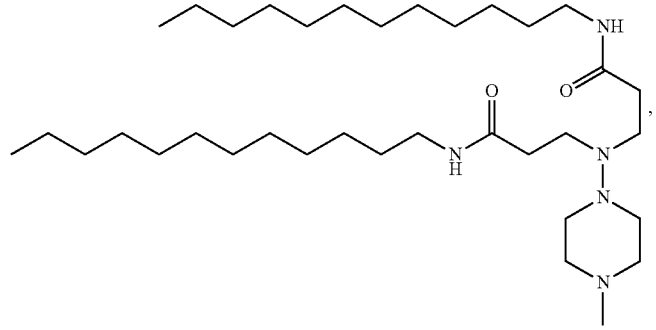
(59)
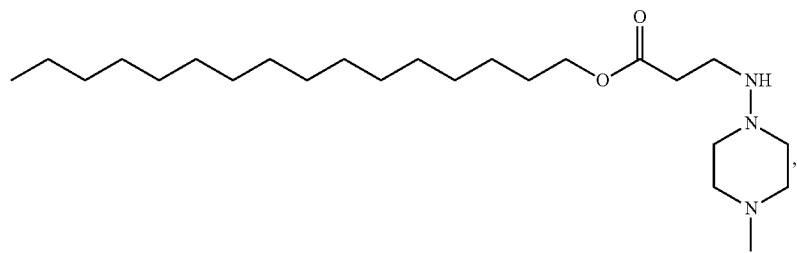
(60)
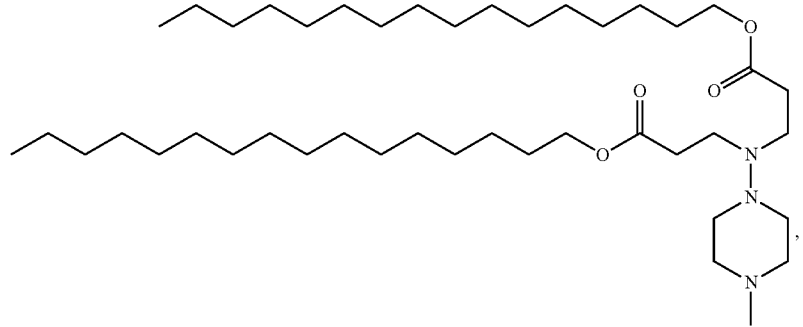
(61)

-continued
(62)
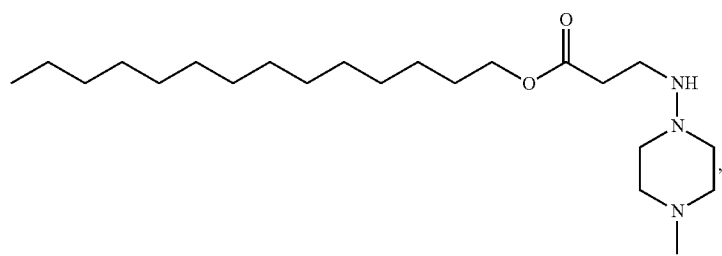
(63)
(64)
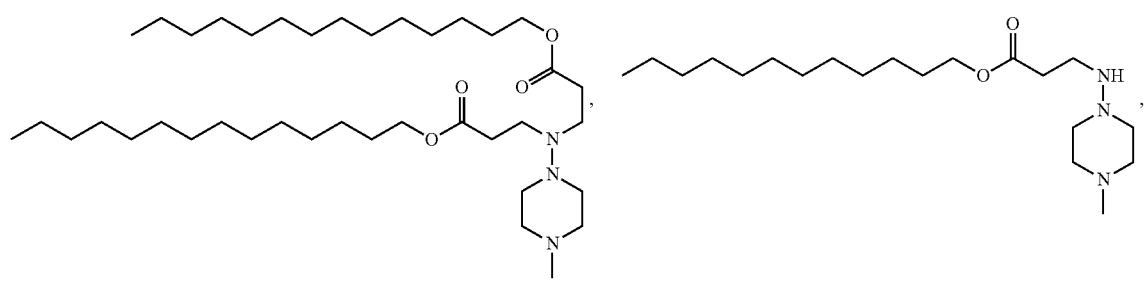
(65)
(66)
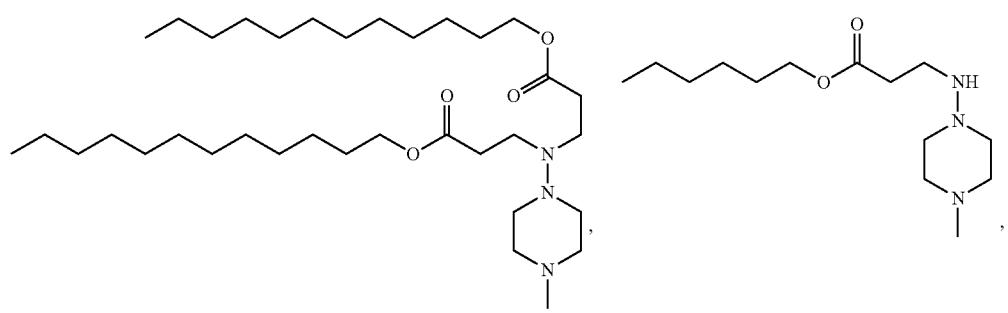
(67)
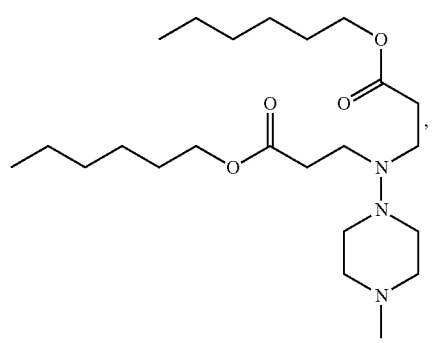
(68)
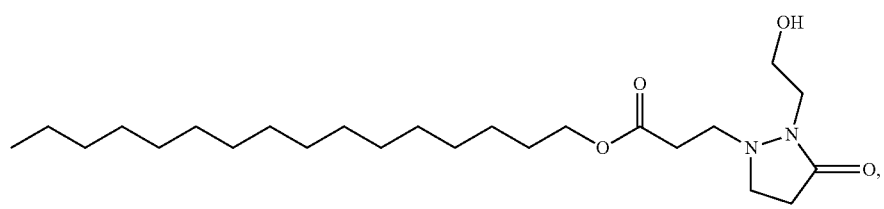

-continued
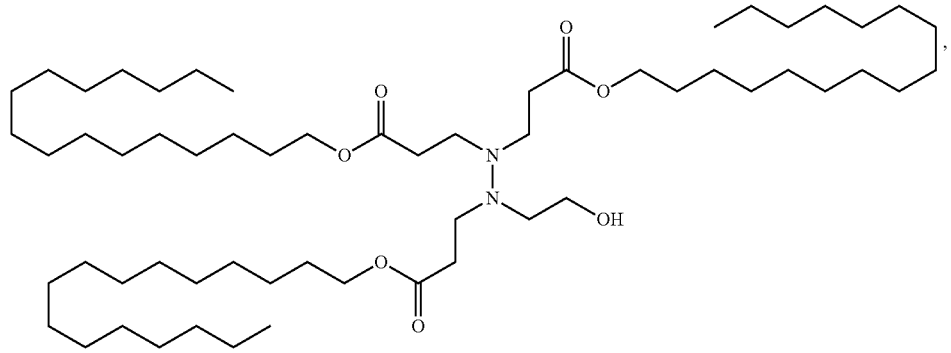
(69)
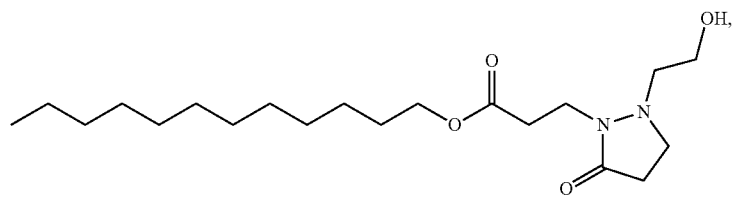
(70)
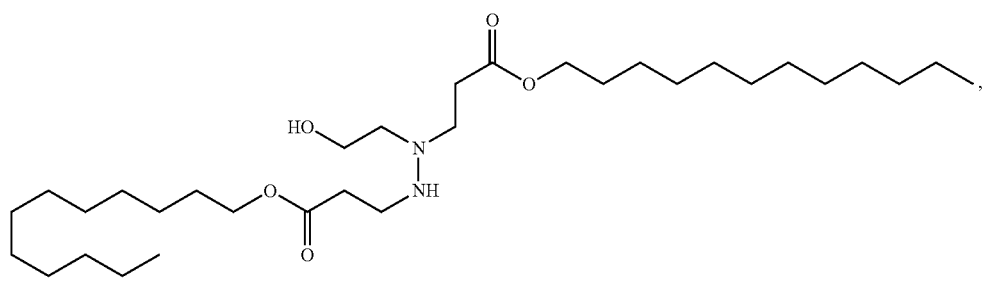
(71)
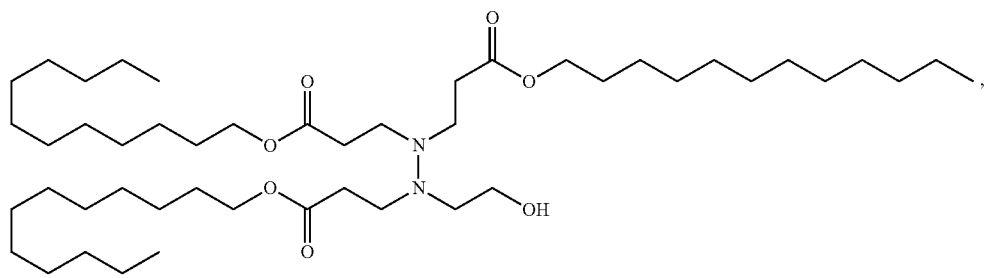
(72)
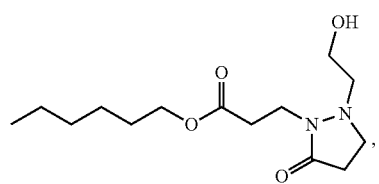
(73)
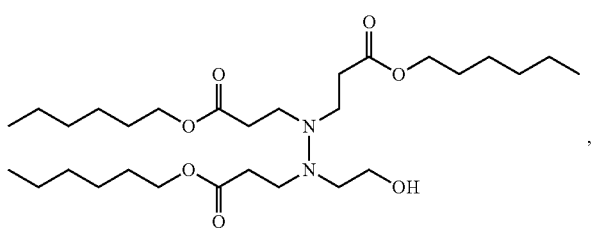
(74)
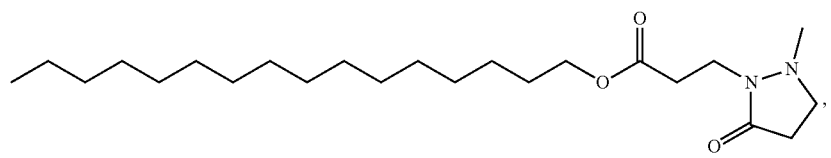
(75)

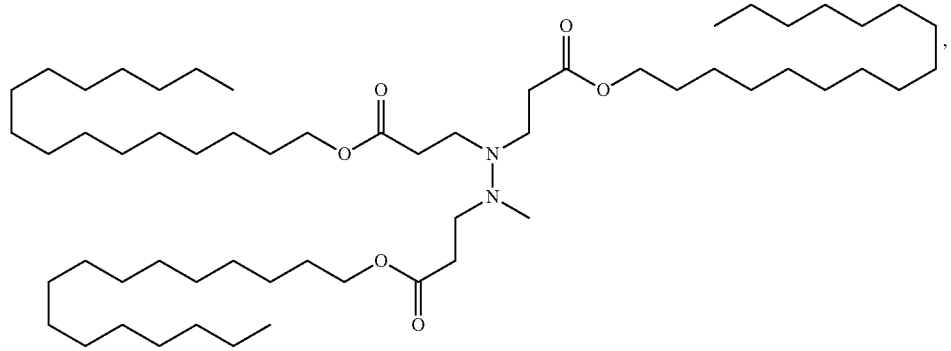
(76)
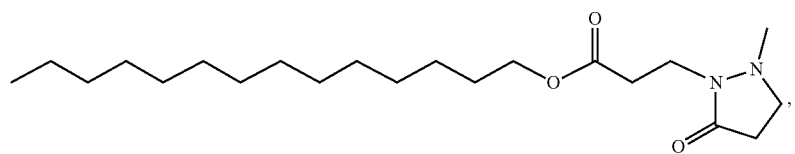
(77)
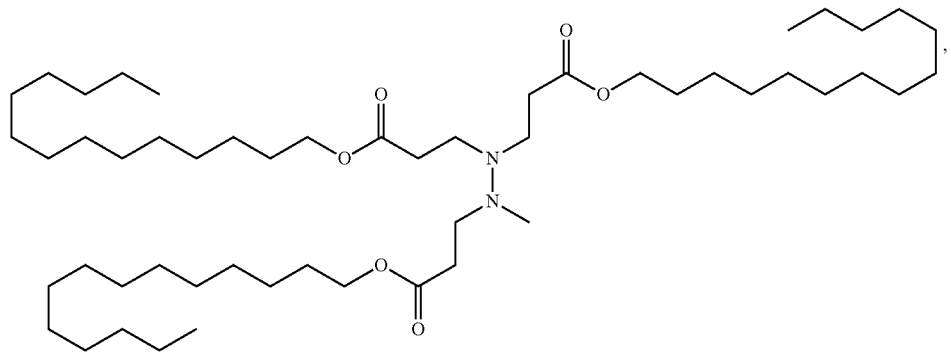
(78)
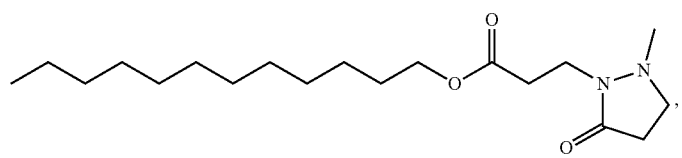
(79)
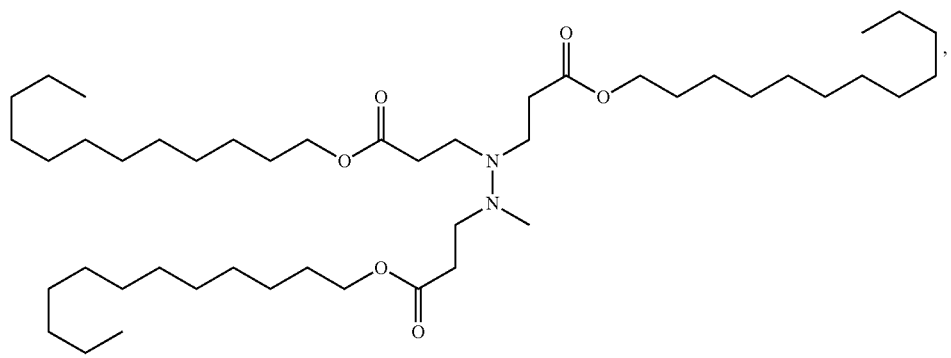
(80)

-continued
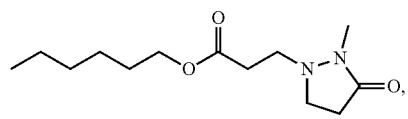
(81)
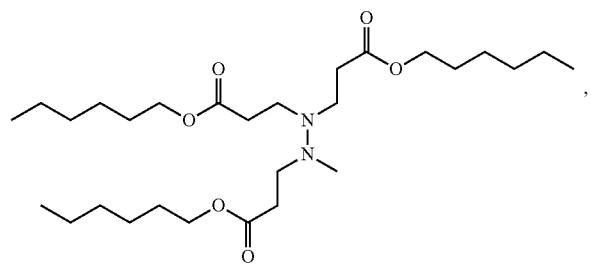
(82)
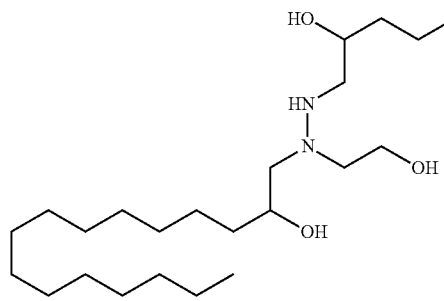
(83)
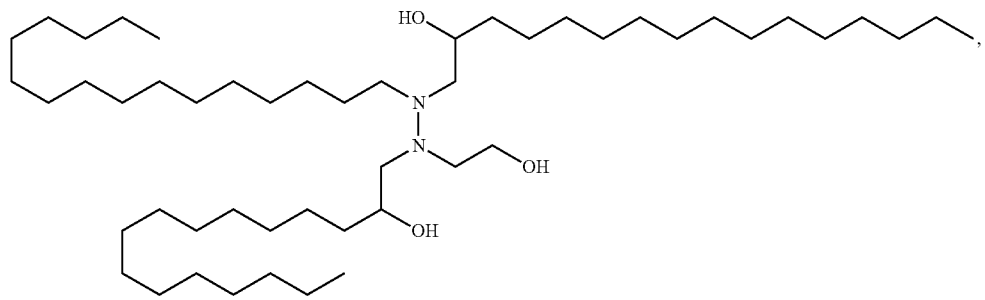
(84)
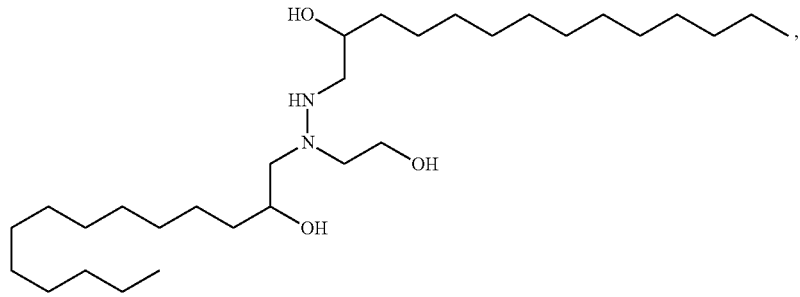
(85)
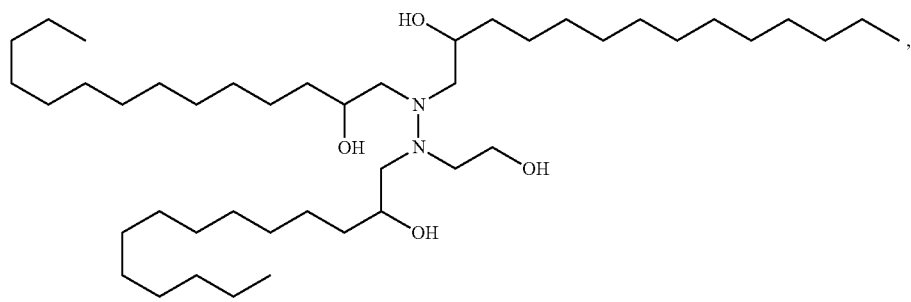
(86)

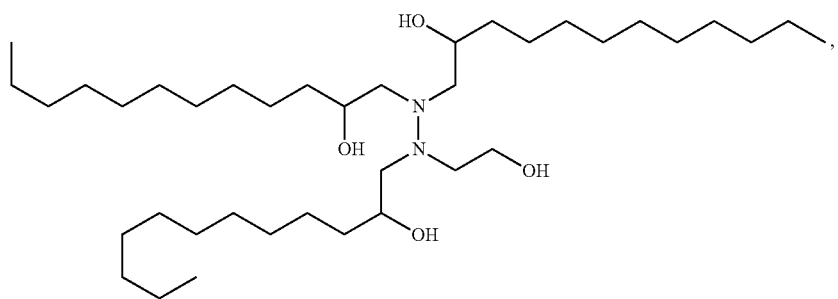
(87)
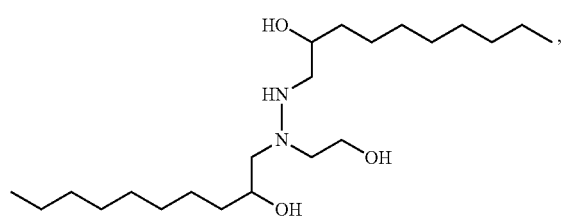
(88)
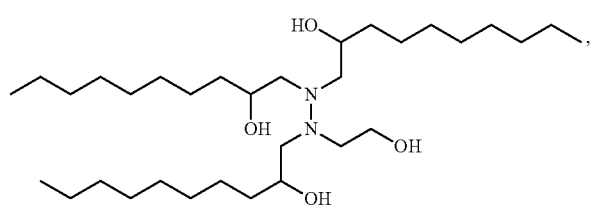
(89)
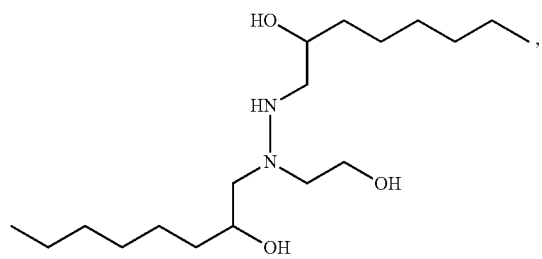
(90)
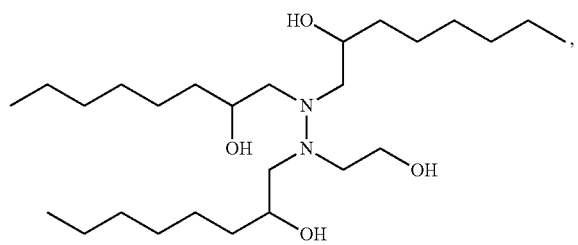
(91)
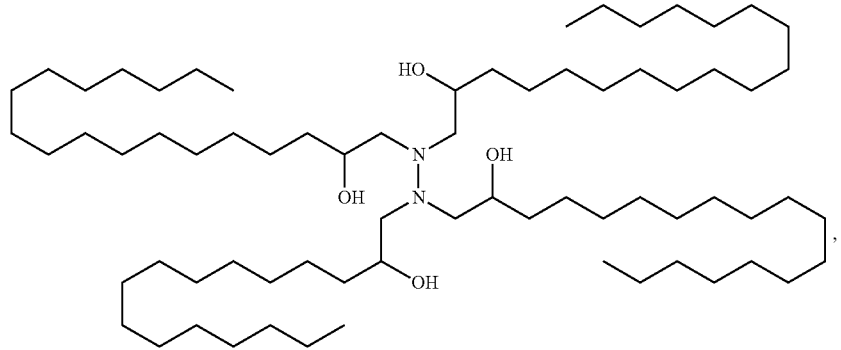
(92)
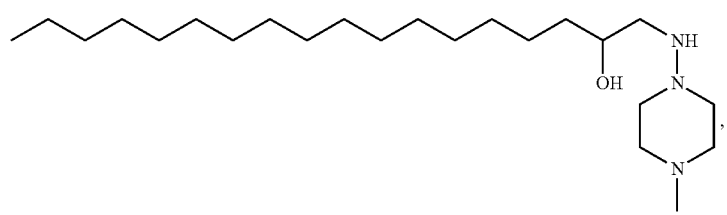
(93)

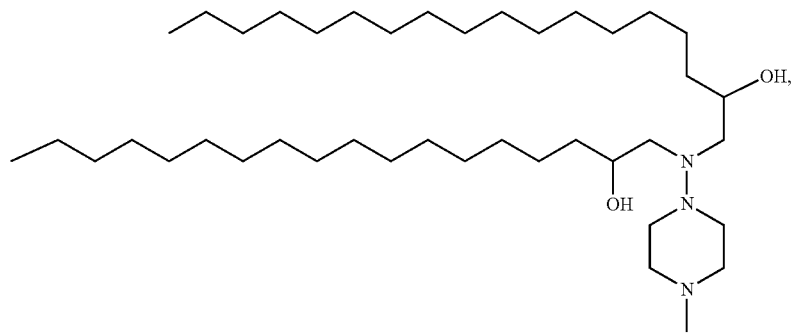
(94)
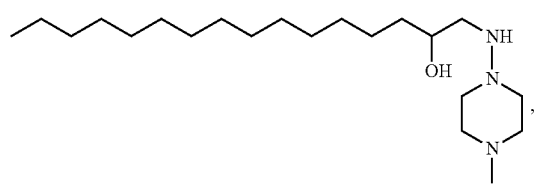
(95)
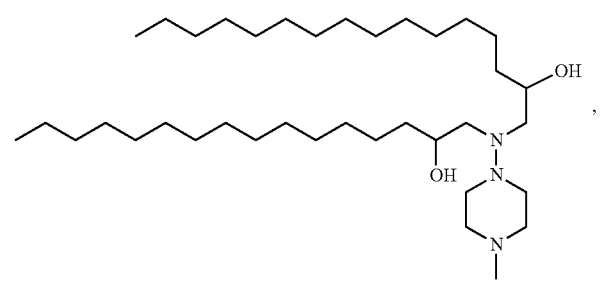
(96)
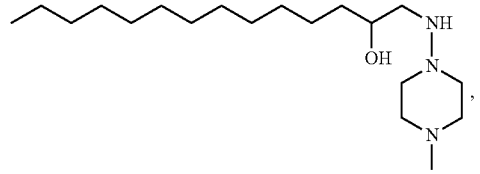
(97)
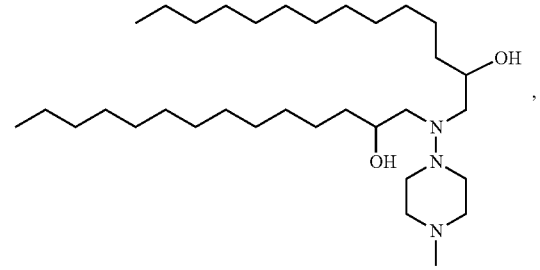
(98)
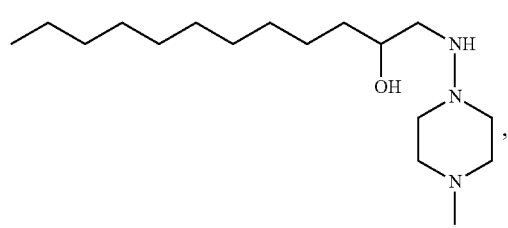
(99)
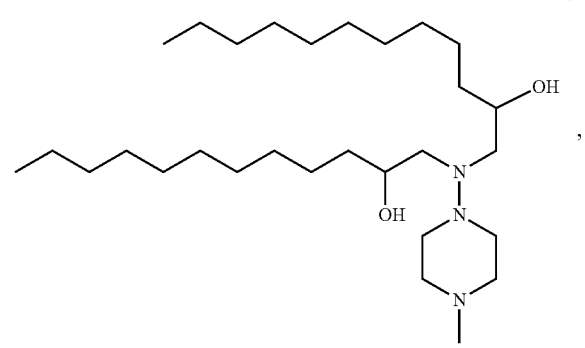
(100)
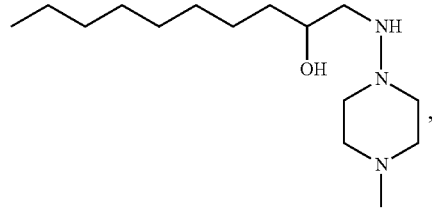
(101)
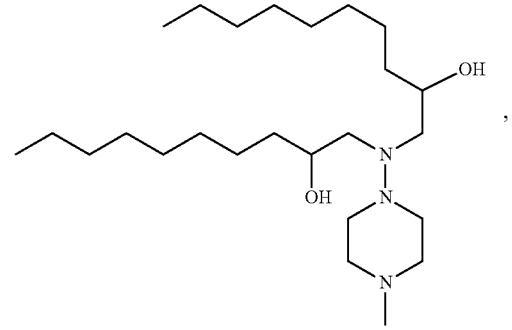
(102)

(103) 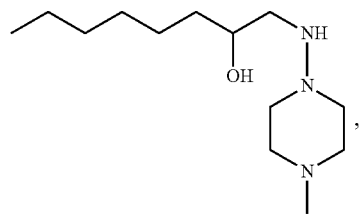
(104) 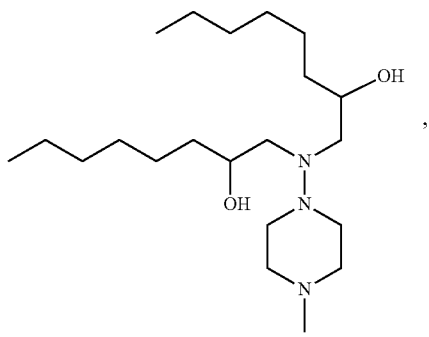
(105) 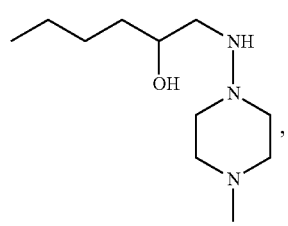
(106) 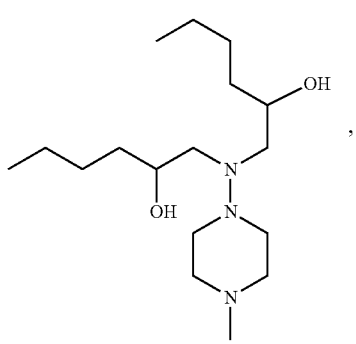
(107) 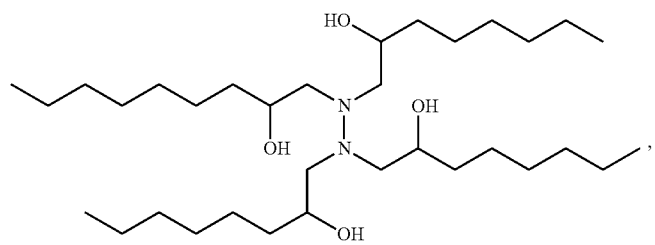
(108) 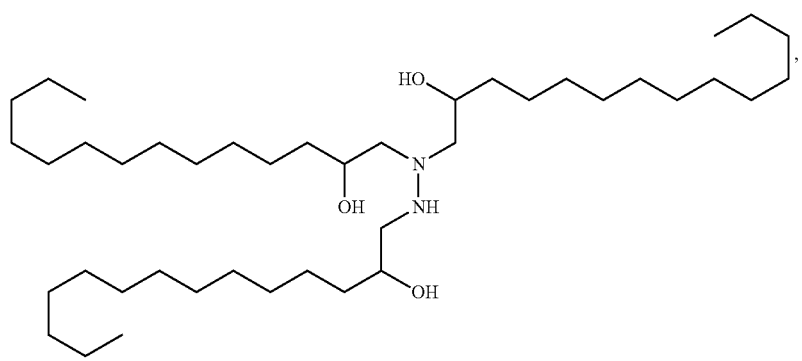
(109) 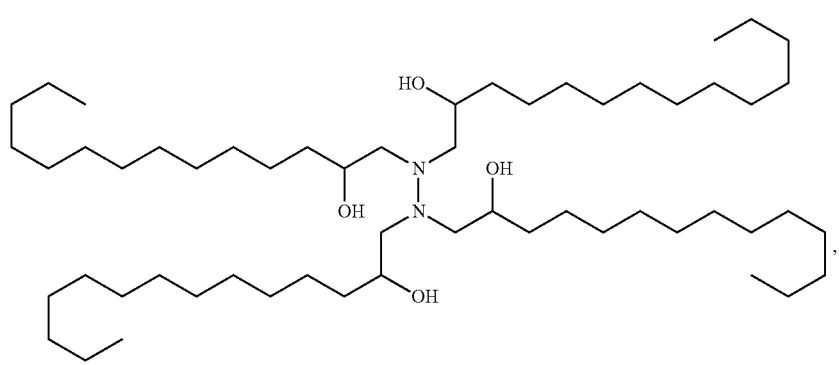

-continued
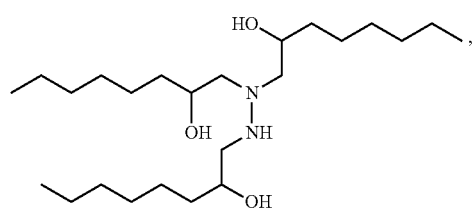 (110)
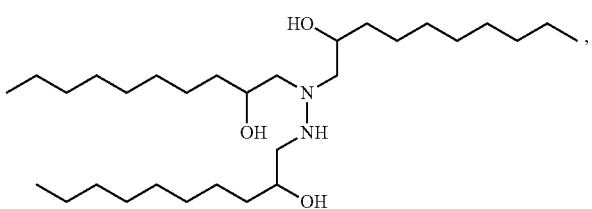 (111)
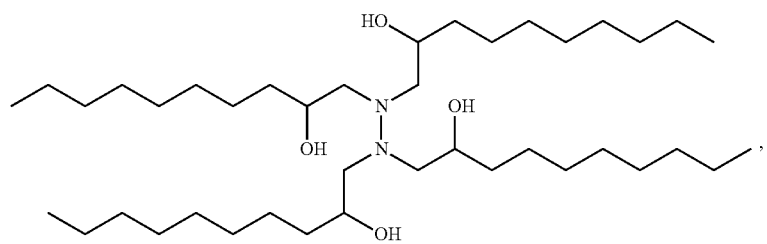 (112)
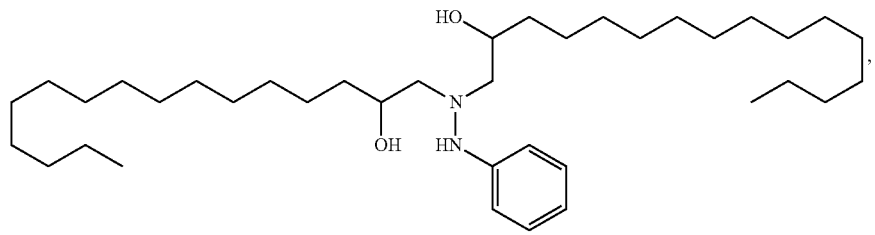 (113)
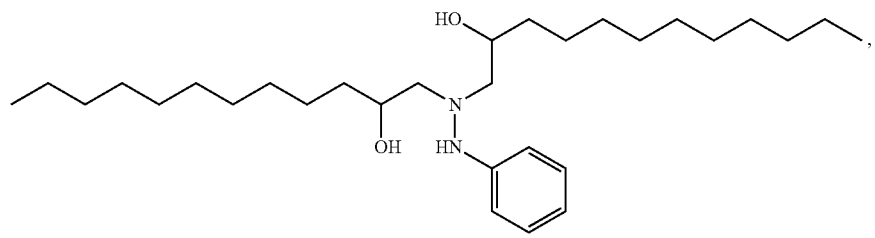 (114)
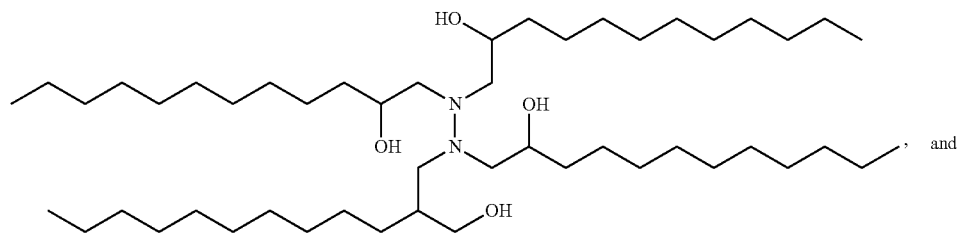 (115) and
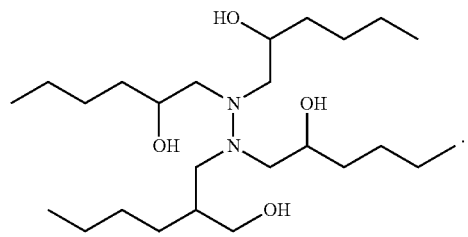 (116)

In certain embodiments, the presently disclosed hydrazinyl and hydrazinylalcohol lipidoids are relatively non-cytotoxic. In certain embodiments, the presently disclosed hydrazinyl and hydrazinylalcohol lipidoids are biocompatible and biodegradable. In certain embodiments, the presently disclosed hydrazinyl and hydrazinylalcohol lipidoids have a pKa in the range of from about 3.0 to about 9.0, or in the range of from about 5.0 to about 8.0, or in the range of from about 5.5 to about 7.5, or in the range of from about 6.0 to about 7.0.

The presently disclosed hydrazinyl and hydrazinylalcohol lipidoids may exist in particular geometric or stereoisomeric forms. The present disclosure contemplates all such forms, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent, such as an alkyl group. All such isomers, as well as mixtures thereof, are intended to be included in this disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present disclosure. Those of ordinary skill in the art will readily appreciate that analogous ratios are contemplated for more complex isomer mixtures.

If a particular enantiomer of the presently disclosed hydrazinylalcohol lipidoids is desired, it may be prepared by asymmetric synthesis, for example, by reacting hydrazine or a substituted hydrazine with a chiral epoxide. It may also be prepared by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts can be formed with an appropriate optically-active acid or base, followed by resolution of the diastereomers thus formed by fractional crystallization or chromatographic means well known in the art, and subsequent recovery of the pure enantiomers.

The hydrazinylalcohol lipidoid compounds of the present disclosure contain at least two stereocenters, as shown in formula (VIII):

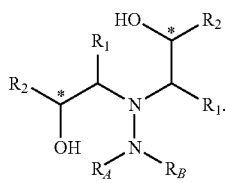

If one or both of $R_A$ and $R_B$ is a group of formula (II), then the presently disclosed novel hydrazinylalcohol lipidoid compounds contain at least three or at least four stereocenters, as shown in formula (IX):

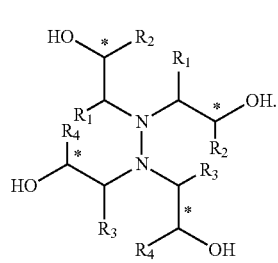

If one or both groups R1 and/or one or both groups R3 are not hydrogen, it is possible that the presently disclosed compounds can contain one, two, three, or four additional stereocenters. Therefore, in certain embodiments of the presently disclosed compounds, each group of formula (IIa):

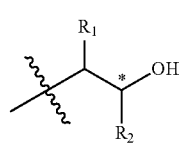

is, independently, a group of formulae (IIb) or (IIc):

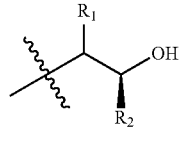

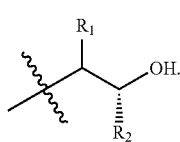

In other embodiments of the presently disclosed compounds, each group of formula (II):

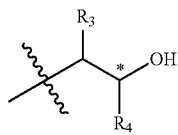

is, independently, a group of formulae (IId) or (IIe):

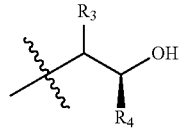

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess. For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

The hydrazinylalcohol lipidoid compounds of the present disclosure can have an enantiomeric excess or a diastereomeric excess up to and including 2%, 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100%.

The presently disclosed hydrazinyl and hydrazinylalcohol lipidoids may be prepared by any method known in the art. In certain embodiments, the hydrazinyl lipidoid compounds of the present disclosure are synthesized by reacting hydrazine or a substituted hydrazine with one or more acrylates or acrylamides. In certain embodiments, the hydrazinylalcohol lipidoid compounds of the present disclosure are synthesized by reacting hydrazine or a substituted hydrazine with one or more terminal or interior epoxides. In certain embodiments, these starting materials are commercially available and/or are easily and/or inexpensively prepared. Scheme 1 depicts this reaction where hydrazine is reacted with a terminal epoxide:

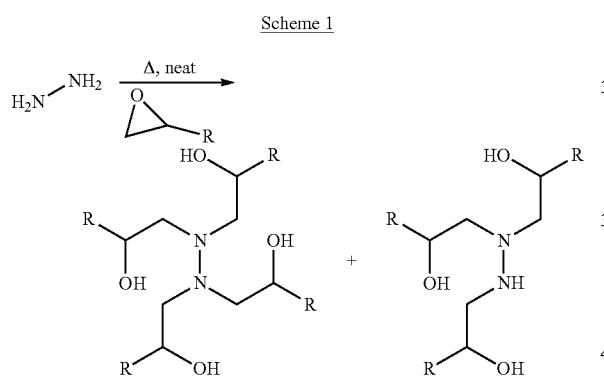

In certain embodiments, the hydrazine is reacted in the presence of a stoichiometric excess of a terminal or interior epoxide. In certain embodiments, the synthesis of the hydrazinyl and hydrazinylalcohol lipidoid compounds is performed without solvent (i.e., neat). In certain embodiments, the hydrazine and the terminal or interior epoxide are reacted at a temperature of about 120° C. for about 3 days. After the reaction is complete, the reaction mixture is cooled and the crude product is purified.

The synthesized hydrazinyl and hydrazinylalcohol lipidoid compounds may be purified by any technique known in the art including, but not limited to, precipitation, crystallization, chromatography, and distillation. In certain embodiments, the crude product is purified by silica gel chromatography.

In certain embodiments, hydrazinyl and hydrazinylalcohol lipidoids of the present disclosure can be synthesized such that one nitrogen of the hydrazine core has identical substitutents that are different to the identical substituents on the other nitrogen of the hydrazine core. For example, this can be achieved through substituting one of the hydrazine atoms with a protecting group and then reacting the protected hydrazine with a terminal or interior epoxide. This reaction is shown in Scheme 2, where benzyl N-aminocarbamate is used as the protected hydrazine, which is reacted with 1,2-epoxydodecane:

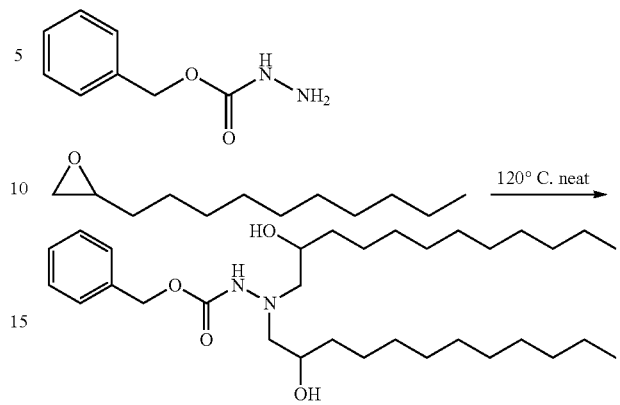

The product is the deprotected according to the reaction in Scheme 3 using palladium on carbon in the presence of hydrogen gas:

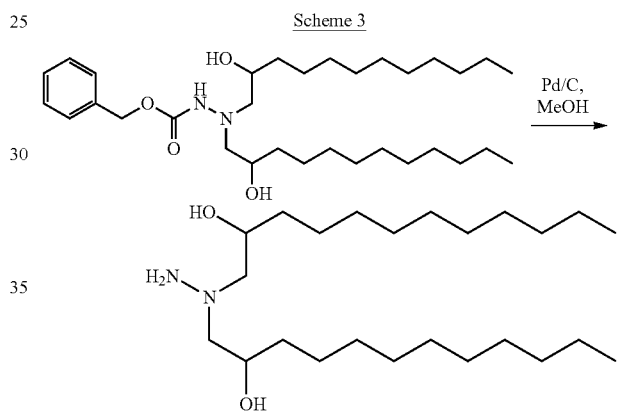

The deprotected product is then subsequently reacted 1,2-epoxyhexane to yield a final product having differentiated substituents on each nitrogen of the hydrazine core, as shown in Scheme 4:

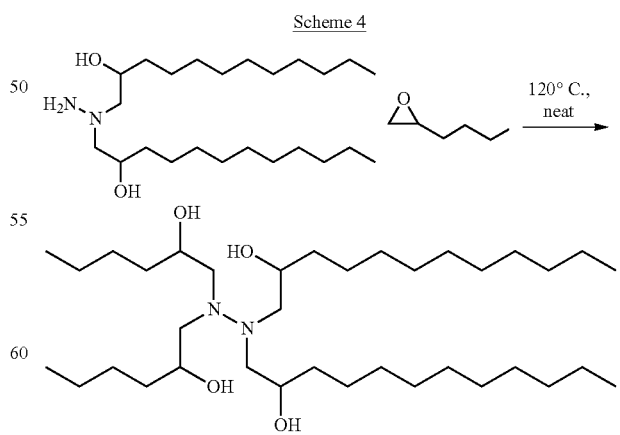

Examples of amino-protecting groups that may be used in the above reaction sequence include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative. N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide. N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, I-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl)amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzene sulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethane sulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Formulations of Hydrazinyl Lipidoids

In another aspect, the present disclosure provides for formulations comprising the presently disclosed hydrazinyl or hydrazinylalcohol lipidoids that may be used to deliver one or more active agents to a target organism. Therefore, in another aspect, the present disclosure provides for formulations that comprise one or more hydrazinyl or hydrazinylalcohol lipidoids of the present disclosure and one or more active agents. Such formulations can take any form. Examples of such forms include, but are not limited to, complexes, particles (e.g., microparticles, nanoparticles, and picoparticles), micelles, and liposomes. In certain embodiments, two or more active agents (e.g., two or more siRNA) can be formulated with the presently disclosed hydrazinyl or hydrazinylalcohol lipidoids to form a single complex, particle, micelled or liposome containing the two or more active agents. Alternatively, in certain embodiments, the two or more active agents can be separately formulated to form a single complex, particle, micelled or liposome, each containing a single active agent, and are then combined to form a mixture prior to delivery to a target organism.

The hydrazinyl and hydrazinylalcohol lipidoids of the present disclosure possess a hydrazine core that, although hindered, is available to interact with an active agent (e.g., a polynucleotide). As such, a complex is formed when an active agent is contacted with the presently disclosed hydrazinyl or hydrazinylalcohol lipidoids under conditions suitable to form an agent/lipidoid complex. In certain embodiments, multiple hydrazinyl or hydrazinylalcohol lipidoid molecules may complex with an agent molecule. The complex may include 1-100 hydrazinyl or hydrazinylalcohol lipidoid molecules, 1-1000 hydrazinyl or hydrazinylalcohol lipidoid molecules, 10-1000 hydrazinyl or hydrazinylalcohol lipidoid molecules, or 100-10,000 hydrazinyl or hydrazinylalcohol lipidoid molecules.

The hydrazinyl and hydrazinylalcohol lipidoid compounds of the present disclosure may be used to encapsulate active agents. The hydrazinyl and hydrazinylalcohol lipidoid compounds of the present disclosure have several properties that make them particularly suitable in the preparation of drug delivery devices. These include, but are not limited to: (1) the ability of the lipidoid to complex and "protect" labile agents, (2) the ability to buffer the pH in the endosome (3) the ability to act as a "proton sponge" and cause endosomolysis, and (4) the ability to neutralize the charge on negatively charged agents. Thus, in certain embodiments, the hydrazinyl and hydrazinylalcohol lipidoid compounds of the present disclosure are used to form particles containing an active agent to be delivered. These particles may include other materials, such as proteins, carbohydrates, synthetic polymers (e.g., PEG, PLGA), and natural polymers.

In certain embodiments, the inventive hydrazinyl and hydrazinylalcohol lipidoids are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The inventive hydrazinyl or hydrazinylalcohol lipidoid compounds may be combined with other hydrazinyl and hydrazinylalcohol lipidoid compounds, polymers (synthetic or natural), surfactants, cholesterol, carbohydrates, proteins, and lipids, to form the particles.

In certain embodiments, the diameter of the particles range from 1 to 1,000 micrometers. In certain embodiments, the diameter of the particles range from 1 to 100 micrometers. In certain embodiments, the diameter of the particles range from 1 to 10 micrometers. In certain embodiments, the diameter of the particles range from 10 to 100 micrometers. In certain embodiments, the diameter of the particles range from 100 to 1,000 micrometers. In certain embodiments, the diameter of the particles range from 1 to 5 micrometers. In certain embodiments, the diameter of the particles range from 1 to 1,000 nm. In certain embodiments, the diameter of the particles range from 1 to 100 nm. In certain embodiments, the diameter of the particles range from 1 to 10 nm. In certain embodiments, the diameter of the particles range from 10 nm to 100 nm. In certain embodiments, the diameter of the particles range from 100 nm to 1,000 nm. In certain embodiments, the diameters of the particles range from 1 to 5 nm. In certain embodiments, the diameter of the particles range from 1 to 1,000 pm. In certain embodiments, the diameter of the particles range from 1 to 100 pm. In certain embodiments, the diameter of the particles range from 1 to 10 pm. In certain embodiments, the diameter of the particles range from 10 to 100 pm. In certain embodiments, the diameter of the particles range from 100 to 1,000 pm. In certain embodiments, the diameter of the particles range from 1 to 5 pm.

The particles of the present disclosure may be prepared using any method known in the art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. In other embodiments, methods of preparing the particles are nanoprecipitation or flash precipitation, for example, as disclosed in U.S. Pat. Nos. 8,207,290, 8,404,799, 8,546,521, 8,618,240, and 8,809,492, each of which are incorporated herein in its entirety. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix. Methods developed for making particles for delivery of encapsulated agents are described in the literature (e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference in their entirety).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

The hydrazinyl and hydrazinylalcohol lipidoids of the invention may be used to prepare micelles or liposomes containing an agent to be delivered. Many techniques for preparing micelles and liposomes are known in the art, and any method may be used with the inventive hydrazinyl and hydrazinylalcohol lipidoid compounds to make micelles and liposomes. Micelles and liposomes are particularly useful in delivering hydrophobic agents, such as hydrophobic small molecules.

In certain embodiments, liposomes of the present disclosure are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See Walde, P. "Preparation of Vesicles (Liposomes)" In *Encyclopedia of Nanoscience and Nanotechnology*; Nalwa, H. S. Ed. American Scientific Publishers: Los Angeles, 2004; Vol. 9, pp. 43-79; Szoka et al. "Comparative Properties and Methods of Preparation of Lipid Vesicles (Liposomes)" *Ann. Rev. Biophys. Bioeng.* 9:467-508, 1980; each of which is incorporated herein in its entirety.

The preparation of liposomes of the present disclosure involves preparing the hydrazinyl and hydrazinylalcohol lipidoids for hydration, hydrating the hydrazinyl and hydrazinylalcohol lipidoids with agitation, and sizing the vesicles to achieve a homogenous distribution of liposomes. Hydrazinyl and hydrazinylalcohol lipidoids are first dissolved in an organic solvent to assure a homogeneous mixture. The solvent is then removed to form a lipidoid film. This film is thoroughly dried to remove residual organic solvent by placing the vial or flask on a vacuum pump overnight. Hydration of the lipidoid film/cake is accomplished by adding an aqueous medium to the container of dry lipidoid and agitating the mixture. Disruption of LMV suspensions using sonic energy typically produces small unilamellar vesicles (SUV) with diameters in the range of from 15 to 50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of from 120 to 140 nm.

Certain hydrazinyl and hydrazinylalcohol lipidoids of the present disclosure can spontaneously self assemble around certain molecules, such as DNA and RNA, to form liposomes. In some embodiments, the application is the delivery of polynucleotides to a target cell. Thus, use of the hydrazinyl and hydrazinylalcohol lipidoids of the present disclosure allows for simple assembly of liposomes without the need for additional steps or devices such as an extruder.

The complexes, microparticles, nanoparticles, picoparticles, liposomes, and micelles of the present disclosure may be modified to include targeting agents since it is often desirable to target a particular cell, collection of cells, or tissue. A variety of targeting agents that direct pharmaceutical compositions to particular cells are known in the art (e.g., Cotten et al. Methods Enzym. 217:618, 1993; which is incorporated herein by reference in its entirety). The targeting agents may be included throughout the particle or may be only on the surface. The targeting agent may be a protein, peptide, carbohydrate, glycoprotein, lipid, small molecule, nucleic acid, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Herbicidal and Pesticidal Applications

In another aspect, the presently disclosed hydrazinyl and hydrazinylalcohol lipidoid-based formulations can be used to deliver an active agent to target organisms for the purpose of killing and/or controlling the proliferation of the target organisms, such as insects, plant pathogens (e.g., fungi, bacteria, viruses, and nematodes), and weeds. In certain embodiments, the presently disclosed hydrazinyl and hydrazinylalcohol lipidoid-based formulations comprise an insecticidal, nematidicidal, fungicidal, bacteriocidal, viricidal, or herbicidal active agent, or combinations thereof. In certain embodiments, these formulations are combined with an agriculturally acceptable carrier to form a insecticidal, nematicidal, fungicidal, bacteriocidal, viricidal, or herbicidal formulation.

A target organism is an organism in which the presently disclosed herbicidal, insecticidal, or fungicidal formulations are intended to be functional, for example, to mediate gene silencing or suppression. In certain embodiments, a target organism is also a host organism, as described herein below. In other embodiments, a target organism is separate and distinct from a host organism that serves as a source of the active agent to be functional in the target organism.

The insecticidal, nematidicidal, fungicidal, bacteriocidal, viricidal, or herbicidal formulation may further be combined with an agriculturally acceptable carrier. The agriculturally acceptale carrier can be solid or liquid and is a substance useful in formulation of agricultural products, for example, fertilizers, herbicides, insecticides, fungicides, bactericides, viricides, and nematicides. Agriculturally acceptable carriers include, for example, natural or regenerated mineral substances, solvents, dispersants, wetting agents, tackifiers, thickeners, binders or fertilizers. Such carriers are described for example, in WO 97/33890, which is incorporated herein by reference.

The presently disclosed formulations of the present disclosure can be applied to the crop area or plant to be treated, simultaneously or in succession with further compounds. These further compounds can be, for example, fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

Active Agents

Active agents that can be delivered to a target organism using the presently disclosed formulations include, but are not limited to, any type of molecule or compound including, but not limited to, nucleic acids, peptides, polypeptides, small molecules, and mixtures thereof. Examples of nucleic acids include, but are not limited to, interfering RNA molecules (e.g., siRNA, aiRNA, miRNA), antisense oligonucleotides, plasmids, ribozymes, immunostimulatory oligonucleotides, and mixtures thereof.

In certain embodiments, the active agent comprises a nucleic acid. In certain embodiments, the nucleic acid comprises an interfering RNA molecule such as, e.g., an siRNA, aiRNA, miRNA, or mixtures thereof. In certain embodiments, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In certain embodiments, presently disclosed particles are associated with a nucleic acid. In some embodiments, the nucleic acid is fully encapsulated in a lipidoid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are about 10, 15, 20, 25, 30, 35, 40, 45, 50, 55 or 60 nucleotides in length. Any of these values may be used to define a range for the size of the oligonucleotide. For example, the size of the oligonucleotide may range from 15-60, 20-60 or 25-60 nucleotides in length. In particular embodiments, the polynucleotide is 65, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or more nucleotides in length. In particular embodiments, the polynucleotide is at least 65, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900 or 2000 nucleotides in length. Any of these values may be used to define a range for the size of the polynucleotide. For example, the polynucleotide may range from 100-150, 150-200, 200-250, 250-300, 300-350, 350-400, 450-500, 500-550, 550-600, 600-650, 650-700, 700-750, 750-800, 800-850, 850-900, 900-950, or 950-1000 nucleotides in length. The nucleic acid may be administered alone in the particles of the present disclosure, or in combination (e.g., co-administered) with particles of the present disclosure comprising peptides, polypeptides, or small molecules, such as conventional drugs.

In the context of this invention, the terms "polynucleotide" and "oligonucleotide" refer to a polymer or oligomer of nucleotide or nucleoside monomers consisting of naturally-occurring bases, sugars, and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

Nucleic acids that can be used in the presently disclosed formulations includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as aiRNA and pre-miRNA. Single-stranded nucleic acids include, e.g., antisense oligonucleotides, ribozymes, mature miRNA, and triplex-forming oligonucleotides.

Nucleic acids that can be used in the formulations of the present disclosure may be of various lengths, which is generally dependent upon the particular form of nucleic acid. For example, in certain embodiments, plasmids or genes may be from about 1,000 to about 100,000 nucleotide residues in length. In certain embodiments, oligonucleotides may range from about 10 to about 100 nucleotides in length. In certain embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In certain embodiments, an oligonucleotide (or a strand thereof) that can be used in the presently disclosed formulations specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In certain embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired. Thus, the oligonucleotide may include 1, 2, 3, or more base substitutions as compared to the region of a gene or mRNA sequence that it is targeting or to which it specifically hybridizes.

In certain embodiments, the oligo- or polynucleotide is optionally purified and substantially pure. In some embodiments, the polynucleotide is greater than 50% pure. In some embodiments, the oligo- or polynucleotide is greater than 75% pure. In some embodiments, the oligo- or polynucleotide is greater than 95% pure. The oligo- or polynucleotide may be provided by any means known in the art. In certain embodiments, the oligo- or polynucleotide has been engineered using recombinant techniques. The oligo- or polynucleotide may also be obtained from natural sources and purified from contaminating components found normally in nature. The oligo- or polynucleotide may also be chemically synthesized in a laboratory. In certain embodiments, the oligo- or polynucleotide is synthesized using standard solid phase chemistry.

The oligo- or polynucleotide may be modified by chemical or biological means. In certain embodiments, these modifications lead to increased stability of the oligo- or polynucleotide. Examples of such modifications include, but are not limited to, methylation, phosphorylation, and end-capping.

The oligo- or polynucleotide to be delivered may be in any form. Examples of such forms include, but are not limited to, a circular plasmid, a linearized plasmid, a cosmid, a viral genome, a modified viral genome, an artificial chromosome, dsRNA, ssRNA, dsDNA, ssDNA, RNA/DNA hybrids, dsRNA hairpins, siRNA, aiRNA, and miRNA.

The oligo- or polynucleotide may be of any sequence. In certain embodiments, the oligo- or polynucleotide encodes a protein or peptide. The encoded proteins may be enzymes, structural proteins, receptors, soluble receptors, ion channels, or cytokines. The oligo- or polynucleotide may also comprise regulatory regions to control the expression of a gene. These regulatory regions may include, but are not limited to, promoters, enhancer elements, repressor elements, TATA box, ribosomal binding sites, and stop site for transcription. In certain embodiments, the polynucleotide is not intended to encode a protein.

In certain embodiments, the oligo- or polynucleotide is an RNA that carries out RNA interference (RNAi). The term "interfering RNA" or "RNAi" or "interfering RNA sequence" refers to single-stranded RNA (e.g., mature miRNA) or double-stranded RNA (e.g., duplex RNA, such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof.

siRNA

In certain embodiments, the active agent comprises an siRNA. The siRNA molecule can comprise a double-stranded region of about 15 to about 60 nucleotides in length (e.g., about 15 to 60, 15 to 50, 15 to 40, 15 to 30, 15 to 25, or 19 to 25 nucleotides in length, or 15, 16, 17, 18, 19, 20, 21, 22, 23, 24, or 25 nucleotides in length). The siRNA molecules used in the presently disclosed formulations are capable of silencing the expression of a target sequence in vitro and/or in vivo.

In certain embodiments, the siRNA molecule comprises modified nucleotides including, but not limited to, 2'-O-methyl (2'OMe) nucleotides, 2'-deoxy-2'-fluoro(2'F) nucleotides, 2'-deoxy nucleotides, 2'-O-(2-methoxyethyl) (MOE) nucleotides, locked nucleic acid (LNA) nucleotides, and mixtures thereof. In other embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain embodiments, the siRNA does not comprise 2'OMe-cytosine nucleotides. In certain embodiments, the siRNA comprises a hairpin loop structure.

In certain embodiments, the siRNA may comprise modified nucleotides in one strand (i.e., sense or antisense) or both strands of the double-stranded region of the siRNA molecule. In certain embodiments, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In certain embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In certain embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In certain embodiments, a modified siRNA molecule is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target sequence relative to the corresponding unmodified siRNA sequence.

In certain embodiments, the siRNA molecule does not comprise phosphate backbone modifications, e.g., in the sense and/or antisense strand of the double-stranded region. In certain embodiments, the siRNA comprises one, two, three, four, or more phosphate backbone modifications, e.g., in the sense and/or antisense strand of the double-stranded region. In certain embodiments, the siRNA does not comprise phosphate backbone modifications.

In certain embodiments, the siRNA does not comprise 2'-deoxy nucleotides, e.g., in the sense and/or antisense strand of the double-stranded region. In certain embodiments, the siRNA comprises one, two, three, four, or more 2'-deoxy nucleotides, e.g., in the sense and/or antisense strand of the double-stranded region. In certain embodiments, the siRNA does not comprise 2'-deoxy nucleotides.

In certain embodiments, the nucleotide at the 3'-end of the double-stranded region in the sense and/or antisense strand is not a modified nucleotide. In certain embodiments, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the siRNA has 3' overhangs of two nucleotides on each side of the double-stranded region. In certain embodiments, the 3' overhang on the antisense strand has complementarity to the target sequence and the 3' overhang on the sense strand has complementarity to a complementary strand of the target sequence. Alternatively, the 3' overhangs do not have complementarity to the target sequence or the complementary strand thereof. In certain embodiments, the 3' overhangs comprise one, two, three, four, or more nucleotides such as 2'-deoxy(2'H) nucleotides. In certain embodiments, the 3' overhangs comprise deoxythymidine (dT) and/or uridine nucleotides. In certain embodiments, one or more of the nucleotides in the 3' overhangs on one or both sides of the double-stranded region comprise modified nucleotides. Examples of modified nucleotides are described above and include, but are not limited to, 2'OMe nucleotides, 2'-deoxy-2'F nucleotides, 2'-deoxy nucleotides, 2'-O-2-MOE nucleotides, LNA nucleotides, and mixtures thereof. In certain embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA may comprise at least one or a cocktail (e.g., at least two, three, four, five, six, seven, eight, nine, ten, or more) of unmodified and/or modified siRNA sequences that silence target gene expression. The cocktail of siRNA may comprise sequences, which are directed to the same region or domain (e.g., a "hot spot") and/or to different regions or domains of one or more target genes. In certain embodiments, one or more (e.g., at least two, three, four, five, six, seven, eight, nine, ten, or more) modified siRNA that silence target gene expression are present in a cocktail. In certain embodiments, one or more (e.g., at least two, three, four, five, six, seven, eight, nine, ten, or more) unmodified siRNA sequences that silence target gene expression are present in a cocktail.

In certain embodiments, the antisense strand of the siRNA molecule comprises or consists of a sequence that is at least about 80%, 85%, 90%, 95%, 96%, 97%, 98%, or 99% complementary to the target sequence or a portion thereof. In certain embodiments, the antisense strand of the siRNA molecule comprises or consists of a sequence that is 100% complementary to the target sequence or a portion thereof. In certain embodiments, the antisense strand of the siRNA molecule comprises or consists of a sequence that specifically hybridizes to the target sequence or a portion thereof.

In certain embodiments, the sense strand of the siRNA molecule comprises or consists of a sequence that is at least about 80%, 85%, 90%, 95%, 96%, 97%, 98%, or 99% identical to the target sequence or a portion thereof. In certain embodiments, the sense strand of the siRNA molecule comprises or consists of a sequence that is 100% identical to the target sequence or a portion thereof.

The siRNA that can be used in the presently disclosed formulations are capable of silencing the expression of a target gene of interest. Each strand of the siRNA duplex can be about 15 to about 60 nucleotides in length, or about 15 to about 30 nucleotides in length. In certain embodiments, the siRNA comprises at least one modified nucleotide. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In certain embodiments, one or more of the uridine and/or guanosine nucleotides are modified. The modified nucleotides can be present in one strand (i.e., sense or antisense) or both strands of the siRNA. The siRNA sequences may have overhangs or may lack overhangs (i.e., have blunt ends).

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

In certain embodiments, less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%) of the nucleotides in the double-stranded region of the siRNA comprise modified nucleotides.

In certain embodiments, from about 1% to about 25% (e.g., from about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, etc.) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, etc.) of the nucleotides in the double-stranded region of the siRNA comprise modified nucleotides.

In certain embodiments, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

Examples of modified nucleotides suitable for use in the presently disclosed formulations include, but are not limited to, ribonucleotides having a 2'-O-methyl (2'OMe), 2'-deoxy-2'-fluoro(2'F), 2'-deoxy, 5-C-methyl, 2'-O-(2-methoxyethyl) (MOE), 4'-thio, 2'-amino, or 2'-C-allyl group. Modified nucleotides having a Northern conformation are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro(2'F) nucleotides, 2'-deoxy-2'-chloro(2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex. In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole can be incorporated into siRNA molecules.

In certain embodiments, the siRNA molecules may further comprise one or more chemical modifications such as terminal cap moieties, phosphate backbone modifications, and the like. Examples of terminal cap moieties include, but are not limited to, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties. Examples of phosphate backbone modifications (i.e., resulting in modified internucleotide linkages) include, but are not limited to, phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions. Such chemical modifications can occur at the 5'-end and/or 3'-end of the sense strand, antisense strand, or both strands of the siRNA.

In certain embodiments, the sense and/or antisense strand of the siRNA molecule can further comprise a 3'-terminal overhang having about 1 to about 4 (e.g., 1, 2, 3, or 4) 2'-deoxy ribonucleotides and/or any combination of modified and unmodified nucleotides.

The siRNA molecules can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In certain embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group. In certain instances, the conjugate is a molecule that facilitates the delivery of the siRNA into a cell.

aiRNA

In certain embodiments, the active agent comprises an asymmetrical interfering RNA (aiRNA). In certain embodiments, aiRNA duplexes of various lengths may be designed with overhangs at the 3' and 5' ends of the antisense strand to target an mRNA of interest. In certain embodiments, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain embodiments, the antisense strand of the aiRNA molecule is about 15-60, 15-50, or 15-40 nucleotides in length, or about 15-30, 15-25, or 19-25 nucleotides in length, or about 20-24, 21-22, or 21-23 nucleotides in length.

In certain embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain embodiments, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In certain embodiments, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In certain embodiments, aiRNA molecules may be used to silence the expression of any of a target gene.

In certain embodiments, the aiRNA molecule comprises a double-stranded (duplex) region of about 10 to about 25 (base paired) nucleotides in length, wherein the aiRNA molecule comprises an antisense strand comprising 5' and 3' overhangs, and wherein the aiRNA molecule is capable of silencing target gene expression.

In certain embodiments, each of the 5' and 3' overhangs on the antisense strand comprises or consists of one, two, three, four, five, six, seven, or more nucleotides.

In certain embodiments, the aiRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof.

miRNA

In certain embodiments, the active agent comprises a microRNAs (miRNA). Generally, miRNA are single-stranded RNA molecules of about 21-23 nucleotides in length, which regulate gene expression. In certain embodiments, the miRNA molecules described herein are about 15-100, 15-90, 15-80, 15-75, 15-70, 15-60, 15-50, or 15-40 nucleotides in length, or about 15-30, 15-25, or 19-25 nucleotides in length, or about 20-24, 21-22, or 21-23 nucleotides in length. In certain embodiments, the miRNA molecule comprises about 15 to about 60 nucleotides in length, wherein the miRNA molecule is capable of silencing target gene expression.

In certain embodiments, miRNA molecules may comprise one or more modified nucleotides. As a non-limiting example, miRNA sequences may comprise one or more of the modified nucleotides described above for siRNA sequences. In certain embodiments, the miRNA molecule comprises 2'OMe nucleotides such as, for example, 2'OMe-guanosine nucleotides, 2'OMe-uridine nucleotides, or mixtures thereof. In certain embodiments, the miRNA molecule comprises modified nucleotides selected from the group consisting of 2'F nucleotides, 2'-deoxy nucleotides, 2'-O-MOE nucleotides, LNA nucleotides, and mixtures thereof.

dsRNA

In certain embodiments, the active agent is a dsRNA (double-stranded RNA). In certain embodiments, the active agent is an shRNA (short hairpin RNA).

Antisense Polynucleotide

In certain embodiments, the active agent is an antisense oligonucleotide. The terms "antisense polynucleotide" or "antisense" include polynucleotides that are complementary to a targeted polynucleotide sequence. Antisense polynucleotides are single strands of DNA or RNA that are complementary to a chosen sequence.

In certain embodiments, the polynucleotide is an antisense RNA. Antisense RNA polynucleotides prevent the translation of complementary RNA strands by binding to the RNA. Antisense DNA polynucleotides can be used to target a specific, complementary (coding or non-coding) RNA. If binding occurs, this DNA/RNA hybrid can be degraded by the enzyme RNase H. In certain embodiments, antisense polynucleotides comprise from about 10 to about 60 nucleotides, or from about 15 to about 30 nucleotides. The term also encompasses antisense polynucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Methods of producing antisense polynucleotides are known in the art and can be readily adapted to produce an antisense polynucleotides that targets any polynucleotide sequence. Selection of antisense polynucleotide sequences specific for a given target sequence is based upon analysis of the chosen target sequence and determination of secondary structure, Tm, binding energy, and relative stability. Antisense polynucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res., 25:3389-402 (1997)).

Ribozymes

In certain embodiments, the active agent is a ribozyme. Ribozymes are RNA-protein complexes having specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction.

The enzymatic nucleic acid molecule may be formed in a hammerhead, hairpin, hepatitis δ virus, group I intron or RNaseP RNA (in association with an RNA guide sequence), or *Neurospora* VS RNA motif, for example. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule.

Methods of producing a ribozyme targeted to any polynucleotide sequence are known in the art. Ribozyme activity can be optimized by altering the length of the ribozyme binding arms or chemically synthesizing ribozymes with modifications that prevent their degradation by serum ribonucleases, modifications which enhance their efficacy in cells, and removal of stem II bases to shorten RNA synthesis times and reduce chemical requirements.

Insecticides

In certain embodiments, an insecticide for killing or controlling the proliferation of an insect is combined with the active agent described above. Examples of suitable insecticides include, but are not limited to, those provided in Table 1.

TABLE 1

| | |
|---|---|
| chloronicotinyls/ neonicotinoids | acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, acetylcholinesterase (AChE) inhibitors (such as carbamates and organophosphates) |
| carbamates | alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb |
| organophosphates | acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion |
| pyrethroids | acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum) |
| oxadiazines | indoxacarb, acetylcholine receptor modulators (such as spinosyns) |
| spinosyns | spinosad |
| cyclodiene organochlorines | camphechlor, chlordane, endosulfan, gamma-HCH, HCH, heptachlor, lindane, methoxychlor |
| fiproles | acetoprole, ethiprole, vaniliprole, fipronil |
| mectins | abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene |
| diacylhydrazines | chromafenozide, halofenozide, methoxyfenozide, tebufenozide |
| benzoylureas | bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron |
| organotins | azocyclotin, cyhexatin, fenbutatin oxide |
| pyrroles | chlorfenapyr |
| dinitrophenols | binapacyrl, dinobuton, dinocap, DNOC |
| METIs | fenazaquin, fenpyroximate, pyrimidifen, pyridaben, tebufenpyrad, tolfenpyrad, rotenone, acequinocyl, fluacrypyrim, microbial disrupters of |

TABLE 1-continued

| | |
|---|---|
| | the intestinal membrane of insects (such as *Bacillus thuringiensis* strains), inhibitors of lipid synthesis (such as tetronic acids and tetramic acids) |
| tetronic acids | spirodiclofen, spiromesifen, spirotetramat |
| tetramic acids | cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester; CAS Reg. No.: 382608-10-8), carboxamides (such as flonicamid), octopaminergic agonists (such as amitraz), inhibitors of the magnesium-stimulated ATPase (such as propargite), ryanodin receptor agonists (such as phthalamides or rynaxapyr) |
| phthalamides | $N_2$-[1,1-dimethyl-2-(methylsulphonyl)ethyl]-3-iodo-$N_1$-[2-methyl--4-[1,2,2,2-tetrafluoro-1-(trifluoromethyl)ethyl]phenyl]-1,2-benzenedicarboxamide (i.e., flubendiamide; CAS reg. No.: 272451-65-7) |

Additional non-limiting examples of suitable insecticides include biologics, hormones or pheromones such as azadirachtin, *Bacillus* species, *Beauveria* species, codlemone, *Metarrhizium* species, *Paecilomyces* species, *thuringiensis* and *Verticillium* species, and active compounds having unknown or non-specified mechanisms of action such as fumigants (such as aluminium phosphide, methyl bromide and sulphuryl fluoride) and selective feeding inhibitors (such as cryolite, flonicamid and pymetrozine). Examples of mite growth inhibitors include, but are not limited to, clofentezine, etoxazole and hexythiazox, amidoflumet, benclothiaz, benzoximate, bifenazate, bromopropylate, buprofezin, chinomethioat, chlordimeform, chlorobenzilate, chloropicrin, clothiazoben, cyclopene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octa-ne-3-carbonitrile (CAS reg. No. 185982-80-3) and the corresponding 3-endo isomer (CAS reg. No. 185984-60-5) (cf. WO 96/37494, WO 98/25923), and also preparations comprising insecticidally effective plant extracts, nematodes, fungi, or viruses.

Herbicides

In certain embodiments, an herbicide for killing or controlling the proliferation of weeds and other unwanted plants is combined with one the active agent described above. Examples of herbicides include, but are not limited to, benzoic acid herbicides such as dicamba esters, phenoxyalkanoic acid herbicides such as 2,4-D, MCPA and 2,4-DB esters, aryloxyphenoxypropionic acid herbicides such as clodinafop, cyhalofop, fenoxaprop, fluazifop, haloxyfop and quizalofop esters, pyridinecarboxylic acid herbicides such as aminopyralid, picloram and clopyralid esters, pyrimidinecarboxylic acid herbicides such as aminocyclopyrachlor esters, pyridyloxyalkanoic acid herbicides such as fluoroxypyr and triclopyr esters, and hydroxybenzonitrile herbicides such as bromoxynil and ioxynil esters, esters of the arylpyridine carboxylic acids and arylpyrimidine carboxylic acids of the following generic structures as disclosed in U.S. Pat. No. 7,314,849, U.S. Pat. No. 7,300,907 and U.S. Pat. No. 7,642,220.

Fungicides

In certain embodiments, a fungicide for killing or controlling the proliferation of a fungus is combined with the active agent described above. Exemplary fungicides include, but are not limited to, strobilurins, azoxystrobin, dimoxystrobin, enestroburin, fluoxastrobin, kresoxim-methyl, metominostrobin, picoxystrobin, pyraclostrobin, trifloxystrobin, orysastrobin, carboxamides, carboxanilides, benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M (mefenoxam), methfuroxam, metsulfovax, ofurace, oxadixyl, oxycarboxin, penthiopyrad, pyracarbolid, salicylanilide, tecloftalam, thifluzamide, tiadinil, N-biphenylamides, bixafen, boscalid, carboxylic acid morpholides, dimethomorph, flumorph, benzamides, flumetover, fluopicolid (picobenzamid), zoxamid, carboxamides, carpropamid, diclocymet, mandipropamid, silthiofam, azoles, triazoles, bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, Imidazoles, cyazofamid, imazalil, pefurazoate, prochloraz, triflumizole, benzimidazoles, benomyl, carbendazim, fuberidazole, thiabendazole, ethaboxam, etridiazole, hymexazol, nitrogen-containing heterocyclyl compounds, pyridines, fuazinam, pyrifenox, pyrimidines, bupirimate, cyprodinil, ferimzone, fenarimol, mepanipyrim, nuarimol, pyrimethanil, piperazines, triforine, pyrroles, fludioxonil, fenpiclonil, morpholines, aldimorph, dodemorph, fenpropimorph, tridemorph, dicarboximides, iprodione, procymidone, vinclozolin, acibenzolar-S-methyl, anilazine, captan, captafol, dazomet, diclomezin, fenoxanil, folpet, fenpropidin, famoxadon, fenamidon, octhilinone, probenazole, proquinazid, pyroquilon, quinoxyfen, tricyclazole, carbamates, dithiocarbamates, ferbam, mancozeb, maneb, metiram, metam, propineb, thiram, zineb, ziram, diethofencarb, flubenthiavalicarb, iprovalicarb, propamocarb, guanidines, dodine, iminoctadine, guazatine, kasugamycin, polyoxins, streptomycin, validamycin A, organometallic compounds, fentin salts, sulfur-containing heterocyclyl compounds, isoprothiolane, dithianone, organophosphorous compounds, edifenphos, fosetyl, fosetyl-aluminum, iprobenfos, pyrazophos, tolclofos-methyl, Organochlorine compounds, thiophanate-methyl, chlorothalonil, dichlofluanid, tolylfluanid, flusulfamide, phthalide, hexachlorobenzene, pencycuron, quintozene, nitrophenyl derivatives, binapacryl, dinocap, dinobuton, spiroxamine, cyflufenamid, cymoxanil, metrafenon, N-2-cyanophenyl-3,4-dichloroisothiazol-5-carboxamide (isotianil), N-(3',4',5'-trifluorobiphenyl-2-yl)-3-difluoromethyl-1-methylpyrazole-4-carboxamide, 3-[5-(4-chlorophenyl)-2,3-dimethylisoxazolidin-3-yl]-pyridine, N-(3',4'-dichloro-4-fluorobiphenyl-2-yl)-3-difluoromethyl-1-methylpyrazole-4-carboxamide, 5-chloro-7-(4-methylpiperidin-1-yl)-6-(2,4,6-trifluorophenyl)-[1,2,4]triazolo[1,5-a] pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide, methyl-(2-chloro-5-[1-(3- methylbenzyloxyimino)-ethyl]benzyl)carbamate, methyl-(2-chloro-5-[1-(6-methylpyridin-2-ylmethoxy-imino)ethyl]benzyl)carbamate, methyl 3-(4-chlorophenyl)-3-(2-isopropoxycarbonylamino-3-methylbutyryl-amino) propionate, 4-fluorophenyl N-(1-(1-(4-cyanophenyl) ethanesulfonyl)but-2-yl)carbamate, N-(2-(4-[3-(4-chlorophenyl)prop-2-ynyloxy]-3-methoxyphenyl)ethyl)-2-metha-nesulfonylamino-3-methylbutyramide, N-(2-(4-[3-(4-chlorophenyl)prop-2-ynyloxy]-3-methoxyphenyl)ethyl)-2-ethan-esulfonylamino-3-methylbutyramide, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylthiazol-5-carboxamide, and methyl 2-(ortho-((2,5-dimethylphenyloxy-methylene)phenyl)-3-methoxyacrylate.

Target Organisms

In certain embodiments, the target organism is any organism in which one or more genes is regulated by the active agent. For example, in some embodiments, the target organism is an organism comprising one or more genes that is targeted by an oligonucleotide or polynucleotide active agent. In some embodiments, the target organism is a plant in which one or more yield-related traits is improved by the active agent. In some embodiments, the target organism is a beneficial insect whose growth, fecundity, or disease resistance is improved by the active agent. In certain embodiments, the target organisms are plant pests or pathogens whose damage to the plant can be reduced or eliminated by active agents according to the invention. Examples of plant pests and pathogens include, but are not limited to, insects, nematodes, fungi, bacteria, viruses, and parasitic plants such as striga, dodder, and mistletoe. Insect pests that may be targeted according to the invention include, but are not limited to, chewing, sucking, and boring insects that belong, for example, to the non-limiting Orders Coleoptera, Diptera, Hemiptera, Heteroptera, Homoptera, Hymenoptera, Lepidoptera, and Orthoptera.

Insects

In some embodiments the composition may be taken up by an insect by direct contact with the composition, for example, by topical adsorption or inhalation of the composition or by direct feeding on a bait comprising the composition, as described below. The compositions may also be taken up by the insect by direct feeding on a plant that has been treated with the composition. Examples of insect pests that may be targeted by the invention include, but are not limited to, those provided in Table 2.

TABLE 2

| Latin Name | Common Name |
| --- | --- |
| Ostrinia nubilalis | European corn borer |
| Helicoverpa zea | Corn earworm |
| Spodoptera exigua | Beet armyworm |
| Spodoptera frugiperda | Fall armyworm |
| Diatraea grandiosella | Southwestern corn borer |
| Elasmopalpus lignosellus | Lesser cornstalk borer |
| Papaipema nebris | Stalk borer |
| Pseudaletia unipuncta | Common armyworm |
| Agrotis ipsilon | Black cutworm |
| Striacosta albicosta | Western bean cutworm |
| Spodoptera ornithogalli | Yellowstriped armyworm |
| Spodoptera praefica | Western yellowstriped armyworm |
| Spodoptera eridania | Southern armyworm |
| Spodoptera eridania | Southern armyworm |
| Peridroma saucia | Variegated cutworm |
| Papaipema nebris | Stalk borer |
| Trichoplusia ni | Cabbage looper |

TABLE 2-continued

| Latin Name | Common Name |
| --- | --- |
| Keiferia lycopersicella | Tomato pinworm |
| Manduca sexta | Tobacco hornworm |
| Manduca quinquemaculata | Tomato hornworm |
| Artogeia rapae | Imported cabbageworm |
| Pieris brassicae | Cabbage butterfly |
| Trichoplusia ni | Cabbage looper |
| Plutella xylostella | Diamondback moth |
| Spodoptera exigua | Beet armyworm |
| Agrotis segetum | Common cutworm |
| Phthorimaea operculella | Potato tuberworm |
| Plutella xylostella | Diamondback moth |
| Diatraea saccharalis | Sugarcane borer |
| Crymodes devastator | Glassy cutworm |
| Feltia ducens | Dingy cutworm |
| Agrotis gladiaria | Claybacked cutworm |
| Plathypena scabra | Green cloverworm |
| Pseudoplusia includes | Soybean looper |
| Anticarsia gemmatalis | Velvetbean caterpillar |
| Coleoptera Diabrotica barberi | Northern corn rootworm |
| Diabrotica undecimpunctata | Southern corn rootworm |
| Diabrotica virgifera | Western corn rootworm |
| Sitophilus zeamais | Maize weevil |
| Leptinotarsa decemlineata | Colorado potato beetle |
| Epitrix hirtipennis | Tobacco flea beetle |
| Phyllotreta cruciferae | Crucifer flea beetle |
| Phyllotreta pusilla | Western black flea beetle |
| Anthonomus eugenii | Pepper weevil |
| Leptinotarsa decemlineata | Colorado potato beetle |
| Epitrix cucumeris | Potato flea beetle |
| Hemicrepidus memnonius | Wireworms Melanpotus spp. |
| Ceutorhychus assimilis | Wireworms |
| Phyllotreta cruciferae | Cabbage seedpod weevil |
| Melanolus spp. | Crucifer flea beetle |
| Aeolus mellillus | Wireworm |
| Aeolus mancus | Wheat wireworm |
| Horistonotus uhlerii | Sand wireworm |
| Sphenophorus maidis | Maize billbug |
| Sphenophorus zeae | Timothy bilibug |
| Sphenophorus parvulus | Bluegrass billbug |
| Sphenophorus callosus | Southern corn billbug |
| Phyllophaga spp. | White grubs |
| Chaetocnema pulicaria | Corn flea beetle |
| Popillia japonica | Japanese beetle |
| Epilachna varivestis | Mexican bean beetle |
| Cerotoma trifurcate | Bean leaf beetle |
| Epicauta pestifera Epicauta lemniscata | Blister beetles |
| Homoptera Rhopalosiphum maidis | Corn leaf aphid |
| Anuraphis maidiradicis | Corn root aphid |
| Myzus persicae | Green peach aphid |
| Macrosiphum euphorbiae | Potato aphid |
| Trileurodes vaporariorum | Greenhouse whitefly |
| Bemisia tabaci | Sweetpotato whitefly |
| Bemisia argentifolii | Silverleaf whitefly |
| Brevicoryne brassicae | Cabbage aphid |
| Myzus persicae | Green peach aphid |
| Empoasca fabae | Potato leafhopper |
| Paratrioza cockerelli | Potato psyllid |
| Bemisia argentifolii | Silverleaf whitefly |
| Bemisia tabaci | Sweetpotato whitefly |
| Cavariella aegopodii | Carrot aphid |
| Brevicoryne brassicae | Cabbage aphid |
| Saccharosydne saccharivora | West Indian canefly |
| Sipha flava | Yellow sugarcane aphid |
| Spissistilus festinus | Threecornered alfalfa hopper |
| Hemiptera Lygus lineolaris | Lygus hesperus |
| Lygus rugulipennis | Lygus bug |
| Acrosternum hilare | Green stink bug |
| Euschistus servus | Brown stick bug |
| Blissus leucopterus leucopterus | Chinch bug |
| Diptera Liriomyza trifolii | Leafminer |
| Liriomyza sativae | Vegetable leafminer |
| Scrobipalpula absoluta | Tomato leafminer |
| Delia platura | Seedcorn maggot |
| Delia brassicae | Cabbage maggot |
| Delia radicum | Cabbage root fly |
| Psila rosae | Carrot rust fly |
| Tetanops myopaeformis | Sugarbeet root maggot |
| Orthoptera Melanoplus differentialis | Differential grasshopper |

TABLE 2-continued

| Latin Name | Common Name |
| --- | --- |
| *Melanoplus femurrubrum* | Redlegged grasshopper |
| *Melanoplus bivittatus* | Twostriped grasshopper |

Nematodes

Examples of nematodes that may be targeted include, but are not limited to, those provided in Table 3.

TABLE 3

| Disease | Causative Agent |
| --- | --- |
| Awl | *Dolichoderus* spp., *D. heterocephalus* |
| Bulb and stem (Europe) | *Ditylenchus dipsaci* |
| Burrowing | *Radopholus similes R. similis* |
| Cyst | *Heterodera avenae, H. zeae, H. schachti*; *Globodera rostochiensis, G. pallida,* and *G. tabacum*; *Heterodera trifolii, H. medicaginis, H. ciceri, H. mediterranea, H. cyperi, H. salixophila, H. zeae, H. goettingiana, H. riparia, H. humuli, H. latipons, H. sorghi, H. fici, H. litoralis,* and *H. turcomanica*; *Punctodera chalcoensis* |
| Dagger | *Xiphinema* spp., *X. americanum, X. Mediterraneum* |
| False root-knot | *Nacobbus dorsalis* |
| Lance, Columbia | *Hoplolaimus Columbus* |
| Lance | *Hoplolaimus* spp., *H. galeatus* |
| Lesion | *Pratylenchus* spp., *P. brachyurus, P. coffeae P. crenatus, P. hexincisus, P. neglectus, P. penetrans, P. scribneri, P. magnica, P. neglectus, P. thornei, P. vulnus, P. zeae* |
| Needle | *Longidorus* spp., *L. breviannulatus* |
| Ring | *Criconemella* spp., *C. ornata* |
| Root-knot | *Meloidogyne* spp., *M. arenaria, M. chitwoodi, M. artiellia, M. fallax, M. hapla, M. javanica, M. incognita, M. microtyla, M. partityla, M. panyuensis, M. paranaensis* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |
| Others | *Hirschmanniella* species, *Pratylenchoid magnicauda* |

Fungi

Examples of fungi that may be targeted include, but are not limited to, those provided in Table 4.

TABLE 4

| Disease | Causative Agent |
| --- | --- |
| Brown stripe downy mildew | *Sclerophthora rayssiae* var. zeae |
| Crazy top downy mildew | *Sclerophthora macrospora = S. macrospora* |
| Green ear downy mildew | *Sclerospora graminicola* |
| Java downy mildew | *Peronosclerospora maydis = Sclerospora maydis* |
| Philippine downy mildew | *Peronosclerospora philippinensis = Sclerospora philippinensis* |
| Sorghum downy mildew | *Peronosclerospora sorghi = Sclerospora sorghi* |
| Spontaneum downy mildew | *Peronosclerospora spontanea = Sclerospora spontanea* |
| Sugarcane downy mildew | *Peronosclerospora sacchari = Sclerospora sacchari* |
| Dry ear rot (cob, kernel and stalk rot) | *Nigrospora oryzae* (teleomorph: *Khuskia oryzae*) |
| Ear rots, minor | *Aspergillus glaucus, A. niger, Aspergillus* spp., *Cunninghamella* sp., *Curvularia pallescens, Doratomyces stemonitis = Cephalotrichum stemonitis, Fusarium culmorum, Gonatobotrys simplex, Pithomyces maydicus, Rhizopus microsporus, R. stolonifer = R. nigricans, Scopulariopsis brumptii* |
| Ergot (horse's tooth, diente del caballo) | *Claviceps gigantea* (anamorph: *Sphacelia* sp.) |
| Eyespot | *Aureobasidium zeae = Kabatiella zeae* |
| *Fusarium* ear and stalk rot | *Fusarium subglutinans = F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |

TABLE 4-continued

| Disease | Causative Agent |
| --- | --- |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria*) |
| *Hormodendrum* ear rot (*Cladosporium* rot) | *Cladosporium cladosporioides* = *Hormodendrum cladosporioides*, *C. herbarum* (teleomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zein* |
| Northern corn leaf blight | *Exserohilum turcicum* = *Helminthosporium turcicum*, *Setosphaeria turcica* |
| Northern corn leaf spot | *Cochliobolus carbonum* |
| *Helminthosporium* ear rot (race 1) | *Bipolaris zeicola* = *Helminthosporium carbonum* |
| *Penicillium* ear rot (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, *Phaeocytosporella zeae* |
| *Phaeosphaeria* leaf spot | *Phaeosphaeria maydis*, *Sphaerulina maydis* |
| *Physalospora* ear rot | *Botryosphaeria Botryosphaeria festucae* = *Physalospora zeicola*, (anamorph: *Diplodia frumenti*) |
| Purple leaf sheath | *Hemiparasitic* bacteria and fungi |
| *Pyrenochaeta* stalk rot and root rot | *Phoma terrestris*, *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot | *Rhizoctonia zeae* (teleomorph: *Waitea circinata*) |
| *Rhizoctonia* root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *F. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (leaf disease, ear and, stalk rot) | *Setosphaeria rostrata*, *Helminthosporium* (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiospora zeae* |
| *Sclerotium* ear rot (southern blight) | *Sclerotium rolfsii* (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicellatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M. rubber* |
| Smut, common | *Ustilago zeae* = *U. maydis* |
| Smut, false | *Ustilaginoidea virens* |
| Smut, head | *Sphacelotheca reiliana* = *Sporisorium holci-sorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium episphaeria*, *F. merismoides*, *F. oxysporum*, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |

TABLE 4-continued

| Disease | Causative Agent |
|---|---|
| Tar spot | *Phyllachora maydis* |
| *Trichoderma* ear rot and root rot | *Trichoderma viride* = *T. lignorum* (teleomorph: *Hypocrea* sp.) |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |
| Anthracnose leaf blight and stalk rot | *Colletotrichum graminicola anthracnose* (teleomorph: *Glomerella graminicola*), *Glomerella tucumanensis* (anamorph: *Glomerella falcatum*) |
| *Aspergillus* ear and kernel rot | *Aspergillus flavus* |
| Banded leaf and sheath spot | *Rhizoctonia solani* = *Rhizoctonia microsclerotia* (teleomorph: *Thanatephorus cucumeris*) |
| Black bundle disease | *Acremonium strictum* = *Cephalosporium acremonium* |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitialis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or leaf streak | *Stenocarpella macrospora* = *Diplodia macrospore* |
| Corn common rust | *Puccinia sorghi* |
| Corn southern rust | *Puccinia polysora* |
| Corn tropical rust | *Physopella pallescens*, *P. zeae* = *Angiospora zeae* |
| Oat crown rust | *Puccinia coronata* |
| Oat stem Rust | *Puccinia graminis* |
| Stem rust | *Puccinia graminis* = *P. graminis f.* sp. *secalis* |
| Leaf (brown) rust | *Puccinia recondita* (anamorph: *Aecidium clematitis*) |
| Sugarcane common rust | *Puccinia melanocephala* = *P. eriantha* |
| Wheat leaf (brown) rust | *Puccinia triticina* = *P. Recondita f.* Sp. tritici = *P. tritici-duri* |
| Wheat stem (black) rust | *Puccinia graminis* = *P. graminis f.* sp. *tritici* |
| Wheat stripe (yellow) rust | *Puccinia striiformis* (anamorph: *P. uredoglumarum*) |
| Bean rust | *Uromyces appendiculatus* |
| Cotton rust | *Puccinia schedonnardi* |
| Cotton southwestern rust | *Puccinia cacabata* |
| Cotton tropical rust | *Phakopsora gossypii* |
| Peanut rust | *Puccinia arachidis* |
| Potato common rust | *Puccinia pittierianap* |
| Potato deforming rust | *Aecidium cantensis* |
| Soybean rust | *Phakopsora pachyrhizi* |

Bacteria

Examples of bacteria that may be targeted include, but are not limited to, those shown in Table 5.

TABLE 5

| Disease | Causative Agent |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *Zeae* |
| Bacterial stripe | *Pseudomonas andropogonis* |
| Chocolate spot | *Pseudomonas syringae* pv. *Coronafaciens* |
| Goss's bacterial wilt blight (leaf freckles and wilt) | *Clavibacter michiganensis* subsp. *nebraskensis* = *Cornebacterium michiganense* pv. *Nebraskense* |
| Holcus spot | *Pseudomonas syringae* pv. *Syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (Mesa Central or Rio Grande stunt) | *Achapparramiento*, stunt, *Spiroplasma kunkelii* |

Viruses

Examples of plant viruses that may be targeted include, but are not limited to, those shown in the Table 6.

TABLE 6

| | |
|---|---|
| *Alfamoviruses*: Bromoviridae | *Alfalfa mosaic alfamovirus* |
| *Alphacryptoviruses*: Partitiviridae | *Alfalfa 1 alphacryptovirus, Beet 1 alphacryptovirus, Beet 2 alphacryptovirus, Beet 3 alphacryptovirus, Carnation 1 alphacryptovirus, Carrot temperate 1 alphacryptovirus, Carrot temperate 3 alphacryptovirus, Carrot temperate 4 alphacryptovirus, Cocksfoot alphacryptovirus, Hop trefoil 1 alphacryptovirus, Hop trefoil 3 alphacryptovirus, Radish yellow edge alphacryptovirus, Ryegrass alphacryptovirus, Spinach temperate alphacryptovirus, Vicia alphacryptovirus, White clover 1 alphacryptovirus, White clover 3 alphacryptovirus* |
| *Badnaviruses* | *Banana streak badnavirus, Cacao swollen shoot badnavirus, Canna yellow mottle badnavirus, Commelina yellow mottle badnavirus, Dioscorea bacilliform badnavirus, Kalanchoe top-spotting badnavirus, Rice tungro bacilliform badnavirus, Schefflera ringspot badnavirus, Sugarcane bacilliform badnavirus* |
| *Betacryptoviruses*: Partitiviridae | *Carrot temperate 2 betacryptovirus, Hop trefoil 2 betacryptovirus, Red clover 2 betacryptovirus, White clover 2 betacryptovirus* |
| *Bigeminiviruses*: Geminiviridae | *Abutilon mosaic bigeminivirus, Ageratum yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomate bigeminivirus, Cotton leaf crumple bigeminivirus, Cotton leaf curl bigeminivirus, Croton yellow vein mosaic bigeminivirus, Dolichos yellow mosaic bigeminivirus, Euphorbia mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigeminivirus, Rhynchosia mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus, Watermelon curly mottle bigeminivirus* |
| *Bromoviruses*: Bromoviridae | *Broad bean mottle bromovirus, Brome mosaic bromovirus, Cassia yellow blotch bromovirus, Cowpea chlorotic mottle bromovirus, Melandrium yellow fleck bromovirus, Spring beauty latent bromovirus* |
| *Bymoviruses*: Potyviridae | *Barley mild mosaic bymovirus, Barley yellow mosaic bymovirus, Oat mosaic bymovirus, Rice necrosis mosaic bymovirus, Wheat spindle streak mosaic bymovirus, Wheat yellow mosaic bymovirus* |
| *Capilloviruses* | *Apple stem grooving capillovirus, Cherry A capillovirus, Citrus tatter leaf capillovirus, Lilac chlorotic leafspot capillovirus* |
| *Carlaviruses* | *Blueberry scorch carlavirus, Cactus 2 carlavirus, Caper latent carlavirus, Carnation latent carlavirus, Chrysanthemum B carlavirus, Dandelion latent carlavirus, Elderberry carlavirus, Fig S carlavirus, Helenium S carlavirus, Honeysuckle latent carlavirus, Hop American latent carlavirus, Hop latent carlavirus, Hop mosaic carlavirus, Kalanchoe latent carlavirus, Lilac mottle carlavirus, Lily symptomless carlavirus, Mulberry latent carlavirus, Muskmelon vein necrosis carlavirus, Nerine latent carlavirus, Passiflora latent carlavirus, Pea streak carlavirus, Poplar mosaic carlavirus, Potato M carlavirus, Potato S carlavirus, Red clover vein mosaic carlavirus, Shallot latent carlavirus, Strawberry pseudo mild yellow edge carlavirus* |
| *Carmoviruses*: Tombusviridae | *Bean mild mosaic carmovirus, Cardamine chlorotic fleck carmovirus, Carnation mottle carmovirus, Cucumber leaf spot carmovirus, Cucumber soil-borne carmovirus, Galinsoga mosaic carmovirus, Hibiscus chlorotic ringspot carmovirus, Melon necrotic spot carmovirus, Pelargonium flower break carmovirus, Turnip crinkle carmovirus* |
| *Caulimoviruses* | *Blueberry red ringspot caulimovirus, Carnation etched ring caulimovirus, Cauliflower mosaic caulimovirus, Dahlia mosaic caumovirus, Figwort mosaic caulimovirus, Horseradish latent caulimovirus, Mirabilis mosaic caulimovirus, Peanut chlorotic streak caulimovirus, Soybean chlorotic mottle caulimovirus, Sweet potato caulimovirus, Thistle mottle caulimovirus* |
| *Closteroviruses* | *Beet yellow stunt closterovirus, Beet yellows closterovirus, Broad bean severe chlorosis closterovirus, Burdock yellows closterovirus, Carnation necrotic fleck closterovirus, Citrus tristeza closterovirus, Clover yellows closterovirus, Grapevine stem pitting associated closterovirus, Wheat yellow leaf closterovirus* |
| *Comoviruses*: Comoviridae | *Bean pod mottle comovirus, Bean rugose mosaic comovirus, Broad bean stain comovirus, Broad bean true mosaic comovirus, Cowpea mosaic comovirus, Cowpea severe mosaic comovirus, Glycine* |

TABLE 6-continued

| | |
|---|---|
| | *mosaic comovirus, Pea mild mosaic comovirus, Potato Andean mottle comovirus, Quail pea mosaic comovirus, Radish mosaic comovirus, Red clover mottle comovirus, Squash mosaic comovirus, Ullucus C comovirus* |
| *Cucumoviruses*: Bromoviridae | *Cucumber mosaic cucumovirus, Peanut stunt cucumovirus, Tomato aspermy cucumovirus* |
| *Cytorhabdoviruses*: Rhabdoviridae | *Barley yellow striate mosaic cytorhabdovirus, Broad bean yellow vein cytorhabdovirus, Broccoli necrotic yellows cytorhabdovirus, Cereal northern mosaic cytorhabdovirus, Festuca leaf streak cytorhabdovirus, Lettuce necrotic yellows cytorhabdovirus, Sonchus cytorhabdovirus, Strawberry crinkle cytorhabdovirus* |
| *Dianthoviruses* | *Carnation ringspot dianthovirus, Red clover necrotic mosaic dianthovirus, Sweet clover necrotic mosaic dianthovirus* |
| *Enamoviruses* | *Pea enation mosaic enamovirus* |
| *Fijiviruses*: Reoviridae | *Maize rough dwarf fijivirus, Oat sterile dwarf fijivirus, Pangola stunt fijivirus, Rice black-streaked dwarf fijivirus, Sugarcane Fiji disease fijivirus* |
| *Furoviruses* | *Beet necrotic yellow vein furovirus, Beet soil-borne furovirus, Broad bean necrosis furovirus, Oat golden stripe furovirus, Peanut clump furovirus, Potato mop-top furovirus, Sorghum chlorotic spot furovirus, Wheat soil-borne mosaic furovirus* |
| *Hordeiviruses* | *Anthoxanthum latent blanching hordeivirus, Barley stripe mosaic hordeivirus, Lychnis ringspot hordeivirus, Poa semilatent hordeivirus* |
| *Hybrigeminiviruses*: Geminiviridae | *Beet curly top hybrigeminivirus, Tomato pseudo curly top hybrigeminivirus* |
| *Idaeoviruses* | *Raspberry bushy dwarf idaeovirus* |
| *Ilarviruses*: Bromoviridae | *Apple mosaic ilarvirus, Asparagus 2 ilarvirus, Blueberry necrotic shock ilarvirus, Citrus leaf rugose ilarvirus, Citrus variegation ilarvirus, Elm mottle ilarvirus, Humulus japonicus ilarvirus, Hydrangea mosaic ilarvirus, Lilac ring mottle ilarvirus, Parietaria mottle ilarvirus, Plum American line pattern ilarvirus, Prune dwarf ilarvirus, Prunus necrotic ringspot ilarvirus, Spinach latent ilarvirus, Tobacco streak ilarvirus, Tulare apple mosaic ilarvirus* |
| *Ipomoviruses*: Potyviridae | *Sweet potato mild mottle ipomovirus, Sweet potato yellow dwarf ipomovirus* |
| *Luteoviruses* | *Barley yellow dwarf luteovirus, Bean leaf roll luteovirus, Beet mild yellowing luteovirus, Beet western yellows luteovirus, Carrot red leaf luteovirus, Groundnut rosette assistor luteovirus, Potato leafroll luteovirus, Solanum yellows luteovirus, Soybean dwarf luteovirus, Soybean Indonesian dwarf luteovirus, Strawberry mild yellow edge luteovirus, Subterranean clover red leaf luteovirus, Tobacco necrotic dwarf luteovirus* |
| *Machlomoviruses* | *Maize chlorotic mottle machlomovirus* |
| *Macluraviruses* | *Maclura mosaic macluravirus, Narcissus latent macluravirus* |
| *Marafiviruses* | *Bermuda grass etched-line marafivirus, Maize rayado fino marafivirus, Oat blue dwarf marafivirus* |
| *Monogeminiviruses*: Geminiviridae | *Chloris striate mosaic monogeminivirus, Digitaria striate mosaic monogeminivirus, Digitaria streak monogeminivirus, Maize streak monogeminivirus, Miscanthus streak monogeminivirus, Panicum streak monogeminivirus, Paspalum striate mosaic monogeminivirus, Sugarcane streak monogeminivirus, Tobacco yellow dwarf monogeminivirus, Wheat dwarf monogeminivirus* |
| *Nanaviruses* | *Banana bunchy top nanavirus, Coconut foliar decay nanavirus, Faba bean necrotic yellows nanavirus, Milk vetch dwarf nanavirus, Subterranean clover stunt nanavirus* |
| *Necroviruses* | *Tobacco necrosis necrovirus, Carnation yellow stripe necrovirus, Lisianthus necrosis necrovirus* |
| *Nepoviruses*: Comoviridae | *Arabis mosaic nepovirus, Arracacha A nepovirus, Artichoke Italian latent nepovirus, Artichoke yellow ringspot nepovirus, Blueberry leaf mottle nepovirus, Cacao necrosis nepovirus, Cassava green mottle nepovirus, Cherry leaf roll nepovirus, Cherry rasp leaf nepovirus, Chicory yellow mottle nepovirus, Crimson clover latent nepovirus, Cycas necrotic stunt nepovirus, Grapevine Bulgarian latent nepovirus, Grapevine chrome mosaic nepovirus, Grapevine fanleaf nepovirus, Hibiscus latent ringspot nepovirus, Lucerne Australian latent nepovirus, Mulberry ringspot nepovirus, Myrobalan latent ringspot nepovirus, Olive latent ringspot nepovirus, Peach rosette mosaic nepovirus, Potato black ringspot nepovirus, Potato U nepovirus, Raspberry ringspot nepovirus, Tobacco ringspot nepovirus, Tomato black ring nepovirus, Tomato ringspot nepovirus* |
| *Nucleorhabdoviruses*: Rhabdoviridae | *Carrot latent nucleorhabdovirus, Coriander feathery red vein nucleorhabdovirus, Cow parsnip mosaic nucleorhabdovirus, Cynodon chlorotic streak nucleorhabdovirus, Datura yellow vein nucleorhabdovirus, Eggplant mottled dwarf nucleorhabdovirus, Maize mosaic nucleorhabdovirus, Pittosporum vein yellowing nucleorhabdovirus, Potato yellow dwarf nucleorhabdovirus, Sonchus yellow net nucleorhabdovirus, Sowthistle yellow vein* |

TABLE 6-continued

| | |
|---|---|
| | nucleorhabdovirus, Tomato vein clearing nucleorhabdovirus, Wheat American striate mosaic nucleorhabdovirus |
| Oryzaviruses: Reoviridae | Echinochloa ragged stunt oryzavirus, Rice ragged stunt oryzavirus |
| Ourmiaviruses | Cassava Ivorian bacilliform ourmiavirus, Epirus cherry ourmiavirus, Melon Ourmia ourmiavirus, Pelargonium zonate spot ourmiavirus |
| Phytoreoviruses: Reoviridae | Clover wound tumor phytoreovirus, Rice dwarf phytoreovirus, Rice gall dwarf phytoreovirus, Rice bunchy stunt phytoreovirus, Sweet potato phytoreovirus |
| Potexviruses | Asparagus 3 potexvirus, Cactus X potexvirus, Cassava X potexvirus, Chicory X potexvirus, Clover yellow mosaic potexvirus, Commelina X potexvirus, Cymbidium mosaic potexvirus, Daphne X potexvirus, Foxtail mosaic potexvirus, Hydrangea ringspot potexvirus, Lily X potexvirus, Narcissus mosaic potexvirus, Nerine X potexvirus, Papaya mosaic potexvirus, Pepino mosaic potexvirus, Plantago asiatica mosaic potexvirus, Plantain X potexvirus, Potato aucuba mosaic potexvirus, Potato X potexvirus, Tulip X potexvirus, Viola mottle potexvirus, White clover mosaic potexvirus |
| Potyviruses: Potyviridae | Alstroemeria mosaic potyvirus, Amaranthus leaf mottle potyvirus, Araujia mosaic potyvirus, Arracacha Y potyvirus, Artichoke latent potyvirus, Asparagus 1 potyvirus, Banana bract mosaic potyvirus, Bean common mosaic necrosis potyvirus, Bean common mosaic potyvirus, Bean yellow mosaic potyvirus, Beet mosaic potyvirus, Bidens mosaic potyvirus, Bidens mottle potyvirus, Cardamom mosaic potyvirus, Carnation vein mottle potyvirus, Carrot thin leaf potyvirus, Cassava brown streak potyvirus, Cassia yellow spot potyvirus, Celery mosaic potyvirus, Chickpea bushy dwarf potyvirus, Chickpea distortion mosaic potyvirus, Clover yellow vein potyvirus, Commelina diffusa potyvirus, Commelina mosaic potyvirus, Cowpea green vein-banding potyvirus, Cowpea Moroccan aphid-borne mosaic potyvirus, Cowpea rugose mosaic potyvirus, Crinum mosaic potyvirus, Daphne Y potyvirus, Dasheen mosaic potyvirus, Datura Colombian potyvirus, Datura distortion mosaic potyvirus, Datura necrosis potyvirus, Datura shoestring potyvirus, Dendrobium mosaic potyvirus, Desmodium mosaic potyvirus, Dioscorea alata potyvirus, Dioscorea green banding mosaic potyvirus, Eggplant green mosaic potyvirus, Euphorbia ringspot potyvirus, Freesia mosaic potyvirus, Groundnut eyespot potyvirus, Guar symptomless potyvirus, Guinea grass mosaic potyvirus, Helenium Y potyvirus, Henbane mosaic potyvirus, Hippeastrum mosaic potyvirus, Hyacinth mosaic potyvirus, Iris fulva mosaic potyvirus, Iris mild mosaic potyvirus, Iris severe mosaic potyvirus, Johnsongrass mosaic potyvirus, Kennedya Y potyvirus, Leek yellow stripe potyvirus, Lettuce mosaic potyvirus, Lily mottle potyvirus, Maize dwarf mosaic potyvirus, Malva vein clearing potyvirus, Marigold mottle potyvirus, Narcissus yellow stripe potyvirus, Nerine potyvirus, Onion yellow dwarf potyvirus, Ornithogalum mosaic potyvirus, Papaya ringspot potyvirus, Parsnip mosaic potyvirus, Passiflora ringspot potyvirus, Passiflora South African potyvirus, Passionfruit woodiness potyvirus, Patchouli mosaic potyvirus, Pea mosaic potyvirus, Pea seed-borne mosaic potyvirus, Peanut green mosaic potyvirus, Peanut mottle potyvirus, Pepper Indian mottle potyvirus, Pepper mottle potyvirus, Pepper severe mosaic potyvirus, Pepper veinal mottle potyvirus, Plum pox potyvirus, Pokeweed mosaic potyvirus, Potato A potyvirus, Potato V potyvirus, Potato Y potyvirus, Primula mosaic potyvirus, Ranunculus mottle potyvirus, Sorghum mosaic potyvirus, Soybean mosaic potyvirus, Statice Y potyvirus, Sugarcane mosaic potyvirus, Sweet potato feathery mottle potyvirus, Sweet potato G potyvirus, Swordbean distortion mosaic potyvirus, Tamarillo mosaic potyvirus, Telfairia mosaic potyvirus, Tobacco etch potyvirus, Tobacco vein-banding mosaic potyvirus, Tobacco vein mottling potyvirus, Tobacco wilt potyvirus, Tomato Peru potyvirus, Tradescantia-Zebrina potyvirus, Tropaeolum 1 potyvirus, Tropaeolum 2 potyvirus, Tuberose potyvirus, Tulip band-breaking potyvirus, Tulip breaking potyvirus, Tulip chlorotic blotch potyvirus, Turnip mosaic potyvirus, Ullucus mosaic potyvirus, Vallota mosaic potyvirus, Vanilla mosaic potyvirus, Vanilla necrosis potyvirus, Voandzeia distortion mosaic potyvirus, Watermelon mosaic 1 potyvirus, Watermelon mosaic 2 potyvirus, Wild potato mosaic potyvirus, Wisteria vein mosaic potyvirus, Yam mosaic potyvirus, Zucchini yellow fleck potyvirus, Zucchini yellow mosaic potyvirus |
| Rymoviruses: Potyviridae Agropyron mosaic rymovirus | Hordeum mosaic rymovirus, Oat necrotic mottle rymovirus, Ryegrass mosaic rymovirus, Wheat streak mosaic rymovirus |
| Satellite RNAs | Arabis mosaic satellite RNA, Chicory yellow mottle satellite RNA, Cucumber mosaic satellite RNA, Grapevine fanleaf satellite RNA, |

TABLE 6-continued

| | |
|---|---|
| | Strawberry latent ringspot satellite RNA, Tobacco ringspot satellite RNA, Tomato black ring satellite RNA, Velvet tobacco mottle satellite RNA |
| Satelliviruses | Maize white line mosaic satellivirus, Panicum mosaic satellivirus, Tobacco mosaic satellivirus, Tobacco necrosis satellivirus |
| Sequiviruses: Sequiviridae | Dandelion yellow mosaic sequivirus, Parsnip yellow fleck sequivirus |
| Sobemoviruses | Bean southern mosaic sobemovirus, Blueberry shoestring sobemovirus, Cocksfoot mottle sobemovirus, Lucerne transient streak sobemovirus, Rice yellow mottle sobemovirus, Rottboellia yellow mottle sobemovirus, Solanum nodiflorum mottle sobemovirus, Sowbane mosaic sobemovirus, Subterranean clover mottle sobemovirus, Turnip rosette sobemovirus, Velvet tobacco mottle, sobemovirus |
| Tenuiviruses | Maize stripe tenuivirus, Rice grassy stunt tenuivirus, Rice hoja blanca tenuivirus, Rice stripe tenuivirus |
| Tobamoviruses | Cucumber green mottle mosaic tobamovirus, Frangipani mosaic tobamovirus, Kyuri green mottle mosaic tobamovirus, Odontoglossum ringspot tobamovirus, Paprika mild mottle tobamovirus, Pepper mild mottle tobamovirus, Ribgrass mosaic tobamovirus, Opuntia Sammons' tobamovirus, Sunn-hemp mosaic tobamovirus, Tobacco mild green mosaic tobamovirus, Tobacco mosaic tobamovirus, Tomato mosaic tobamovirus, Ullucus mild mottle tobamovirus |
| Tobraviruses | Pea early browning tobravirus, Pepper ringspot tobravirus, Tobacco rattle tobravirus |
| Tombusviruses: Tombusviridae | Artichoke mottled crinkle tombusvirus, Carnation Italian ringspot tombusvirus, Cucumber necrosis tombusvirus, Cymbidium ringspot tombusvirus, Eggplant mottled crinkle tombusvirus, Grapevine Algerian latent tombusvirus, Lato River tombusvirus, Neckar River tombusvirus, Pelargonium leaf curl tombusvirus, Pepper Moroccan tombusvirus, Petunia asteroid mosaic tombusvirus, Tomato bushy stunt tombusvirus |
| Tospoviruses: Bunyaviridae | Impatiens necrotic spot tospovirus, Peanut yellow spot tospovirus, Tomato spotted wilt tospovirus |
| Trichoviruses | Apple chlorotic leaf spot trichovirus, Heracleum latent trichovirus, Potato T trichovirus |
| Tymoviruses | Abelia latent tymovirus, Belladonna mottle tymovirus, Cacao yellow mosaic tymovirus, Clitoria yellow vein tymovirus, Desmodium yellow mottle tymovirus, Dulcamara mottle tymovirus, Eggplant mosaic tymovirus, Erysimum latent tymovirus, Kennedya yellow mosaic tymovirus, Melon rugose mosaic tymovirus, Okra mosaic tymovirus, Ononis yellow mosaic tymovirus, Passionfruit yellow mosaic tymovirus, Physalis mosaic tymovirus, Plantago mottle tymovirus, Potato Andean latent tymovirus, Scrophularia mottle tymovirus, Turnip yellow mosaic, tymovirus, Voandzeia necrotic mosaic tymovirus, Wild cucumber mosaic tymovirus |
| Umbraviruses | Bean yellow vein banding umbravirus, Carrot mottle mimic umbravirus, Carrot mottle umbravirus, Carrot mottle mimic umbravirus, Groundnut rosette umbravirus, Lettuce speckles mottle umbravirus, Tobacco mottle umbravirus |
| Varicosaviruses | Freesia leaf necrosis varicosavirus, Lettuce big-vein varicosavirus, Tobacco stunt varicosavirus |
| Waikaviruses: Sequiviridae | Anthriscus yellows waikavirus, Maize chlorotic dwarf waikavirus, Rice tungro spherical waikavirus |
| Putative Ungrouped Viruses | Alsike clover vein mosaic virus, Alstroemeria streak potyvirus, Amaranthus mosaic potyvirus, Amazon lily mosaic potyvirus, Anthoxanthum mosaic potyvirus, Apple stem pitting virus, Aquilegia potyvirus, Asclepias rhabdovirus, Atropa belladonna rhabdovirus, Barley mosaic virus, Barley yellow streak mosaic virus, Beet distortion mosaic virus, Beet leaf curl rhabdovirus, Beet western yellows ST9-associated RNA virus, Black raspberry necrosis virus, Bramble yellow mosaic potyvirus, Brinjal mild mosaic potyvirus, Broad bean B virus, Broad bean V potyvirus, Broad bean yellow ringspot virus, Bryonia mottle potyvirus, Burdock mosaic virus, Burdock mottle virus, Callistephus chinensis chlorosis rhabdovirus, Canary reed mosaic potyvirus, Canavalia maritima mosaic potyvirus, Carnation rhabdovirus, Carrot mosaic potyvirus, Cassava symptomless rhabdovirus, Cassia mosaic virus, Cassia ringspot virus, Celery yellow mosaic potyvirus, Celery yellow net virus, Cereal flame chlorosis virus, Chickpea filiform potyvirus, Chilli veinal mottle potyvirus, Chrysanthemum spot potyvirus, Chrysanthemum vein chlorosis rhabdovirus, Citrus leprosis rhabdovirus, Citrus ringspot virus, Clover mild mosaic virus, Cocksfoot streak potyvirus, Colocasia bobone disease rhabdovirus, Cucumber toad-skin rhabdovirus, Cucumber vein yellowing virus, Cypripedium calceolus potyvirus, Datura innoxia Hungarian mosaic potyvirus, Dioscorea trifida potyvirus, Dock mottling mosaic potyvirus, Dodonaea yellows-associated virus, Eggplant severe mottle potyvirus, Euonymus fasciation |

TABLE 6-continued rhabdovirus, Euonymus rhabdovirus, Fern potyvirus, Fig potyvirus, Gerbera symptomless rhabdovirus, Grapevine fleck virus, Grapevine stunt virus, Guar top necrosis virus, Habenaria mosaic potyvirus, Holcus lanatus yellowing rhabdovirus, Holcus streak potyvirus, Iris germanica leaf stripe rhabdovirus, Iris Japanese necrotic ring virus, Isachne mosaic potyvirus, Kalanchoe isometric virus, Kenaf vein-clearing rhabdovirus, Launaea mosaic potyvirus, Lupin yellow vein rhabdovirus, Maize eyespot virus, Maize line virus, Maize mottle/chlorotic stunt virus, Maize white line mosaic virus, Malvastrum mottle virus, Melilotus mosaic potyvirus, Melon vein-banding mosaic potyvirus, Melothria mottle potyvirus, Mimosa mosaic virus, Mung bean mottle potyvirus, Narcissus degeneration potyvirus, Narcissus late season yellows potyvirus, Nerine Y potyvirus, Nothoscordum mosaic potyvirus, Oak ringspot virus, Orchid fleck rhabdovirus, Palm mosaic potyvirus, Parsley green mottle potyvirus, Parsley rhabdovirus, Parsnip leafcurl virus, Passionfruit Sri Lankan mottle potyvirus, Passionfruit vein-clearing rhabdovirus, Patchouli mottle rhabdovirus, Pea stem necrosis virus, Peanut top paralysis potyvirus, Peanut veinal chlorosis rhabdovirus, Pecteilis mosaic potyvirus, Pepper mild mosaic potyvirus, Perilla mottle potyvirus, Pigeonpea proliferation rhabdovirus, Pigeonpea sterility mosaic virus, Plantain 7 potyvirus, Plantain mottle rhabdovirus, Pleioblastus chino potyvirus, Poplar decline potyvirus, Primula mottle potyvirus, Purple granadilla mosaic virus, Ranunculus repens symptomless rhabdovirus, Rice yellow stunt virus, Saintpaulia leaf necrosis rhabdovirus, Sambucus vein clearing rhabdovirus, Sarracenia purpurea rhabdovirus, Shamrock chlorotic ringspot potyvirus, Soybean mild mosaic virus, Soybean rhabdovirus, Soybean spherical virus, Soybean yellow vein virus, Soybean Z potyvirus, Strawberry latent C rhabdovirus, Strawberry mottle virus, Strawberry pallidosis virus, Sunflower mosaic potyvirus, Sweet potato latent potyvirus, Teasel mosaic potyvirus, Thimbleberry ringspot virus, Tomato mild mottle potyvirus, Trichosanthes mottle potyvirus, Tulip halo necrosis virus, Tulip mosaic virus, Turnip vein-clearing virus, Urd bean leaf crinkle virus, Vigna sinensis mosaic rhabdovirus, Watercress yellow spot virus, Watermelon Moroccan mosaic potyvirus, Wheat chlorotic spot rhabdovirus, White bryony potyvirus, Wineberry latent virus, Zinnia mild mottle potyvirus, Zoysia mosaic potyvirus Weeds In certain embodiments, the target organism is a weed. As used herein, the term "weed" refers to any unwanted plant. The weed to be controlled may include monocotyledonous species, such as species of the genus *Agrostis, Alopecurus, Avena, Bromus, Cyperus, Digitaria, Echinochloa, Lolium, Monochoria, Rottboellia, Sagittaria, Scirpus, Setaria, Sida* or *Sorghum*, and dicotyledonous species, for example species of the genus *Abutilon, Amaranthus, Chenopodium, Chrysanthemum, Conyza, Galium, Ipomoea, Nasturtium, Sinapis, Solanum, Stellaria, Veronica, Viola* or *Xanthium*. Weeds can also include plants which may be considered crop plants but which are growing outside a crop area (escapes), or which grow from seed left over from a previous planting of a different crop (volunteers). Such volunteers or escapes may be tolerant to certain other herbicides.

It has been demonstrated that several agriculturally relevant traits in plants can be modified via the introduction of transgenes that target the silencing of specific genes, including soybean oil composition and corn kernel protein composition. dsRNAs targeting specific genes in specific species can be applied topically to alter plant traits as well, and in some cases, offers the farmer more flexibility with regard to timing and endurance of application. In certain embodiments the compositions of the present invention may be used to enhance a yield-related trait in a plant. Yield-related traits that may be enhanced by the compositions of the present invention include, but are not limited to, total seed germination, rate of seed germination, plant biomass, disease tolerance, insect tolerance, drought tolerance, heat tolerance, cold tolerance, salinity tolerance, tolerance to heavy metals, total yield, seed yield, root growth, early vigor, plant biomass, plant size, total plant dry weight, above-ground dry weight, above-ground fresh weight, leaf area, stem volume, plant height, rosette diameter, leaf length, root length, root mass, tiller number, and leaf number.

Crop Plants

Representative crop plants that may be target organisms include monocotyledonous and dicotyledonous plants including but not limited to fodder or forage legumes, ornamental plants, food crops, trees, or shrubs selected from *Acer* spp., *Allium* spp., *Amaranthus* spp., *Ananas comosus, Apium graveolens, Arachis* spp, *Asparagus officinalis, Beta vulgaris, Brassica* spp. (e.g., *Brassica napus, Brassica rapa* ssp. [canola, oilseed rape, turnip rape]), *Camellia sinensis, Canna indica, Cannabis sativa, Capsicum* spp., *Castanea* spp., *Cichorium endivia, Citrullus lanatus, Citrus* spp., *Cocos* spp., *Coffea* spp., *Coriandrum sativum, Corylus* spp., *Crataegus* spp., *Cucurbita* spp., *Cucumis* spp., *Daucus carota, Fagus* spp., *Ficus carica, Fragaria* spp., *Ginkgo biloba, Glycine* spp. (e.g., *Glycine max, Soja hispida* or *Soja max*), *Gossypium hirsutum, Helianthus* spp. (e.g., *Helianthus annuus*), *Hibiscus* spp., *Hordeum* spp. (e.g., *Hordeum vulgare*), *Ipomoea batatas, Juglans* spp., *Lactuca sativa, Linum usitatissimum, Litchi chinensis, Lotus* spp., *Luffa acutangula, Lupinus* spp., *Lycopersicon* spp. (e.g., *Lycopersicon esculenturn, Lycopersicon lycopersicum, Lycopersicon pyriforme*), *Malus* spp., *Medicago sativa, Mentha* spp., *Miscanthus sinensis, Morus nigra, Musa* spp., *Nicotiana* spp., *Olea* spp., *Oryza* spp. (e.g., *Oryza sativa, Oryza latifolia*), *Panicum miliaceum, Panicum virgatum, Passiflora edulis, Petroselinum crispum, Phaseolus* spp., *Pinus* spp., *Pistacia vera, Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. Especially preferred are rice, oilseed rape, canola, soybean, corn (maize), cotton, sugarcane, alfalfa, sorghum, and wheat.

In certain embodiments, a target gene of interest my also include a gene that is essential to the survival of an organism, such as a weed, insect, or plant pathogen, and can serve as a target for controlling growth and proliferation of the organism. For example, dsRNA-mediated silencing of an essential gene in an insect pest can induce cessation of feeding and ultimately growth inhibition, morbidity, or mortality. Recent studies have shown that certain coleopteran insect species, most notably the western corn rootworm, *Diabrotica virgifera virgifera*, are exquisitely sensitive to ingested dsRNAs. Highly efficacious dsRNAs yield LC50 values in the parts-per-billion (ppb or ng/ml) range with this species. RNAi provides a unique mode of action for the control of insect pests that could complement the current strategy of expressing *Bacillus thuringiensis* insecticidal proteins in plants of agricultural importance. In certain embodiments, dsRNAs targeting essential insect genes can be delivered via topical sprays for RNAi-mediated insect control.

Non-Target Organisms

In some embodiments, the compositions of the invention may be applied to an organism that is different from the target organism. For example, in some embodiments the target organism is an insect, and the composition is applied to a non-target organism, such as a plant, that is a host for the insect. As used herein, a "non-target organism" is any organism other than the target organism. Where the target organism and host organism differ, a non-target organism can comprise a host organism and organisms that consume the host organism or otherwise contact polynucleotides (e.g., siRNAs or antisense polynucleotides) or proteins expressed in a host organism. The target-specific design of polynucleotides such as RNAi and antisense polynucleotides, as described herein, provides that such polynucleotides have little or no gene silencing activity in non-target organisms.

Non-target organisms include crop plants that may be infected with a target organism, such as a plant pathogen or insect. Representative crop plants include monocotyledonous and dicotyledonous plants including but not limited to fodder or forage legumes, ornamental plants, food crops, trees, or shrubs selected from *Acer* spp., *Allium* spp., *Amaranthus* spp., *Ananas comosus*, *Apium graveolens*, *Arachis* spp., *Asparagus officinalis*, *Beta vulgaris*, *Brassica* spp. (e.g., *Brassica napus*, *Brassica rapa* ssp. [canola, oilseed rape, turnip rape]), *Camellia sinensis*, *Canna indica*, *Cannabis saliva*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g., *Glycine max*, *Soja hispida* or *Soja max*), *Gossypium hirsutum*, *Helianthus* spp. (e.g., *Helianthus annuus*), *Hibiscus* spp., *Hordeum* spp. (e.g., *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g., *Lycopersicon esculenturn*, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g., *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. Especially preferred are rice, oilseed rape, canola, soybean, corn (maize), cotton, sugarcane, alfalfa, sorghum, and wheat.

Application of the Compositions

In certain embodiments, the compositions described herein can be applied as a spray or powder to the plant, plant part, seed, a pest, or an area of cultivation. In certain embodiments, the compositions can be formulated as a bait, food substance, or attractant. For example, the compositions can be incorporated into an insect bait suitable for oral administration of the composition to the target insect. The bait may comprise a composition comprising an active agent and a hydrazinyl and hydrazinylalcohol lipidoid of the invention dispersed in a carrier, and an edible insect attractant. In some embodiments, the bait comprises an edible insect attractant and a nanoparticle or microparticle comprising the active agent and hydrazinyl and hydrazinylalcohol lipidoid, wherein the nanoparticle or microparticle is dispersed in a carrier. Typically, the composition and attractant are mixed together before being dispersed in the desired carrier. Suitable attractants include any type of insect food and/or attractant which will lure the insect to the bait to ingest the bait. Exemplary insect foods or attractants include any type of insect food, including various sugars, proteins, carbohydrates, yeast, fats, and/or oils. The bait can be in any form suitable for delivery and ingestion of the composition, depending on the habitat and target insect, but will typically be a liquid, gel, self-sustaining gel-matrix, or solid bait (e.g., tablets, granules, etc.). Exemplary carriers include, without limitation, agarose gel, gelatin gel, and/or pectin gel. In some embodiments, the carrier is agarose gel, which is especially suited for aquatic habitats and breeding grounds. Insect baits are known in the art and are described, for example, in U.S. Pat. No. 8,841,272.

The compositions are present in the bait in an effective amount (i.e., concentration) for the activity of the active agent, such as gene silencing. The concentration of the active agent in the bait may be about 0.001, 0.005, 0.01, 0.05, 0.1, 0.5, 1, 2, 3, 4, 5, 6, 7, 8, 9, 10, 11, 12, 13, 14, 15, 16, 17, 18, 19 or 20% by weight of the bait. Any of these values may be used to define a range for the concentration of the active agent in the bait. For example, the concentration of the active agent in the bait may range from about 0.1 to about 1%, or from about 1 to about 5% by weight of the bait. The weight ratio of active agent to insect attractant (food) in the bait may be about 1:1, 1:5, 1:10, 1:20, 1:30, 1:40, 1:50, 1:60, 1:70, 1:80, 1:90, 1:100, 1:150 or 1:200. Any of these values may be used to define a range for the weight ratio of the active agent to the insect attractant in the bait. For example, the weight ratio of the active agent to the insect attractant in the bait may be from about 1:20 to about 1:200, or from about 1:50 to about 1:100.

In some embodiments, the concentration of the microparticle or nanoparticle comprising the active agent and the hydrazinyl and hydrazinylalcohol lipidoid in the bait may be about 0.001, 0.005, 0.01, 0.05, 0.1, 0.5, 1, 2, 3, 4, 5, 6, 7, 8, 9, 10, 11, 12, 13, 14, 15, 16, 17, 18, 19 or 20% by weight of the bait. Any of these values may be used to define a range for the concentration of the microparticle or nanoparticle in the bait. For example, the concentration of the microparticle or nanoparticle in the bait may range from about 0.1 to about 1%, or from about 1 to about 5% by weight of the bait. The weight ratio of the microparticle or nanoparticle to insect attractant (food) in the bait may be about 1:1, 1:5, 1:10, 1:20, 1:30, 1:40, 1:50, 1:60, 1:70, 1:80, 1:90, 1:100, 1:150 or 1:200. Any of these values may be used to define a range for the weight ratio of the microparticle or nanoparticle to the insect attractant in the bait. For example, the weight ratio of the microparticle or nanoparticle to the insect attractant in the bait may be from about 1:20 to about 1:200, or from about 1:50 to about 1:100.

The compositions of the invention may also be applied as concentrated emulsions, dusts, emulsifiable concentrates, fumigants, gels, granules, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph No. 2, 5th Edition by CropLife International (2002). Agricultural formulations are also described, for example, in U.S. Pat. No. 8,815,271.

For example, the compositions of the invention may be applied as aqueous suspensions or emulsions prepared from concentrated formulations. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the composition, a carrier, and surfactants. The carrier may be selected from attapulgite clays, montmorillonite clays, diatomaceous earths, and purified silicates. Effective surfactants, comprising from about 0.5% to about 10% of the wettable powder, include sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates comprise a suitable concentration of the composition, such as from about 50 to about 500 grams per liter of liquid dissolved in a carrier that is either a water miscible solvent or a mixture of water-immiscible organic solvent and emulsifiers. Suitable organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble forms of the compositions of the invention dispersed in an aqueous carrier at a concentration in the range from about 5% to about 50% by weight. Ingredients, such as inorganic salts and synthetic or natural gums may also be added, to increase the density and viscosity of the aqueous carrier.

The compositions may also be applied as granular compositions, for example, for applications to the soil. Granular compositions may contain from about 0.5% to about 10% by weight of the composition, dispersed in a carrier that comprises clay or a similar substance. Such compositions may be prepared by dissolving the composition in a suitable solvent and applying it to a granular carrier which has been preformed to a suitable particle size, for example, in the range of from about 0.5 to about 3 mm. Such compositions may also be formulated by making a dough or paste of the carrier and compound and crushing and drying to obtain the desired granular particle size.

Dusts comprising the compositions of the invention may be prepared by intimately mixing the composition in powdered form with a suitable dusty agricultural carrier, such as kaolin clay, ground volcanic rock, and the like. Dusts may contain from about 1% to about 10% by weight of the composition. They may be applied as a seed dressing or as a foliage application with a dust blower machine.

The compositions may also be applied in the form of a solution in an appropriate organic solvent (e.g. petroleum oil) such as the spray oils, which are widely used in agricultural chemistry.

The composition may also be applied in the form of an aerosol composition. The composition is dissolved or dispersed in a carrier, which is a pressure-generating propellant mixture. The aerosol composition is packaged in a container from which the mixture is dispensed through an atomizing valve.

Agriculturally acceptable carriers may also include surface active agents, stickers, spreader stickers, inert carriers, preservatives, humectants, dyes, U.V. (ultra-violet) protectants, buffers, flow agents, antifoams (e.g. polydimethylsiloxane), sodium aluminosilicate or other components which facilitate product handling and application of the compositions. Examples of agriculturally acceptable inert carriers include inorganic minerals such as kaolin, mica, gypsum, fertilizer, carbonates, sulfates, or phosphates; organic materials such as sugar, starches or cyclodextrins; or botanical materials such as wood products, cork, powdered corn cobs, rice hulls, peanut hulls and walnut shells. Agriculturally acceptable carriers are described, for example in U.S. Pat. No. 6,984,609.

The compositions may further comprise one or more additional compounds to facilitate passage of the active agent through the plant cell wall. Several technologies for facilitating passage of compounds through the plant cell wall are known in the art. For example, U.S. Pat. No. 8,609,420 describes conjugation of the active agent to a semi-conductor nanoparticle within the size range of 3-5 nm (e.g. a "quantum dot") and one or more cell penetrating peptides to improve penetration of the plant cell and intracellular delivery of the active agent. U.S. Pat. No. 8,686,222 describes interacting a polyamidoamine dendrimer and one or more cell penetrating peptides with the active agent to improve cell penetration. U.S. Pat. No. 8,653,327 describes delivery of active agents through plant cell walls by coating a PEGylated semiconductor nanoparticle with the active agent. U.S. Pat. No. 8,722,410 describes transferring active agents into plant cells by applying the active agent to a nanoparticle coated with a subcellular compartment targeting protein. U.S. Pat. Nos. 8,609,420, 8,686,222, 8,653,327, and 8,722,410 are incorporated by reference herein in their entirety.

Therapeutic Applications

In another aspect, the presently disclosed hydrazinylalcohol lipidoid-based formulations can be used to deliver a therapeutic agent to a target in a subject for the purpose of treating or preventing a disease or disorder. In certain embodiments, the presently disclosed hydrazinylalcohol lipidoid-based formulations are combined with a pharmaceutically acceptable excipient and/or carrier to form a pharmaceutical formulation. In certain embodiments, the disease or disorder is treated or prevented by administering a therapeutically effective amount of the pharmaceutical formulation to a subject in need thereof. In certain embodiments, the subject is a mammal. In certain embodiments, the subject is a human.

In certain embodiments, the presently disclosed hydrazinylalcohol lipidoid-based formulations, i.e., complexes, microparticles, nanoparticles, picoparticles, liposomes, and micelles, are combined with one or more pharmaceutically acceptable excipients and/or carriers to form pharmaceutical formulations suitable to administer to mammals, including humans. Examples of classes of such excipients and carriers include, but are not limited to, fillers, extenders, binders, humectants, disintegrants, plasticizers, stabilizers, solution retarding agents, wetting agents, suspending agents, thickening agents, absorbents, lubricants, surfactants, buffering agents, diluents, solvents, emulsifying agents, suspending agents, sweetening agents, flavoring agents, perfuming agents, opacifying agents, separating agents, and coating permeability adjusters. Excipients and/or carriers may comprise about 1%, 2%, 3%, 4%, 5%, 10%, 15%, 20%, 25%, 30%, 40%, 50%, or higher percentage of the presently disclosed pharmaceutical formulations.

The pharmaceutical compositions of this invention can be administered to mammals, including humans, by any conventional route. Examples of such routes include, but are not limited to, orally, rectally, parenterally, intracisternally, intravaginally, intranasally, intraperitoneally, topically, bucally, or as an oral or nasal spray. Dosage forms for oral administration include, but are not limited to, solid and liquid dosage forms. Solid dosage forms for oral administration include, but are not limited to, capsules, tablets, pills, powders, and granules. Liquid dosage forms for oral administration include, but are not limited to, emulsions, microemulsions, solutions, suspensions, syrups, and elixirs. Dosage forms for topical administration include, but are not limited to, ointments, pastes, creams, lotions, gels, powders, solutions, sprays, inhalants, and transdermal patches.

As used herein, "parenteral administration" and "administered parenterally" means modes of administration other than enteral and topical administration, usually by injection, and includes, but is not limited to, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Although the dosage will vary depending on the symptoms, age and body weight of the subject, the nature and severity of the disorder to be treated or prevented, the route of administration and the form of the drug, in general, a daily dosage of from 0.01 to 2000 mg of the therapeutic agent is recommended for an adult human patient, and this may be administered in a single dose or in divided doses.

As used herein, the term "therapeutic agent" includes any synthetic or naturally occurring biologically active compound or composition which, when administered to subject, induces a desired pharmacologic, immunogenic, and/or physiologic effect by local and/or systemic action. The term therefore encompasses those compounds or chemicals traditionally regarded as drugs, vaccines, and biopharmaceuticals, including molecules such as proteins, peptides, hormones, nucleic acids, and gene constructs. More particularly, the term "therapeutic agent" includes compounds or compositions for use in all of the major therapeutic areas.

Examples of such therapeutic agents include, but are not limited to, nucleic acids, adjuvants, anti-infectives such as antibiotics and antiviral agents, analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators, central nervous system stimulants, cough and cold preparations, decongestants, diagnostics, hormones, bone growth stimulants and bone resorption inhibitors, oncology drugs (e.g., chemotherapy drugs, hormonal therapeutic agents, immunotherapeutic agents, radiotherapeutic agents), lipid-lowering agents, antidepressants, stimulants, antibiotics, birth control medication, anti-angiogenics, cytovascular agents, signal transduction inhibitors, hormones, vasoconstrictors, and steroids, immunosuppressives, muscle relaxants, psychostimulants, sedatives, tranquilizers, proteins, peptides, and fragments thereof (whether naturally occurring, chemically synthesized or recombinantly produced), small molecules and other biologically active macromolecules such as, for example, proteins and enzymes. The agent may be a biologically active agent used in medical, including veterinary, applications. The term therapeutic agent also includes without limitation, medicaments, vitamins; mineral supplements, substances used for the treatment, prevention, diagnosis, cure or mitigation of disease or illness, substances which affect the structure or function of the body, or pro-drugs, which become biologically active or more active after they have been placed in a predetermined physiological environment. These therapeutic agents may be administered alone with pharmaceutical formulations or in combination (e.g., co-administered) with pharmaceutical formulations comprising nucleic acid, such as interfering RNA.

Examples of nucleic acids include, but are not limited to, interfering RNA molecules (e.g., siRNA, aiRNA, miRNA), antisense oligonucleotides, plasmids, ribozymes, immunostimulatory oligonucleotides, and mixtures thereof.

Nucleic acids delivered as the therapeutic agent in the presently disclosed pharmaceutical formulations can be used to downregulate or silence the translation (i.e., expression) of a target gene of interest in the target organism. Examples of classes of genes that can be downregulated or silenced include, but are not limited to, genes associated with viral infection and survival, genes associated with metabolic diseases and disorders (e.g., liver diseases and disorders), genes associated with tumorigenesis and cell transformation (e.g., cancer), angiogenic genes, immunomodulator genes such as those associated with inflammatory and autoimmune responses, ligand receptor genes, and genes associated with neurodegenerative disorders. Examples viral sequences that can be downregulated or silenced include filoviruses such as Ebola virus and Marburg virus, arenaviruses such as Lassa virus, Junin virus, Machupo virus, Guanarito virus, and Sabia virus, influenza viruses such as Influenza A, B, and C viruses, hepatitis viruses, Human Immunodeficiency Virus (HIV), herpes viruses, and Human Papilloma Viruses (HPV).

Examples of peptides or polypeptide that may be used as therapeutic agents include, but are not limited to, an antibodies such as a polyclonal antibodies, a monoclonal antibodies, antibody fragments, humanized antibodies, recombinant antibodies, recombinant human antibodies, Primatized™ antibodies, cytokines, growth factors, apoptotic factors, differentiation-inducing factors, cell-surface receptors, ligands, hormones, or small molecules.

Examples of oncology drugs that may be used as therapeutic agents include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, Leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, velban, ellipticin and ellipticin analogs or derivatives, epothilones, intracellular kinase inhibitors, and camptothecins.

Examples of anti-viral drugs that may be used as therapeutic agents include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, immunovir, idoxuridine, imiquimod, indinavir, inosine, integrase inhibitors, interferon type III (e.g., IFN-λ molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ, interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In certain embodiments, the therapeutic agent to be delivered may be a prophylactic agent. Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, and Freund's adjuvant.

Examples of prophylactic agents include, but are not limited to, (1) antigens of the following bacterial organisms: *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*, (2) antigens of the following viruses: smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, and hepatitis A, B, C, D, and E virus, and (3) antigens of the following fungal, protozoan, and parasitic organisms: *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*. These antigens may be in the form of whole killed organisms, peptides, proteins, glycoproteins, carbohydrates, or combinations thereof.

EXAMPLES

Example 1

Synthesis of 1-[[bis(2-hydroxydodecyl)aminol-(2-hydroxydodecyl)amino]dodecan-2-ol (Compound 11)

To a 2 dram vial flushed with Argon was added hydrazine (48.54 µL, 50.00 mg, 998.60 µmol) and 1,2-epoxydodecane (1.31 mL, 1.10 g, 5.99 mmol). The neat reaction mixture was stirred at 120° C. for 2 days, after which it was cooled to ambient temperature. The reaction mixture was purified via flash column chromatography using MeOH (10% NH$_4$OH)/DCM 0% to 15%, yielding 1-[[bis(2-hydroxydodecyl)amino]-(2-hydroxydodecyl)amino]dodecan-2-ol (351.00 mg, 456.25 µmol) in 45.69% yield.

Example 2

Synthesis of 1-[[bis(2-hydroxytetradecyl)amino]-(2-hydroxytetradecyl)amino]tetradecan-2-ol and 1-[2,2-bis(2-hydroxytetradecyl)hydrazino]tetradecan-2-ol (Compounds 7 and 8)

To a 2 dram vial flushed with Argon was added hydrazine (48.97 µL, 50.00 mg, 998.60 µmol) and 1,2-epoxytetradecane (1.51 mL, 1.27 g, 5.99 mmol). The neat reaction mixture was stirred at 120° C. for 2 days, after which it was cooled to ambient temperature. The reaction mixture was purified via flash column chromatography using MeOH (10% NH$_4$OH)/DCM 0% to 15%, yielding 1-[[bis(2-hydroxytetradecyl)amino]-(2-hydroxytetradecyl)amino]tetradecan-2-ol (270.00 mg, 306.29 µmol) in 30.67% yield and 1-[2,2-bis(2-hydroxytetradecyl)hydrazino]tetradecan-2-ol (287.00 mg, 428.90 µmol) in 42.95% yield.

Example 3

Synthesis of 1-[[bis(2-hydroxydodecyl)amino]-methyl-amino]dodecan-2-ol and 1-[2-hydroxydodecyl(methylamino)amino]dodecan-2-ol (Compounds 9 and 53)

To a 2 dram vial flushed with Argon was added methylhydrazine (25.00 mg, 542.63 µmol) and 1,2-epoxydodecane (600.09 mg, 3.26 mmol, 6 eq.). The neat reaction mixture was stirred at 120° C. for 2 days, after which it was cooled to ambient temperature. The reaction mixture was purified via flash column chromatography using MeOH (10% NH$_4$OH)/DCM 0% to 15%, yielding 1-[[bis(2-hydroxydodecyl)

amino]-methyl-amino]dodecan-2-ol as colorless oil and 1-[2-hydroxydodecyl(methylamino)amino]dodecan-2-ol as colorless oil.

Example 4

Synthesis of hexyl 3-[[bis(3-hexoxy-3-oxo-propyl)amino]-methyl-amino]propanoate and hexyl 3-(2-methyl-3-oxo-pyrazolidin-1-yl)propanoate (Compounds 82 and 81)

To a 2 dram vial flushed with Argon was added methylhydrazine (43.75 mg, 949.61 umol) and hexyl prop-2-enoate (593.40 mg, 3.80 mmol, 4 eq.). The neat reaction mixture was stirred at 120° C. for 2 days, after which it was cooled to ambient temperature. The reaction mixture was purified via flash column chromatography using MeOH (10% NH$_4$OH)/DCM 0% to 15%, yielding hexyl 3-[[bis(3-hexoxy-3-oxo-propyl)amino]-methyl-amino]propanoate as colorless oil and hexyl 3-(2-methyl-3-oxo-pyrazolidin-1-yl)propanoate as off white wax.

Example 5

Nanoparticle Formulation Using Compound 10

Stock ethanolic solutions of compound 10, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. The isolated nanoparticles have a $Z_{avg}$ size of 323.4 nm with a polydispersity index of 0.179 and a zeta potential of −4.57 mV.

Example 6

Nanoparticle Formulation Using Compound 11

Stock ethanolic solutions of compound 11, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. The isolated nanoparticles have a $Z_{avg}$ size of 420.4 nm with a polydispersity index of 0.079 and a zeta potential of −5.99 mV. Particle size as determined by Dynamic Light Scattering (DLS) was 180 nm. The nanoparticles had an entrapment efficiency, as determined using a Ribogreen assay, of 99%.

Example 7

Nanoparticle Formulation Using Compound 8

Stock ethanolic solutions of compound 8, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. The isolated nanoparticles have a $Z_{avg}$ size of 1492 nm with a polydispersity index of 0.314 and a zeta potential of −22.7 mV. Particle size as determined by Dynamic Light Scattering (DLS) was 153 nm. The nanoparticles had an entrapment efficiency, as determined using a Ribogreen assay, of 89%.

Example 8

Nanoparticle Formulation Using Compound 9

Stock ethanolic solutions of compound 9, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. The isolated nanoparticles have a $Z_{avg}$ size of 4216 nm with a polydispersity index of 0.255 and a zeta potential of −13.6 mV.

Example 9

Nanoparticle Formulation Using Compound 15

Stock ethanolic solutions of compound 15, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 135 nm. The nanoparticles had an entrapment efficiency, as determined using a Ribogreen assay, of 94%.

Example 10

Nanoparticle Formulation Using Compound 24

Stock ethanolic solutions of compound 24, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 184 nm. The nanoparticles had an entrapment efficiency, as determined using a Ribogreen assay, of 99%.

Example 11

Nanoparticle Formulation Using Compound 26

Stock ethanolic solutions of compound 26, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 119 nm. The nanoparticles had an entrapment efficiency, as determined using a Ribogreen assay, of 89%.

Example 12

Nanoparticle Formulation Using Compound 28

Stock ethanolic solutions of compound 28, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 138 nm. The nanoparticles had an entrapment efficiency, as determined using a Ribogreen assay, of ~61%.

Example 13

Nanoparticle Formulation Using Compound 42

Stock ethanolic solutions of compound 42, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 184 nm. The nanoparticles had an entrapment efficiency, as determined using a Ribogreen assay, of ~44%.

Example 14

Nanoparticle Formulation Using Compound 53

Stock ethanolic solutions of compound 53, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 169 nm. The nanoparticles had an entrapment efficiency, as determined using a Ribogreen assay, of 94%.

Example 15

Nanoparticle Formulation Using Compound 60

Stock ethanolic solutions of compound 60, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 157 nm. The nanoparticles had an entrapment efficiency, as determined using a Ribogreen assay, of ~60%.

Example 16

Nanoparticle Formulation Using Compound 75

Stock ethanolic solutions of compound 75, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 144 nm. The nanoparticles had an entrapment efficiency, as determined using a Ribogreen assay, of ~50%.

Example 17

Nanoparticle Formulation Using Compound 86

Stock ethanolic solutions of compound 15, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 170 nm. The nanoparticles had an entrapment efficiency, as determined using a Ribogreen assay, of 89%.

Example 18

Nanoparticle Formulation Using Compound 88

Stock ethanolic solutions of compound 88, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 110 nm. The nanoparticles had an entrapment efficiency, as determined using a Ribogreen assay, of 93%.

Example 19

Nanoparticle Formulation Using Compound 90

Stock ethanolic solutions of compound 90, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 177 nm. The nanoparticles had an entrapment efficiency, as determined using a Ribogreen assay, of 82%.

Example 20

Nanoparticle Formulation Using Compound 103

Stock ethanolic solutions of compound 103, 1,2-Distearoyl-sn-glycero-3-phosphocholine (DSPC), cholesterol, 1,2-dimyristoyl-sn-glycero-3-phosphoethanolamine-N-[methoxy(polyethylene glycol)-2000] (C14-PEG) were prepared and combined to yield a molar ratio of 50:10:38.5:1.5 with the organic solution of 10% 10 mM citrate buffer at pH 5. An siRNA was dissolved in 10 mM citrate at pH5 buffer at a concentration of 0.1 mg/mL. The ethanolic solution was then added to the aqueous siRNA solution while stirred at 700 rpm, resulting in the precipitation of lipidoid nanoparticles. The lipidoid nanoparticles were separated from the supernatant. Particle size as determined by Dynamic Light Scattering (DLS) was 155 nm. The nanoparticles had an entrapment efficiency, as determined using a Ribogreen assay, of ~78%.

The invention claimed is:

1. A compound of formula (I):

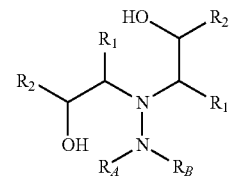

wherein:

$R_1$ is, independently, hydrogen, an optionally substituted $C_{1-20}$ aliphatic group, or an optionally substituted $C_{1-20}$ heteroaliphatic group;

$R_2$ is, independently, an optionally substituted $C_{1-20}$ aliphatic group or an optionally substituted $C_{1-20}$ heteroaliphatic group;

$R_A$ is hydrogen, an optionally substituted $C_{1-20}$ aliphatic group, an optionally substituted, $C_{1-20}$ heteroaliphatic group, or a group of formula (II):

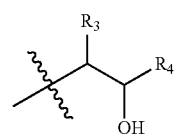

wherein $R_3$ is, independently, hydrogen, an optionally substituted $C_{1-20}$ aliphatic group, or an optionally substituted $C_{1-20}$ heteroaliphatic group; and $R_4$ is, independently, an optionally substituted $C_{1-20}$ aliphatic group or an optionally substituted $C_{1-20}$ heteroaliphatic group;

$R_B$ is a group of formula (II):

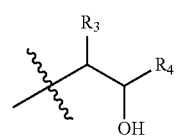

wherein $R_3$ is, independently, hydrogen, an optionally substituted $C_{1-20}$ aliphatic group, or an optionally substituted $C_{1-20}$ heteroaliphatic group; and $R_4$ is, independently, an optionally substituted $C_{2-20}$ aliphatic group or an optionally substituted $C_{1-20}$ heteroaliphatic group; and wherein any one or more of $R_1$, $R_2$, $R_3$, and $R_4$ together with another $R_1$, $R_2$, $R_3$, or $R_4$ or one of $R_A$ and $R_B$ optionally defines a carbocyclic system; and $R_A$ and $R_B$ together optionally define a carbocyclic ring system.

2. The compound of claim 1, wherein $R_A$ and $R_B$ are each a group of formula (II):

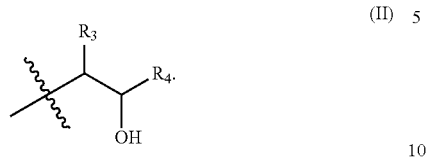

(II)

3. The compound of claim 2, wherein $R_1$ and $R_3$ are identical and $R_2$ and $R_4$ are identical.

4. The compound of claim 3, wherein $R_1$ and $R_3$ are hydrogen and $R_2$ and $R_4$ are an unbranched $C_{2-20}$ aliphatic group.

5. The compound of claim 4, wherein $R_2$ and $R_4$ are selected from the group consisting of n-butyl, n-pentyl, n-decanyl, and n-dodecanyl.

6. The compound of claim 2, wherein $R_1$ and $R_3$ are identical and $R_2$ and $R_4$ are different.

7. The compound of claim 6, wherein $R_1$ and $R_3$ are hydrogen, $R_2$ is an unbranched $C_{1-20}$ aliphatic group, and $R_4$ is an unbranched $C_{2-20}$ aliphatic group.

8. The compound of claim 1, wherein $R_A$ is hydrogen, methyl, or hydroxyethyl.

9. The compound of claim 8, wherein $R_B$ is a group of formula (II):

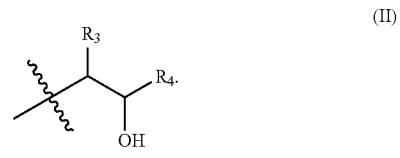

(II)

10. The compound of claim 9, wherein $R_1$ and $R_3$ are identical and $R_2$ and $R_4$ are identical.

11. The compound of claim 10, wherein $R_1$ and $R_3$ are hydrogen and $R_2$ and $R_4$ are an unbranched $C_{2-20}$ aliphatic group.

12. The compound of claim 11, wherein $R_2$ and $R_4$ are selected from the group consisting of n-butyl, n-pentyl, n-decanyl, or n-dodecanyl.

13. A compound selected from the group consisting of compounds formulae (4), (5), (6), (7), (8), (9), (10), (11), 52, 54, 56, 57, 84, 86, 87, 89, 91, 92, 107, 108, 109, 110, 111, 112, 115, and 116:

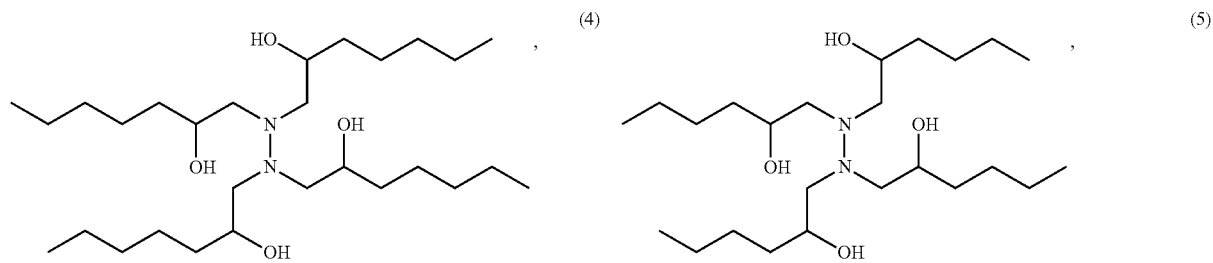

(4)

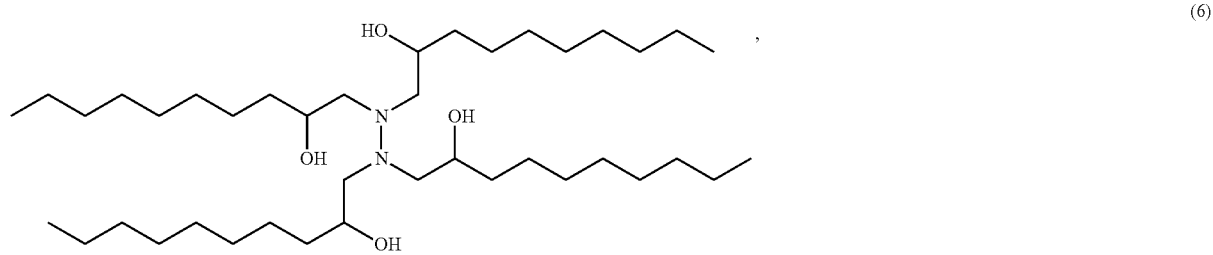

(5)

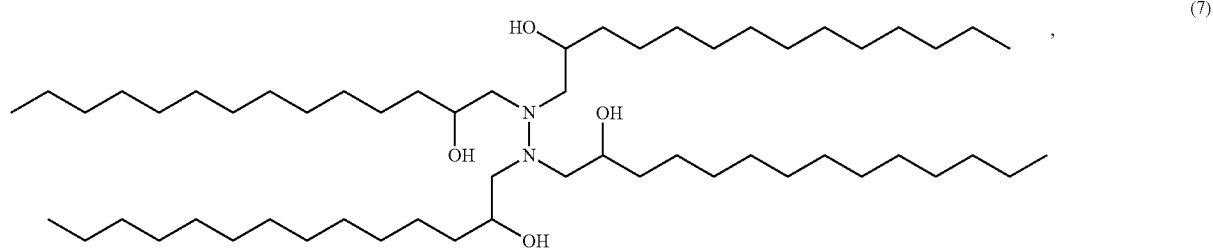

(6)

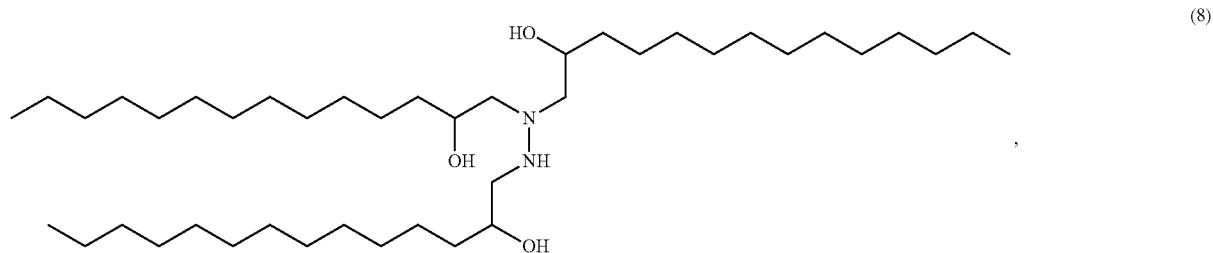

(7)

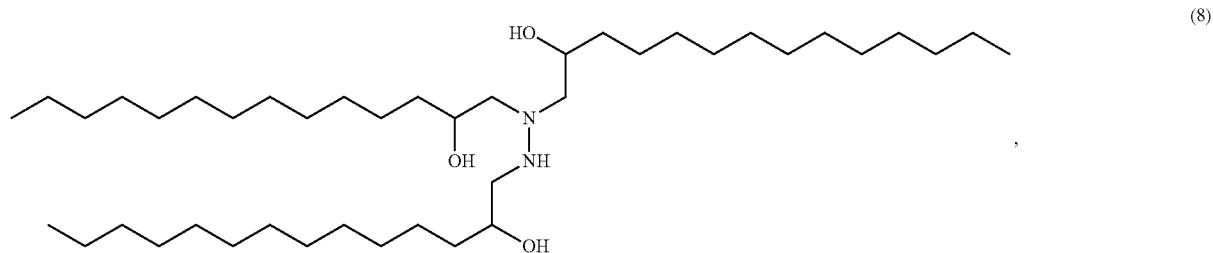

(8)

-continued
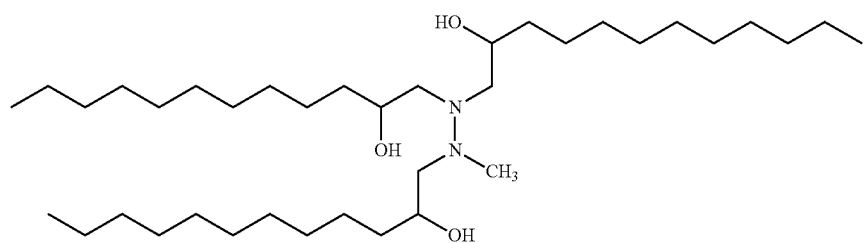
(9)
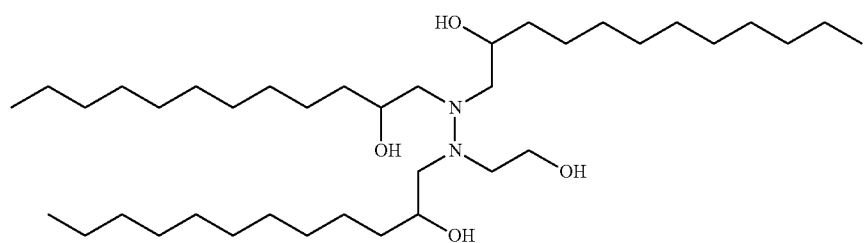
(10)
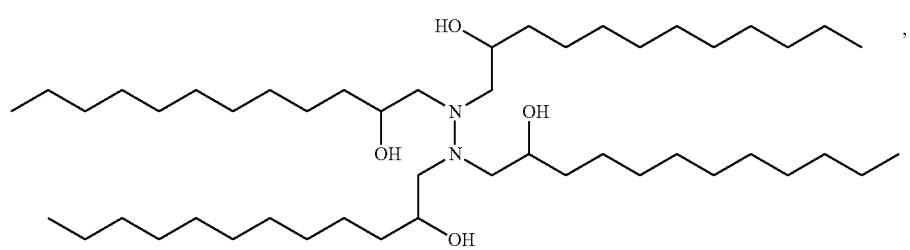
(11)
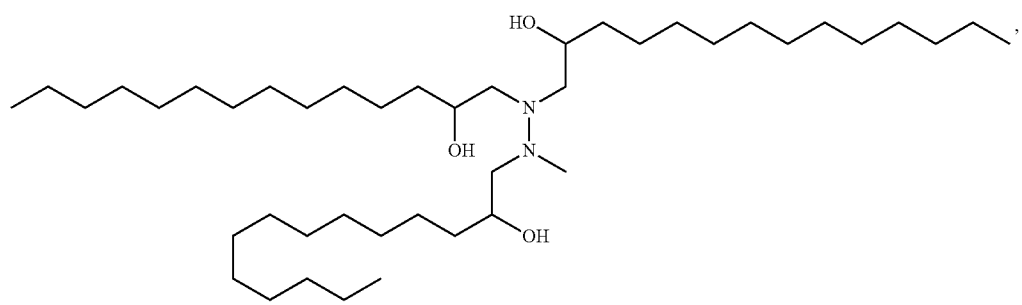
(52)
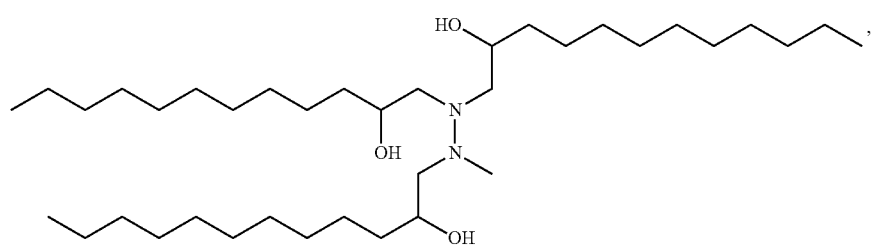
(54)
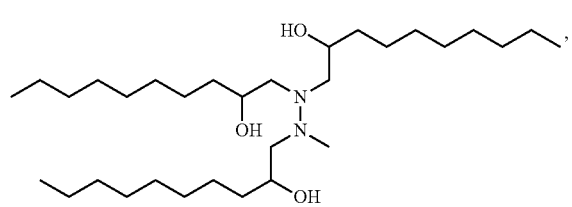
(56)
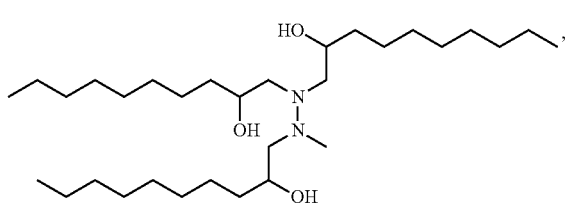
(57)

-continued
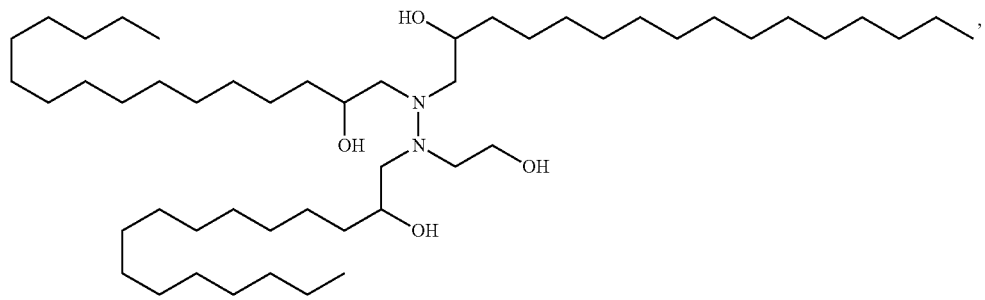 (84)
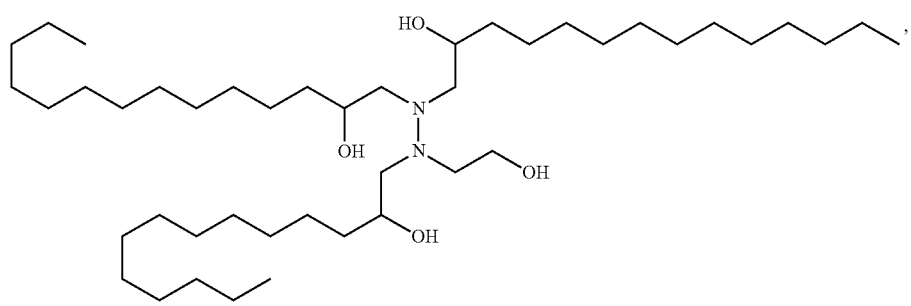 (86)
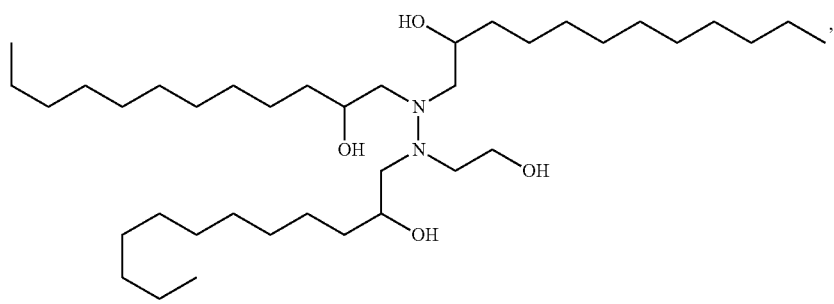 (87)
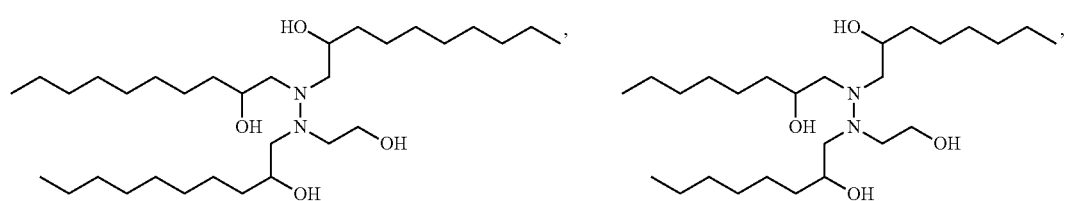
(89) (91)
(92)
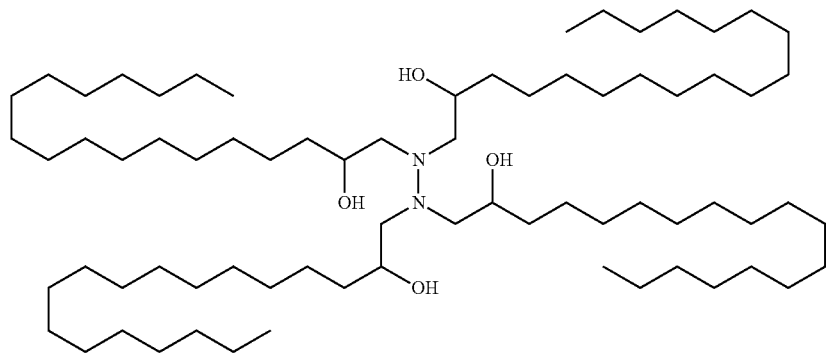

-continued
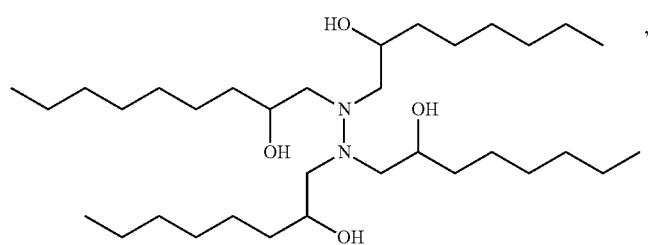
(107)
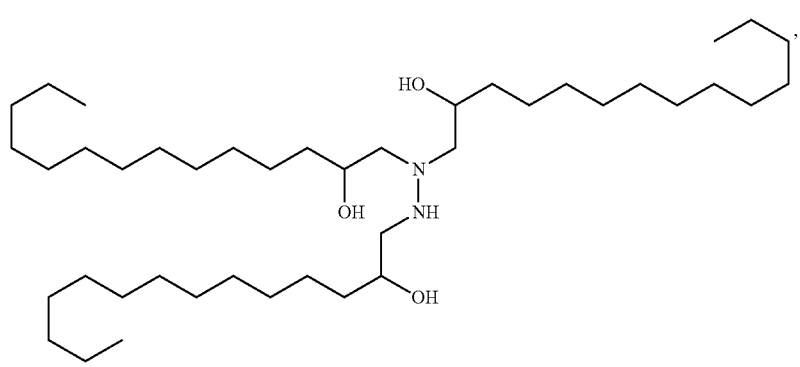
(108)
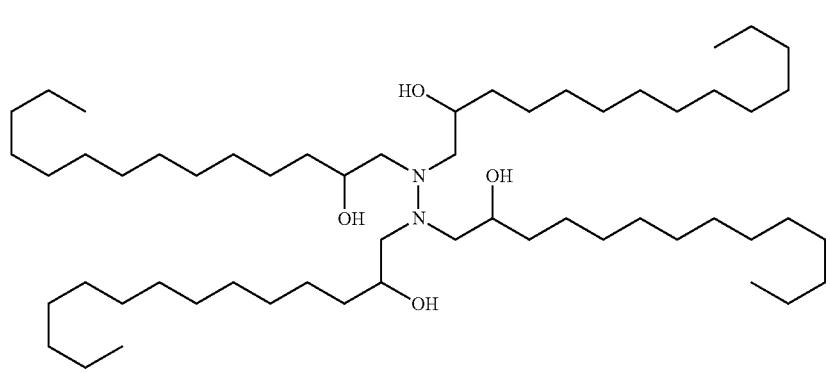
(109)
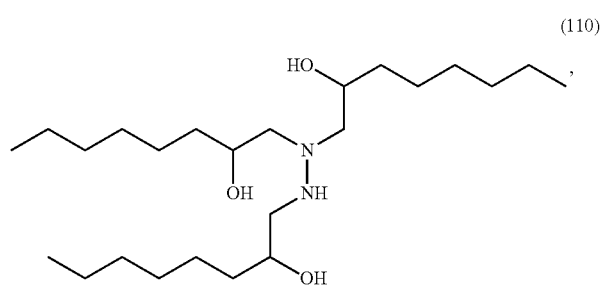
(110)
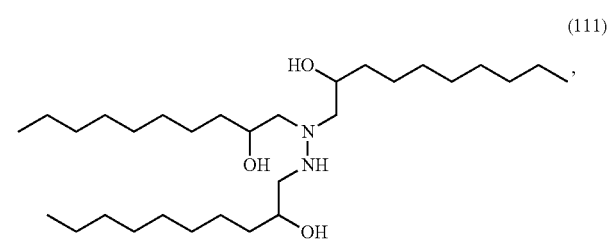
(111)
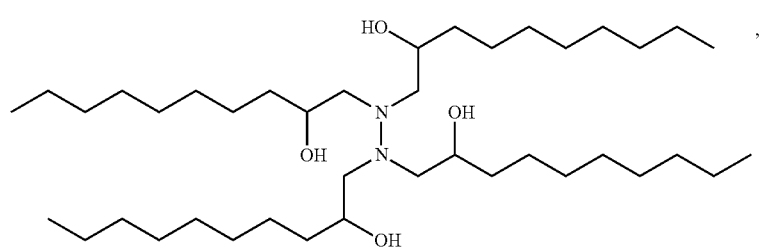
(112)

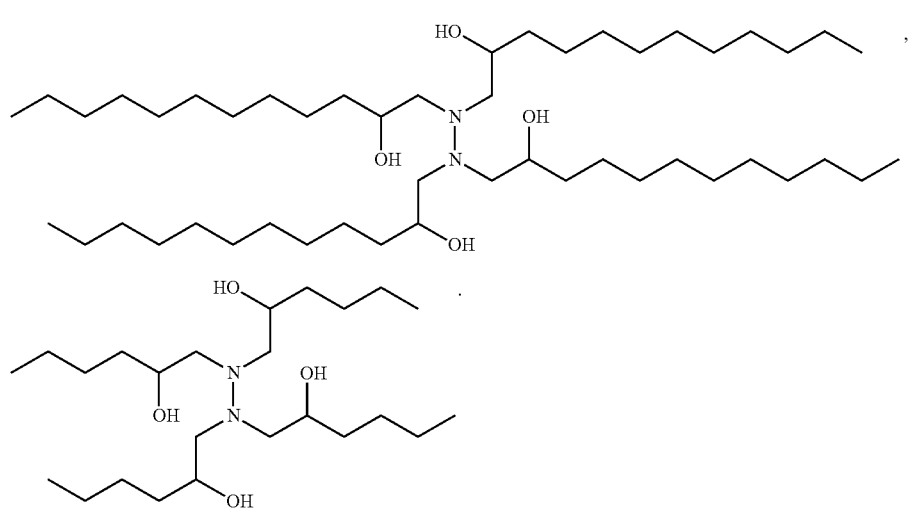

14. A microparticle or nanoparticle comprising a compound of claim 1 and an active agent to be delivered.

15. The microparticle or nanoparticle of claim 14, wherein the active agent to be delivered is selected from the group consisting of polynucleotides, oligonucleotides, proteins, and peptides.

16. The microparticle or nanoparticle of claim 15, wherein the active agent to be delivered is an oligonucleotide or a polynucleotide.

17. The microparticle or nanoparticle of claim 16, wherein the active agent to be delivered is an RNA.

18. The microparticle or nanoparticle of claim 17, wherein the RNA is a small interfering RNA (siRNA) or a double-stranded RNA (dsRNA).

19. A formulation comprising the compound of claim 1 and an active agent to be delivered.

20. The formulation of claim 19, wherein the active agent to be delivered is an oligonucleotide or a polynucleotide.

21. An herbicidal formulation comprising the compound of claim 1, an herbicidal agent to be delivered, and an agriculturally acceptable carrier.

22. An insecticidal formulation comprising the compound of claim 1, an insecticidal agent to be delivered, and an agriculturally acceptable carrier.

23. A formulation for controlling a plant pathogen, comprising the compound of claim 1, an agent to be delivered that controls a plant pathogen, and an agriculturally acceptable carrier.

24. A plant cell, insect cell or mammalian cell comprising the compound of claim 1.

* * * * *